US008921523B2

(12) United States Patent
Alard et al.

(10) Patent No.: US 8,921,523 B2
(45) Date of Patent: Dec. 30, 2014

(54) HUMANIZED ANTI-BETA-AMYLOID ANTIBODIES

(75) Inventors: Philippe Marc Louis Alard, Gent (BE); Ian Richard Catchpole, Stevenage (GB); Jonathan Henry Ellis, Stevenage (GB); Susannah Karen Ford, Stevenage (GB); Volker Germaschewski, Stevenage (GB); Gerald Wayne Gough, Stevenage (GB); Alan Peter Lewis, Stevenage (GB); Peter Ernest Soden, Stevenage (GB); Pamela Joan Thomas, Stevenage (GB); Trevor Anthony Kenneth Wattam, Stevenage (GB)

(73) Assignee: Glaxo Group Limited (GB)

( * ) Notice: Subject to any disclaimer, the term of this patent is extended or adjusted under 35 U.S.C. 154(b) by 1159 days.

(21) Appl. No.: 12/330,541

(22) Filed: Dec. 9, 2008

(65) Prior Publication Data
US 2009/0162358 A1    Jun. 25, 2009

Related U.S. Application Data

(60) Provisional application No. 61/043,839, filed on Apr. 10, 2008.

(30) Foreign Application Priority Data

Dec. 11, 2007   (GB) .................................. 0724185.4
Apr. 4, 2008   (GB) .................................. 0806230.9

(51) Int. Cl.
*C07K 16/46*   (2006.01)
*C07K 16/18*   (2006.01)
*A61K 39/395*   (2006.01)

(52) U.S. Cl.
USPC ................. 530/387.3; 530/387.9; 424/133.1; 424/139.1

(58) Field of Classification Search
None
See application file for complete search history.

(56) References Cited

U.S. PATENT DOCUMENTS

| | | | |
|---|---|---|---|
| 6,913,747 B1 * | 7/2005 | Co et al. ..................... | 424/153.1 |
| 2005/0163785 A1 * | 7/2005 | Knick et al. ............... | 424/155.1 |
| 2006/0292152 A1 * | 12/2006 | Rosenthal et al. ......... | 424/146.1 |

FOREIGN PATENT DOCUMENTS

WO   WO 2008/110885   9/2008

OTHER PUBLICATIONS

Padlan EA et al. Structure of an antibody-antigen complex: Crystal structure of the HyHEL-10 Fab-lysozyme complex. Proc Natl Acad Sci USA, 1989; 86:5938-5942.*
Paul WE, Editor. Fundamental Immunology, Third Edition. Raven Press, New York, 1993, pp. 292-295, under the heading "Fv Structure and Diversity in Three Dimensions".*
Rudikoff S et al. Single amino acid substitution altering antigen-binding specificity. Proc Natl Acad Sci USA, 1982; 79(6):1979-1983.*
Bard F et al. Epitope and isotype specificities of antibodies to beta-amyloid peptide for protection against Alzheimer's disease-like neuropathology. Proc. Natl. Acad Sci USA, 2003; 100(4):2023-2028.*
Casset et al. Biochem Biophys Res Comm. 2003; 307:198-205.*
Chen et al. J Mol Biol. 1999; 293:865-881.*
Hanan E & Solomon B. Inhibitory effect of monoclonal antibodies on Alzheimer's beta-amyloid peptide aggregation. Amyloid: Int. J. Exp. Clin. Invest. 1996; 3:130-133.*
Holm et al. Mol Immunol. 2007; 44(6):1075-1084.*
MacCallum et al. J Mol Biol. 1996; 262:732-745.*
Vajdos et al. J Mol Biol. 2002; 320(2):415-428.*
Wang, J. et al., (2008) J. Immunol. 181: 16651-6.

* cited by examiner

*Primary Examiner* — Kimberly A Ballard
(74) *Attorney, Agent, or Firm* — William T. Han; Jonathan M. Dermott

(57) ABSTRACT

Antigen binding proteins that bind β-amyloid peptide, in particular human β-amyloid peptide; methods of treating diseases or disorders characterized by elevated β-amyloid levels or β-amyloid deposits, particularly Alzheimer's disease and diseases or disorders affecting the eye or optic nerve characterized by elevated β-amyloid levels or β-amyloid deposits, including age related macular degeneration and glaucoma type diseases and β-amyloid dependent cataract formation, with the antigen binding proteins; pharmaceutical compositions comprising the antigen binding proteins; and methods of manufacture.

7 Claims, 3 Drawing Sheets

HUMANIZED ANTI-BETA-AMYLOID ANTIBODIES

CROSS REFERENCE TO PRIOR APPLICATIONS

This application claims the benefit of U.S. provisional application 61/043,839 filed Apr. 10, 2008, this application also claims benefit of the filing dates of Great Britain applications 0724185.4 filed Dec. 11, 2007 and 0806230.9 filed Apr. 4, 2008 the contents of which are incorporated herein by reference.

FIELD OF THE INVENTION

The present invention relates to antigen binding proteins, including antibodies, that bind β-amyloid peptide and in particular human β-amyloid peptide. The present invention also concerns methods of treating diseases or disorders characterised by elevated β-amyloid levels or β-amyloid deposits, particularly Alzheimer's disease and diseases or disorders affecting the eye or optic nerve characterised by elevated β-amyloid levels or β-amyloid deposits, including age related macular degeneration, glaucoma type diseases and β-amyloid dependent cataract formation, with antigen binding proteins that bind β-amyloid peptide, particularly human β-amyloid peptide. Other aspects of the present invention will be apparent from the description below.

BACKGROUND OF THE INVENTION

Alzheimer's disease (AD) is the most common cause of age-related cognitive decline, affecting greater than 12 million individuals worldwide (Citron M (2002) Nat. Neurosci 5, Suppl 1055-1057). The earliest stages of the disease are characterized by a progressive loss of memory with associated cognitive decline and language and behavioural deficits. In the later stages of the disease, patients develop global amnesia and have greatly reduced motor function. Death typically occurs 9 years following diagnosis and is often associated with other conditions, typically pneumonia (Davis K. L. and Samules S. C. (1998) in Pharmacological Management of Neurological and Psychiatric Disorders eds Enna S. J. and Coyle J. T. (McGraw-Hill, New York pp 267-316)). Current therapies represent symptomatic approaches, focussing on alleviating the cognitive impairment and ameliorating the behavioural symptoms associated with the progressing disease etiology. In practice these treatments provide only a short lived cognitive benefit with the level of cognitive impairment reported only to last up to 2 years. The potential for a disease-modifying therapy that slows and possibly halts the progression of the disease is enormous. Such approaches would provide radical and sustained improvements to the quality of life of patients and importantly their careers as well as reducing the huge overall healthcare costs of this disease.

Clinical diagnosis of Alzheimer's disease is currently based upon a combination of physical and mental tests which lead to a diagnosis of possible or probable Alzheimer's disease although diagnostic biomarkers and imaging are under investigation (Sonnen et al. (2007) Expert Rev Neurotherapeutics 7(8): 1021-1028; Lockhart et al (2007) Brain 130: 2607-2615). At post mortem the disease is confirmed by well characterised neurological hallmarks in the brain, which include the deposition of Aβ in parenchymal plaques and cerebral vessels, intraneuronal formation of neurofibrillary tangles, synaptic loss and loss of neuronal subpopulations in specific brain regions (Terry, R D (1991) J Neural Trans Suppl 53: 141-145).

A plethora of genetic, histological and functional evidence suggests that the β-amyloid peptide (Aβ) is key to the progression of Alzheimer's disease (Selkoe, D. J. (2001) Physiological Reviews 81: 741-766) although it has become less clear recently whether the actual Aβ deposits observed on post mortem examination are the true cause of the cognitive decline (Ferreira S T (2007) Life 59(4-5): 332-345). Aβ is known to be produced through the cleavage of the β-amyloid precursor protein (also known as APP) by an aspartyl protease enzyme known as BACE1 (also known as β-secretase, Asp2 or Memapsin-2) (De Strooper, B. and Konig, G. (1999) Nature 402: 471-472). In addition to the parenchymal and vascular deposition, soluble oligomeric forms of Aβ have been postulated to contribute to the onset of AD and they may affect neuronal function initially by impairing synaptic function (Lambert et. al. (1998) Proceedings of the National Academy of Science, U.S.A. 95: 6448-6453; Kayed et al (2003) Science 300:486-489; Cheng et al (2007) J Biol Chem 282(33):23818-23828; Ferreira et al (2007) Life 59:332-345). Although insoluble amyloid plaques are found early in AD and in mild cognitive impairment (MCI), the levels of soluble Aβ aggregates (sometimes referred to as oligomers or Aβ-derived diffusible ligands (ADDLs)) are also increased in these individuals, and soluble Aβ levels correlate better with neurofibrillary degeneration, and the loss of synaptic markers than do amyloid plaques (Naslund et. al. (2000) J Am Med Assoc 283: 1571-1577, Younkin, S. (2001) Nat. Med. 1: 8-19). In addition these oligomers may represent precursors on the route to fibril formation and their removal or neutralisation may prevent toxic effects and fibril formation (Ferreira ST (2007) Life 59(4-5): 332-345; Gong Y (2003) PNAS 100:10417-10422). Despite these findings the highly amyloidogenic Aβ42 and amino-terminally truncated forms Aβx-42 are the predominant species of Aβ found in both diffuse and senile plaques (Iwatsubo, T (1994) Neuron. 13:45-53, Gravina, S A (1995) J. Biol. Chem. 270:7013-7016) and the relative levels of Aβ42 appear not only to be a biomarker for AD but also a key regulator of Aβ aggregation into amyloid plaques. Aβ42 has been shown to aggregate more readily than other Aβ forms in vitro (Jarrett, J T (1993) Biochemistry. 32: 4693-4697) and as such Aβ42 has been implicated as the initiating molecule in the pathogenesis of AD (Younkin S G, (1998) J. Physiol. (Paris). 92:289-292). Although Aβ42 is usually a minor product of APP metabolism, small shifts in its production are associated with large effects on Aβ deposition and therefore it has been postulated that reduction of Aβ42 alone may be an effective way of treating AD (Younkin S G, (1998) J. Physiol. (Paris). 92:289-292; Levites et al (2007) J Clin Invest. 116(1):193-201). In support of this, mutations in the amyloid precursor protein (APP) and presenilin genes have been reported to predominantly increase the relative levels of Aβ42 and therefore shortening the time to onset of Alzheimer's disease (AD) (Selkoe D. J., Podlisny M. B. (2002) Annu. Rev. Genomics Hum. Genet. 3:67-99). It should be stressed however, that the rate of amyloid deposition is also dependent on overall amyloid levels, catabolism and the efficiency of Aβ clearance from the CNS which has been shown to be negatively influenced by age and elevated amyloid levels as found in AD (Deane et al (2005) J Neurosci 25(50):11495-11503; Wang et al (2006) Drug Discovery Today 11(19/20): 931-938). In this respect it has become increasingly apparent that the transport of Aβ between the central nervous system (CNS) and plasma plays a major role in the regulation of brain amyloid levels (Shibata, et al (2000) J Clin Invest 106: 1489-1499), Aβ being rapidly transported from the CNS to plasma by transport mechanisms such as LRP-1 and Aβ being rapidly imported from the plasma to the CNS by binding to RAGE (Zlokovic B V (2004) J Neurochem 89: 807-811). Therefore active vaccination with Aβ peptides or passive administration of specific Aβ antibodies that bind peripheral Aβ and therefore alter the dynamic equilibrium between the plasma, CSF and the CNS are being developed. Indeed there are now numerous studies that have demonstrated that both these approaches can lower Aβ levels, reduce Aβ pathology and in some cases provide cognitive benefit in various transgenic models of amyloidosis. Limited studies have also been conducted in higher species (Lemere, C A (2004) Am J Pathology 165: 283-297; Gandy, S (2004) Alzheimer Dis Assoc Disord 18: 44:46).

Animal models of amyloid deposition have been generated by overexpressing mutant human transgenes in mice. Mice overexpressing single human APP transgenes typically develop cerebral plaque-like β-amyloid deposits from 12 months of age (Games D. et al., (1995) Nature 373: 523-527; Hsiao K. et al., (1996) Science 274: 99-102)), while mice carrying both mutant human APP and presenilin-1 (PS-1) transgenes typically develop cerebral plaque-like β-amyloid deposits as early as 2 months of age (Kurt M. A. et al., (2001) Exp. Neurol. 171: 59-71; McGowan E. et al., (1999) Neurolbiol. Dis. 6: 231-244). These considerable biological differences in the various transgenic mouse models used have made it difficult to compare the pharmacology and the efficiency of different approaches. There is no real consensus in the field how immunotherapies targeted at β-amyloid and its various forms actually work. It is highly likely that different antibodies with different binding properties have variable outcomes in those animal models. It seems also reasonable that antibodies may act by multiple mechanisms and that the different modes of action that have been described are not mutually exclusive (Levites et al (2007) J Clin Invest. 116(1):193-201).

The first immune therapy targeting brain amyloid in the clinic was Elan/Wyeth's AN-1792, an active vaccine. This treatment was terminated following the development of clinical signs consistent with meningoencephalitis. Subgroup analyses suggested that treatment slowed the decline of cognitive function (Nature Clin Pract Neurol (2005) 1:84-85). Post-mortem analysis of patients also showed evidence of plaque-clearance (Gilman S. et al, (2005) Neurology 64 (9) 1553-1562).

Bapineuzumab (AAB-001, Elan/Wyeth), a passive monoclonal antibody, is in development.

Other diseases or disorders characterised by elevated β-amyloid levels or β-amyloid deposits include mild cognitive impairment (Kelley B J (2007) Neurologic Clinics 25 (3), 577-609), hereditary cerebral hemorrhage with β-amyloidosis of the Dutch type, cerebral β-amyloid angiopathy and various types of degenerative dementias, such as those associated with Parkinson's disease, progressive supranuclear palsy, cortical basal degeneration and diffuse Lewis body type of Alzheimer's disease (Mollenhauer B (2007) J Neural Transm e-published 23 Feb. 2007, van Oijen, M Lancet Neurol. 2006 5:655-60), Down's syndrome (Mehta, P D (2007) J Neurol Sci. 254:22-7), Age-related macular degeneration (AMD) (Johnson L V et al (2002) PNAS USA 99: 11830-11835; Anderson D H et al (2004) Exp Eye Res 78: 243-256), "Glaucoma type" diseases (Guo L et al (2007) Proc Natl Acad Sci USA 104:13444-13449) and Aβ dependent cataract formation (Goldstein L E et al (2003) Lancet 361: 1258-1265; Li G et al (2003) Mol Vision 9: 179-183).

Age-related macular degeneration (AMD) is the leading cause of blindness in the developed world. There are two major clinical presentations of AMD. Atrophic (dry) AMD is characterised by the degeneration of retinal pigment epithelial (RPE) and neuroretina. The early stages of atrophic AMD are associated with the formation of drusen, under the RPE cell layer. Early atrophic AMD can progress to an end stage disease where the RPE degenerates completely and forms sharply demarcated areas of RPE atrophy in the region of the macula: "geographic atrophy". In this form of the disease, the degeneration of RPE results in the secondary death of macular rods and cones and in these cases this leads to the severe age-related vision loss. A proportion of AMD patients develop what can either be regarded as a different form or a further complication of the disease. Approximately 10-20% of AMD patients develop choroidal neovascularisation, (CNV). When this occurs the form of the disease is known as "wet AMD" and this can be associated with some of the most severe vision loss. In wet AMD, new choroidal vessels grow through breaks in Bruch's membrane and proliferate into and under the RPE and neuroretina. In typical cases, atrophic AMD develops in the eye before the development of the wet form, however, on infrequent occasions, the neovascular form can develop in the absence of prior development of the atrophic form. In both forms of the disease, vision loss occurs due to the death of photoreceptor cells, although in wet AMD internal bleeding from the leaky vessels formed during CNV also causes vision loss. In terms of therapy for AMD there has been some progress in developing novel treatments to address some aspects of wet AMD, in particular the reduction of leaky vessel bleeding from CNV by various molecules that inhibit either VEGF (vascular endothelial growth factor) or the VEGF receptor signalling pathway. However, currently there are no definitive means of treatment for the very prevalent atrophic form of AMD nor to prevent the progression of early dry AMD either to geographic atrophy or to wet AMD, (Petrukhin K (2007) Expert Opin Ther Targets 11: 625-639) Although the exact mechanisms that cause the production of Aβ in RPE and the exact mechanism or mechanisms by which Aβ acts to influence AMD are not completely understood, the evidence implies that clearing of Aβ by agents that bind and potentially neutralise or just remove Aβ may provide a possible route to clearing drusen in AMD, reducing complement activation in AMD, reducing RPE atrophy and potentially reducing the induction of VEGF expression in RPE and its localisation at high levels around drusen. Such therapy could therefore provide means of preventing, delaying, attenuating or reversing the loss of vision due to AMD and its progression to geographic atrophy and/or exudative AMD. This may result in decreased levels of Aβ containing drusen and/or local Aβ in the surrounding environment of the RPE and thereby interfere in both the early and later stages of AMD and treat the underlying cellular decline that causes the loss of vision.

Some recently published data has shed light on the interaction of complement proteins and amyloid beta in the generation of AMD (Wang, J. et al., (2008) J. Immunol. 181: 16651-6). Amyloid beta has been shown to bind to complement factor I, the co-factor that with factor H is responsible for the breakdown of complement protein C3 from the C3b form to its inactive form, iC3b, (Wang, J. et al., 2008). The results from the recently published in vitro study were suggested to support a hypothesis where amyloid beta activates the complement system within drusen by blocking the function of complement factor I leading to a low-grade, chronic inflammation in sub-retinal tissues; thus linking four of the factors associated with the development of AMD: inflammation, complement activation, amyloid beta deposition and drusen, (Wang, J. et al., 2008). Such direct evidence for the effect of amyloid beta in activating the alternative complement pathway by potentially competing with complement factor H for binding to complement factor I has not previously been documented, (Wang, J. et al., 2008).

"Glaucoma type diseases" is a term used for a group of diseases that can lead to damage to the eye's optic nerve and result in blindness. It is a major cause of blindness in the world caused ultimately by increased intraocular pressure (IOP) and decreased visual acuity. The link between IOP and how this leads to apoptosis of the retinal ganglion cells (RGC) is not well understood. High IOP alone can induce apoptosis (Cordeiro M F et al (2004) Proc Natl Acad Sci USA 101: 13352-13356; Quigley H A et al (1995) Invest Ophtalmol Visual Sci 36:774-786) but in itself is not the only cause of cell death of the optic neurons. In addition it has been observed that the vision can continue to deteriorate even after the normalisation of the IOP following treatment with eye pressure lowering agents (Oliver J E et al (2002) Am J Ophthamol 133:764-772).

Recently there have been reports linking the potentially cytotoxic effects of β-amyloid to apoptosis of RGCs in glaucoma (McKinnon S J et al (2002) Invest Ophtamol Visual Sci 43:1077-1087). In animal models of glaucoma it has been demonstrated that caspase-3 protease is activated in RGCs which leads to abnormal processing of amyloid precursor protein (APP) by caspase-3 generating potentially toxic fragments of APP including β-amyloid (McKinnon et al (2002); Cheung Z H et al (2004) Mol Cell Neurosci 25:383-393). Amongst other cells, RGCs have been shown to express APP and this therefore appears a plausible source of β-amyloid. Both elevated levels of APP and elevated levels of β-amyloid have been implicated with activating caspase-3 although this has been observed primarily in in vitro systems. It is unclear whether APP levels in the RGCs are also increased in glaucoma thus contributing to the generation of even more β-amyloid in a positive feed back mechanism. Even more recently, the involvement of β-amyloid with apoptosis of RGCs in a rat model of glaucoma has been suggested (Guo et al (2007)). Several agents targeting β-amyloid or β-amyloid production were tested and showed a reduction of retinal ganglion cell death in vivo with a possible mild enhancement effect when all three treatments were used together. The largest effect was seen by using an anti-β-amyloid antibody which almost matched the effects seen with all three agents together.

Although the exact mechanisms that cause the production of β-amyloid in RGCs and the connection with IOP are not completely understood, the evidence implies that clearing of β-amyloid by agents that bind and potentially neutralise or just remove β-amyloid may provide a possible route to preventing RGC apoptosis in glaucoma and therefore provide means of delaying, attenuating or reversing the loss of vision in glaucoma. This may result in decreased levels of β-amyloid in the RGCs and surrounding environment and thereby address the underlying cellular decline that causes the loss of vision.

β-Amyloid may play a role in other ocular diseases and has been associated with the formation of supra-nuclear cataracts especially in those seen in AD patients and the components of the Aβ generation and processing pathway are present in the lens (Goldstein L E, et al., 2003); Li G, et al., 2003)). The therapeutic approaches described for intervention in AMD and glaucoma-type diseases may therefore be applicable to the prevention of Aβ dependent cataract formation.

WO 2008/110885 relates to methods of treating ophthalmic diseases with inhibitors directed against amyloid-β peptide. Specifically, antibody 6G which binds to an epitope on Aβ1-40 that seems to include 25-34 and 40 is disclosed.

SUMMARY OF THE INVENTION

In an aspect of the present invention there is provided a therapeutic antigen binding protein which recognises an epitope of β-amyloid peptide that contains residues 28-35 of β-amyloid.

In a particular embodiment the therapeutic antigen binding protein recognises an epitope of β-amyloid peptide that contains residues 28-34 of β-amyloid.

In a more particular embodiment the therapeutic antigen binding protein recognises an epitope of β-amyloid peptide that contains residues 28-33 of β-amyloid.

In another embodiment of the invention a therapeutic antigen binding protein which recognises an epitope of β-amyloid peptide that is within the region of residues 28-35 of β-amyloid is provided.

In another embodiment of the invention a therapeutic antigen binding protein which recognises an epitope of β-amyloid peptide that consists of residues 28-33, 28-34 or 28-35 of β-amyloid is provided.

In an embodiment of the invention a therapeutic antigen binding protein which requires residues 32 and 33 of β-amyloid for binding is provided.

In an embodiment of the invention, the therapeutic antigen binding protein is an antibody or antigen binding fragment and/or derivative thereof.

In an embodiment of the present invention there is provided a therapeutic antigen binding protein, which is an antigen binding protein, such as an antibody or antigen binding fragment and/or derivative thereof, which binds β-amyloid peptide and which comprises the following CDRs:

| CDRH1: | VYYVH | (SEQ ID No: 1) |
|---|---|---|
| CDRH2: | RIDPENGETIYTPKFQD | (SEQ ID No: 2) |
| CDRH3: | SGY | (SEQ ID No: 3) |
| CDRL1: | RSSKSLLHRNGITYLY | (SEQ ID No: 4) |
| CDRL2: | QMSNLAS | (SEQ ID No: 5) |
| CDRL3: | AQNLELWT | (SEQ ID No: 6) |

In another embodiment of the invention there is provided an antigen binding protein, such as an antibody or antigen binding fragment thereof which specifically binds H-amyloid peptide and comprises CDR's which are variants of the sequences set forth above.

A CDR variant includes a partial alteration of the CDR amino acid sequence by deletion or substitution of one to several amino acids of the CDR, or by addition or insertion of one to several amino acids to the CDR, or by a combination thereof. The CDR variant may contain 1, 2, 3, 4, 5 or 6 amino acid substitutions, additions or deletions in the amino acid sequence of the CDR. The CDR variant may contain 1, 2 or 3 amino acid substitutions, insertions or deletions in the amino acid sequence of the CDR. The substitutions in amino acid residues may be conservative substitutions, for example, substituting one hydrophobic amino acid for an alternative hydrophobic amino acid. For example leucine may be substituted with valine, or isoleucine.

Antigen binding proteins which comprise a variant CDR will have the same or similar functional properties to those comprising the CDRs discussed above. Therefore, antigen binding proteins which comprise a variant CDR will bind to the same target protein or epitope with the same or similar binding affinity to the CDR described herein.

An exemplary antibody is 6F6 murine monoclonal antibody. In one embodiment of the present invention there is provided a humanised or chimeric antibody comprising the above-identified CDRs of 6F6. For example, a chimeric antibody may comprise the variable regions of the 6F6 murine antibody, namely SEQ ID No:19 ($V_H$) and SEQ ID No:21 ($V_L$). An example of a humanised antibody based on murine 6F6 is an antibody comprising a heavy chain having SEQ ID No:27 and a light chain having SEQ ID No:28.

Throughout this specification, the terms "CDR", "CDRL1", "CDRL2", "CDRL3", "CDRH1", "CDRH2", "CDRH3" follow the Kabat numbering system as set forth in Kabat et al; *Sequences of proteins of Immunological Interest* NIH, 1987. Therefore the following defines the CDRs according to the invention:

| CDR: | Residues |
| --- | --- |
| CDRH1: | 31-35 |
| CDRH2: | 50-65 |
| CDRH3: | 95-97 |
| CDRL1: | 24-34 |
| CDRL2: | 50-56 |
| CDRL3: | 89-97 |

IGHV1-24 (SEQ ID No:13) is a human germ line sequence that is a suitable acceptor framework for grafting the $V_H$ CDRs. In a particular aspect the human acceptor heavy chain framework is derived from IGHV1-24. In alternative embodiments of the present invention, the human acceptor framework comprises a human heavy variable region sequence that has at least 90%, 95%, 96%, 97%, 98% or 99% sequence identity to the murine 6F6 heavy variable sequence over its entire length (excluding the CDR sequences).

For amino acid and nucleic acid sequences, the term "identical" or "sequence identity" indicates the degree of identity between two amino acid or two nucleic acid sequences when optimally aligned and compared with appropriate insertions or deletions. Alternatively, substantial identity exists when the DNA segments will hybridize under selective hybridization conditions, to the complement of the strand. The percent identity between two sequences is a function of the number of identical positions shared by the sequences (i.e., % identity=number of identical positions/total number of positions times 100), taking into account the number of gaps, and the length of each gap, which need to be introduced for optimal alignment of the two sequences. The comparison of sequences and determination of percent identity between two sequences can be accomplished using a mathematical algorithm, as described below.

The percent identity between two nucleotide sequences can be determined using the GAP program in the GCG software package, using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

By way of example, a polynucleotide sequence may be identical to a reference polynucleotide sequence as described, that is be 100% identical, or it may include up to a certain integer number of nucleotide alterations as compared to the reference sequence, such as at least 50, 60, 70, 75, 80, 85, 90, 95, 96, 97, 98, or 99% identical. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in the reference polynucleotide sequence by the numerical percent of the respective percent identity (divided by 100) and subtracting that product from said total number of nucleotides in the reference polynucleotide sequence or:

$$n_n \leq x_n - (x_n \cdot y),$$

wherein $n_n$ is the number of nucleotide alterations, $x_n$ is the total number of nucleotides in the reference polynucleotide sequence and y is 0.50 for 50%, 0.60 for 60%, 0.70 for 70%, 0.75 for 75%, 0.80 for 80%, 0.85 for 85%, 0.90 for 90%, 0.95 for 95%, 0.98 for 98%, 0.99 for 99% or 1.00 for 100%, · is the symbol for the multiplication operator, and wherein any non-integer product of $x_n$ and y is rounded down to the nearest integer prior to subtracting it from $x_n$.

Similarly, a polypeptide sequence may be identical to a polypeptide reference sequence as described herein, that is be 100% identical, or it may include up to a certain integer number of amino acid alterations as compared to the reference sequence such that the % identity is less than 100%, such as at least 50, 60, 70, 75, 80, 85, 90, 95, 96, 97, 98, or 99% identical. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the polypeptide sequence encoded by the polypeptide reference sequence as described herein by the numerical percent of the respective percent identity (divided by 100) and then subtracting that product from said total number of amino acids in the polypeptide reference sequence or:

$$n_a \leq x_a - (x_a \cdot Y),$$

wherein $n_a$ is the number of amino acid alterations, $x_a$ is the total number of amino acids in the polypeptide sequence, and y is, 0.50 for 50%, 0.60 for 60%, 0.70 for 70%, 0.75 for 75%, 0.80 for 80%, 0.85 for 85%, 0.90 for 90%, 0.95 for 95%, 0.98 for 98%, 0.99 for 99%, or 1.00 for 100%, · is the symbol for the multiplication operator, and wherein any non-integer product of xa and y is rounded down to the nearest integer prior to subtracting it from xa.

The % identity may be across the length of the sequence.

In order to construct a complete V-region a framework 4 has to be added to the germline encoded V-gene IGHV1-24.

Suitable framework 4 sequences include that encoded by the human JH4 minigene (Kabat):

YFDYWGQGTLVTVSS        (SEQ ID No: 15)

The skilled person appreciates that a germline V gene and a J gene do not include coding sequence for the entirety of heavy chain CDR3. However, in the antibodies of the invention, the entire heavy chain CDR3 is provided by the donor immunoglobulin. Accordingly, the combination of a VH gene such as IGHV1-24, a JH minigene such as JH4, and a set of heavy chain CDRs, such as SEQ ID No:1, SEQ ID No:2 and SEQ ID No:3 (assembled in a manner so as to mimic a mature, fully rearranged heavy chain variable region) is sufficient to define a heavy chain variable region of the invention.

IGKV2-28 (SEQ ID No:16) is a human germ line sequence is a suitable acceptor frame work for grafting the $V_L$ CDRs. In a particular aspect the human acceptor light chain framework is derived from IGKV2-28. In alternative embodiments of the present invention, the human acceptor framework comprises a human light variable region sequence that has at least 90%, 95%, 96%, 97%, 98% or 99% sequence identity to the murine 6F6 light variable sequence over its entire length (excluding the CDR sequences).

In order to construct a complete V-region a framework 4 has to be added to the germline encoded V-gene IGKV2-28. Suitable framework 4 sequences include that encoded by the human JK-1 minigene (Kabat):

WTFGQGTKVEIK        (SEQ ID No: 18)

The skilled person appreciates that a germline V gene and a J gene do not include coding sequence for the entirety of light chain CDR3. However, in the antibodies of the invention, the CDR3 sequence is provided by the donor immunoglobulin. The first two residues of the JK-1 minigene residues fall within the CDR3 region. For the JK-1 minigene these residues are identical to the last two residues in light chain CDRL3 (SEQ ID No:6). Accordingly, the combination of a $V_L$ gene such as IGKV2-28, a FR4 such as JK-1, and a set of light chain CDRs, such as SEQ ID No:4, SEQ ID No:5 and SEQ ID No:6 (assembled in a manner so as to mimic a mature, fully rearranged light chain variable region) is sufficient to define a light chain variable region of the invention.

In a particular embodiment of the invention the human acceptor heavy chain framework is derived from IGHV1-24 and the JH4 minigene and the human acceptor light chain framework is derived from IGKV2-28 and JK-1 minigene optionally containing one or more substitutions of amino acid residues based on the corresponding residues found in the donor $V_H$ domain having the sequence: SEQ ID No:19 and $V_L$ domain having the sequence: SEQ ID No:21 that maintain all or substantially all of the binding affinity of the donor antibody for β-amyloid peptide. By 'substantially all of the binding affinity' is meant that the therapeutic antibody has at most a five-fold, more particularly two-fold, reduction in binding affinity compared to the donor antibody.

In a more particular embodiment of the invention the human acceptor heavy chain framework derived from IGHV1-24 and JH4 has one or more, such as one to fifteen, more particularly two to fifteen, amino acid residue substitutions selected from the following residues (or conservative substitutions thereof):

| Kabat Numbering of residue | Human Framework Residue (donor IGHV1-24) | Corresponding residue in murine 6F6 |
|---|---|---|
| 1 | Q | E |
| 5 | V | Q |
| 13 | K | E |
| 24 | V | G |
| 27 | Y | F |
| 28 | T | N |
| 29 | L | I |
| 30 | T | K |
| 37 | V | L |
| 40 | A | L |
| 41 | P | T |
| 48 | M | I |
| 66 | R | K |
| 67 | V | A |
| 69 | M | L |
| 71 | E | V |
| 75 | T | S |
| 76 | D | N |
| 93 | A | V |
| 94 | T | S |

In a more particular embodiment the human acceptor heavy chain framework derived from IGHV1-24 and JH4 comprises the following residues (or a conservative substitute thereof):

| Kabat Numbering of residue | Human Framework Residue (donor IGHV1-24) | Residue substitution |
|---|---|---|
| 13 | K | E |
| 24 | V | G |
| 27 | Y | F |
| 28 | T | N |
| 29 | L | I |
| 30 | T | K |
| 37 | V | L |
| 40 | A | L |
| 48 | M | I |
| 66 | R | K |
| 67 | V | A |
| 69 | M | L |
| 71 | E | V |
| 93 | A | V |
| 94 | T | S |

In a more particular embodiment of the invention the human acceptor light chain framework derived from IGKV2-28 and JK-1 has one or more, such as one to four, more particularly two, amino acid residue substitutions selected from the following residues (or conservative substitutions thereof):

| Kabat Numbering of residue | Human Framework Residue (donor IGHV1-24) | Residue substitution |
|---|---|---|
| 8 | P | A |
| 11 | L | N |
| 43 | S | P |
| 63 | S | T |
| 64 | G | S |
| 100 | Q (JK-1) | G |
| 104 | V (JK-1) | L |

In a more particular embodiment of the invention the human acceptor light chain framework derived from IGKV2-28 and JK-1 comprises the following residues (or a conservative substitute thereof):

| Kabat Numbering of residue | Human Framework Residue (donor IGHV1-24) | Residue substitution |
| --- | --- | --- |
| 11 | L | N |
| 64 | G | S |

In one embodiment of the invention there is provided a therapeutic antibody comprising a $V_H$ domain having the sequence set forth in SEQ ID No:24.

In one embodiment of the invention there is provided a therapeutic antibody comprising a $V_L$ domain having the sequence set forth in SEQ ID No:26.

In one embodiment of the invention there is provided a therapeutic antibody comprising a $V_H$ domain having the sequence set forth in SEQ ID No:24 and a $V_L$ domain having the sequence set forth in SEQ ID No:26.

In one embodiment of the invention there is provided a therapeutic antibody comprising a $V_H$ domain having the sequence set forth in SEQ ID No:59 and a $V_L$ domain having the sequence set forth in SEQ ID No:67.

In one embodiment of the invention there is provided a therapeutic antibody comprising a $V_H$ domain having the sequence set forth in SEQ ID No:61 and a $V_L$ domain having the sequence set forth in SEQ ID No:67.

In one embodiment of the invention there is provided a therapeutic antibody comprising a $V_H$ domain having the sequence set forth in SEQ ID No:63 and a $V_L$ domain having the sequence set forth in SEQ ID No:67.

In one embodiment of the invention there is provided a therapeutic antibody comprising a $V_H$ domain having the sequence set forth in SEQ ID No:65 and a $V_L$ domain having the sequence set forth in SEQ ID No:67.

In one embodiment of the invention there is provided a therapeutic antibody comprising a $V_H$ domain having the sequence set forth in SEQ ID No:59 and a $V_L$ domain having the sequence set forth in SEQ ID No:69.

In one embodiment of the invention there is provided a therapeutic antibody comprising a $V_H$ domain having the sequence set forth in SEQ ID No:61 and a $V_L$ domain having the sequence set forth in SEQ ID No:69.

In one embodiment of the invention there is provided a therapeutic antibody comprising a $V_H$ domain having the sequence set forth in SEQ ID No:63 and a $V_L$ domain having the sequence set forth in SEQ ID No:69.

In one embodiment of the invention there is provided a therapeutic antibody comprising a $V_H$ domain having the sequence set forth in SEQ ID No:65 and a $V_L$ domain having the sequence set forth in SEQ ID No:69.

In one embodiment of the invention there is provided a therapeutic antibody comprising a $V_H$ domain having the sequence set forth in SEQ ID No:59 and a $V_L$ domain having the sequence set forth in SEQ ID No:71.

In one embodiment of the invention there is provided a therapeutic antibody comprising a $V_H$ domain having the sequence set forth in SEQ ID No:61 and a $V_L$ domain having the sequence set forth in SEQ ID No:71.

In one embodiment of the invention there is provided a therapeutic antibody comprising a $V_H$ domain having the sequence set forth in SEQ ID No:63 and a $V_L$ domain having the sequence set forth in SEQ ID No:71.

In one embodiment of the invention there is provided a therapeutic antibody comprising a $V_H$ domain having the sequence set forth in SEQ ID No:65 and a $V_L$ domain having the sequence set forth in SEQ ID No:71.

The antibody heavy chain variable region may have at least 90%, 95%, 96%, 97%, 98%, 99% or 100% identity to any one of SEQ ID NO:24, 59, 61, 63, or 65. The antibody light chain variable region may have at least 90%, 95%, 96%, 97%, 98%, 99% or 100% identity to any one of SEQ ID NO:26, 67, 69, or 71.

In one embodiment of the invention there is provided a therapeutic antibody, which antibody comprises a heavy chain having the sequence set forth in SEQ ID No:27.

In one embodiment of the invention there is provided a therapeutic antibody, which antibody comprises a light chain having the sequence set forth in SEQ ID No:28.

In one embodiment of the invention there is provided a therapeutic antibody, which antibody comprises a heavy chain having the sequence set forth in SEQ ID No:27 and a light chain having the sequence set forth in SEQ ID No:28.

Any of the heavy chain variable regions may be combined with a suitable human constant region. Any of the light chain variable regions may be combined with a suitable constant region.

In a particular embodiment the therapeutic antigen binding protein of the present invention is an antibody or fragment and/or derivative thereof that essentially lacks the functions of a) activation of complement by the classical pathway; and b) mediating antibody-dependent cellular cytotoxicity.

In another aspect of the invention there is provided a pharmaceutical composition comprising a therapeutic antigen binding protein or a therapeutic antibody according to the invention.

In a further aspect of the invention there is provided a method of treating a human patient afflicted with a β-amyloid peptide-related disease which method comprises the step of administering to said patient a therapeutically effective amount of a therapeutic antigen binding protein or therapeutic antibody according to the invention.

In an embodiment of the invention the β-amyloid peptide-related disease is Alzheimer's disease. In another embodiment of the invention the β-amyloid peptide-related disease is a disease or disorder affecting the eye or optic nerve characterised by elevated β-amyloid levels or β-amyloid deposits. Specifically, the β-amyloid peptide-related disease may be age-related macular degeneration (AMD), glaucoma or β-amyloid dependent cataract formation.

In another embodiment of the invention, the therapeutic antigen binding protein is administered in combination with an inhibitor of the complement pathway, especially the alternative complement pathway, for example, but not excluding other anti-complement approaches: complement factor H (CFH) or fragments thereof, soluble Complement Receptor 1, (sCR1) or fragments thereof, soluble membrane co-factor protein (MCP) and fragments thereof, soluble decay accelerating factor (DAF) and fragments thereof. In this context, a complement pathway inhibitor is a molecule that acts to negatively regulate the activity of a complement pathway, especially the alternative complement pathway.

In a further embodiment of the invention, the therapeutic antigen binding protein is administered in combination with an inhibitor of a complement pathway activator, especially an inhibitor of an alternative complement pathway activator, for example, but not excluding other inhibitory approaches or other complement pathway targets: an antibody or antibody fragment, for example a domain antibody, to neutralise complement factor D (CFD) or complement factor B (CFB) activity. The 13-residue peptide inhibitor of complement component C3, compstatin, and the anti-C5a complement component antibody, pexelizumab, are also considered to be inhibitors of complement pathway activators within the context of the invention. In general, an inhibitor of a complement pathway activator is an agent that inhibits or antagonises, to some extent, a biological activity of a given complement activator such that the effect would be to negatively regulate the activity of a complement pathway, especially the alternative complement pathway.

Complement-targeted therapeutic approaches have been recently reviewed (Ricklin, D & Lambris, J. (2007) Nature Biotechnology 25:1265-75, incorporated herein by reference in its entirety) and the anti-complement pathway approaches described therein could all potentially be used in combination with an anti-amyloid beta antibody to provide a therapeutic approach. The anti-complement approaches considered include: (i) protease inhibitors, eg. Complement factor D inhibitors, (ii) soluble complement regulators, eg. soluble truncated complement receptor 1, (iii) therapeutic antibodies, e.g. against complement factor D or B, (iv) complement component inhibitors, e.g. C5 inhibitor, and (v) receptor antagonists, e.g. small molecule C5a receptor antagonists.

The complement pathway inhibitor, or the inhibitor of a complement pathway activator, may be administered simultaneously with the therapeutic antigen binding protein of the invention, or sequentially, separately or in a staggered manner.

A pharmaceutical composition comprising a therapeutic antigen binding protein as defined herein and a complement pathway inhibitor or an inhibitor of a complement pathway activator, is also provided.

Use of a therapeutic antigen binding protein or a therapeutic antibody according to the invention in the manufacture of a medicament for the treatment of a β-amyloid peptide-related disease is also provided.

A bispecific antibody or bispecific fragment thereof having a first specificity towards β-amyloid, such as an epitope of β-amyloid peptide that contains residues 28-35 of β-amyloid as described above, and a second specificity towards an activator of the complement pathway, is also provided.

An antigen binding protein of the invention, an antibody of the invention, or a bispecific antibody or bispecific fragment thereof of the invention, for use in treating a β-amyloid peptide-related disease is also provided.

In another embodiment of the invention there is provided an antibody or a fragment thereof comprising a murine $V_H$ domain having the sequence: SEQ ID No:19 and a murine $V_L$ domain having the sequence: SEQ ID No:21.

In another embodiment of the invention there is provided a polynucleotide encoding an antibody heavy chain or a fragment thereof comprising a $V_H$ domain having the sequence SEQ ID No:19, in particular the polynucleotide of SEQ ID No:20.

In another embodiment of the invention there is provided a polynucleotide encoding an antibody light chain or a fragment thereof comprising a $V_L$ domain having the sequence SEQ ID No:21, in particular the polynucleotide of SEQ ID No:22.

In an aspect of the present invention there is provided an antigen binding protein that competes with an antibody comprising a heavy chain having the sequence set forth in SEQ ID No:27 and a light chain having the sequence set forth in SEQ ID No:28 for binding to β-amyloid in an ELISA assay.

The person skilled in the art appreciates that in order for an antigen binding protein (antigen binding protein A) to compete with an antibody comprising a heavy chain having the sequence set forth in SEQ ID No:27 and a light chain having the sequence set forth in SEQ ID No:28 (antibody B) for a specific binding site β-amyloid), antigen binding protein A must be present in a sufficient amount to have an effect in said assay. In a particular embodiment, antigen binding protein A and antibody B are present in equimolar amounts. In another embodiment, the presence of antigen binding protein A reduces the binding of antibody B to β-amyloid in an ELISA assay by more than 10%, 20%, 30%, 40% or 50%. In another embodiment β-amyloid is bound to an immunoassay plate in an ELISA assay. In another embodiment antigen binding protein A reduces the binding of antibody B to plate bound β-amyloid, whereas a non-β-amyloid-specific control does not.

In a further aspect of the invention the antigen binding protein is a therapeutic antibody that comprises heavy and light chains comprising polypeptides which are at least 90%, 95%, 96%, 97%, 98% or 99% identical to the amino acid sequences of SEQ ID No:27 and SEQ ID No:28, respectively, wherein said antibody binds β-amyloid. In a preferred embodiment, the antibody recognises an epitope of β-amyloid peptide that contains residues 28-35 of β-amyloid.

In another aspect of the invention, there is provided an antigen binding protein which binds to a C-terminal biotinylated β-amyloid peptide that comprises residues 24-35 (SEQ ID No:10) or 28-39 (SEQ ID No:11) of β-amyloid as determined by surface plasmon resonance, said peptide being bound to a streptavidin sensor chip.

In a further aspect of the invention, there is provided an antigen binding protein, specifically a monoclonal antibody or fragment thereof, which specifically binds to β-amyloid and requires at least one residue in the 28-35 region of β-amyloid for binding. In a preferred embodiment, the antigen binding protein additionally requires at least one flanking residue or structurally neighbouring residue to said at least one residue in the 28-35 region of β-amyloid for binding. Accordingly, the antigen binding protein may independently require one, two, three, four, five or more of residues selected from the group consisting of 28, 29, 30, 31, 32, 33, 34 and 35 of β-amyloid, and flanking or structurally neighbouring residues.

The person skilled in the art can readily identify such antigen binding proteins using, for example, alanine replacement scanning in ELISA assays. In this respect, whether or not the antigen binding protein requires a residue in the 28-35 region of β-amyloid, or a flanking or structurally neighbouring residue, for binding can be determined by independently substituting said residue of β-amyloid with alanine and comparing the binding affinity of the antigen binding protein to the alanine substituted β-amyloid peptide with the binding affinity of the antigen binding protein to the wild type β-amyloid. Whether or not a residue in the 28-35 region of β-amyloid is required is defined by a reduction in binding affinity of the antigen binding protein to the alanine substituted β-amyloid peptide compared with the wild-type β-amyloid peptide, wherein said reduction is more than 1, 2, 3, 4 or 5 fold as determined by Biacore or ELISA affinity measurements.

Further, a structurally neighbouring residue in this context is a residue that is in close proximity in three-dimensional space to the residue in question and which is bound by the antigen binding protein. The person skilled in the art appreciates that antigen epitopes may be either linear or non-linear peptide sequences. In the latter, non-linear case, although the residues are from different regions of the peptide chain, they may be in close proximity in the three dimensional structure of the antigen. Such structurally neighbouring residues can be determined through computer modelling programs or via three-dimensional structures obtained through methods known in the art, such as X-ray crystallography.

In another aspect of the invention there is provided a process for producing an antibody according to the invention, which process comprises expressing polynucleotide encoding the antibody in a host cell.

In another aspect of the invention there is provided a polynucleotide encoding a therapeutic antibody heavy chain comprising a $V_H$ chain having the sequence set forth in SEQ ID No:24.

In another aspect of the invention there is provided a polynucleotide encoding a therapeutic antibody light chain comprising a $V_L$ domain having the sequence set forth in SEQ ID No:26.

In another aspect of the invention there is provided a polynucleotide encoding a therapeutic antibody heavy chain having the sequence set forth in SEQ ID No:27.

In another aspect of the invention there is provided a polynucleotide encoding a therapeutic antibody light chain having the sequence set forth in SEQ ID No:28.

In a more particular embodiment of the invention there is provided a polynucleotide encoding a therapeutic antibody heavy chain, which polynucleotide comprises the sequence set forth in SEQ ID No:29.

In another more particular embodiment of the invention there is provided a polynucleotide encoding a therapeutic antibody light chain, which polynucleotide comprises the sequence set forth in SEQ ID No:30.

DETAILED DESCRIPTION OF THE INVENTION

1. Antigen Binding Proteins

Figure 1:
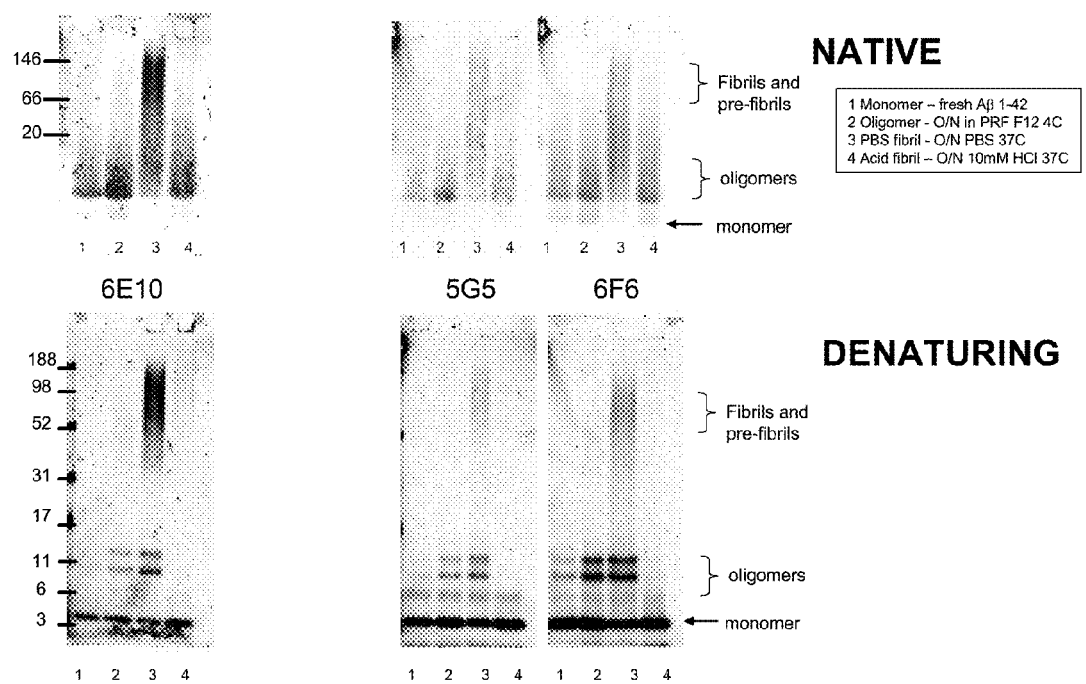
FIG. 1 shows a Western blot detection of various forms of beta amyloid using 6F6 antibody or 6E10 (antibody specific for human Aβ 1-16; commercial reagent, Eurogentec) and 5G5 (antibody specific for Aβ1-42; in house reagent).

The term "antigen binding protein" as used herein refers to antibodies, antibody fragments and other protein constructs, such as domains, specifically those which are capable of binding to β-amyloid, as discussed further below.

1.1 Intact Antibodies

The antigen binding proteins of the present invention may be "intact antibodies". An antigen binding protein of the invention includes a therapeutic antibody which is an antibody or antigen binding fragment and/or derivative thereof. Intact antibodies are usually heteromultimeric glycoproteins comprising at least two heavy and two light chains. Aside from IgM, intact antibodies are heterotetrameric glycoproteins of approximately 150 KDa, composed of two identical light (L) chains and two identical heavy (H) chains. Typically, each light chain is linked to a heavy chain by one covalent disulfide bond while the number of disulfide linkages between the heavy chains of different immunoglobulin isotypes varies. Each heavy and light chain also has intrachain disulfide bridges. Each heavy chain has at one end a variable domain ($V_H$) followed by a number of constant regions. Each light chain has a variable domain ($V_L$) and a constant region at its other end; the constant region of the light chain is aligned with the first constant region of the heavy chain and the light chain variable domain is aligned with the variable domain of the heavy chain. The light chains of antibodies from most vertebrate species can be assigned to one of two types called Kappa and Lambda based on the amino acid sequence of the constant region. Depending on the amino acid sequence of the constant region of their heavy chains, human antibodies can be assigned to five different classes, IgA, IgD, IgE, IgG and IgM. IgG and IgA can be further subdivided into subclasses, IgG1, IgG2, IgG3 and IgG4; and IgA1 and IgA2. Species variants exist with mouse and rat having at least IgG2a, IgG2b. The variable domain of the antibody confers binding specificity upon the antibody with certain regions displaying particular variability called complementarity determining regions (CDRs). The more conserved portions of the variable region are called framework regions (FR). The variable domains of intact heavy and light chains each comprise four FR connected by three CDRs. The CDRs in each chain are held together in close proximity by the FR regions and with the CDRs from the other chain contribute to the formation of the antigen binding site of antibodies. The constant regions are not directly involved in the binding of the antibody to the antigen but exhibit various effector functions such as participation in antibody dependent cell-mediated cytotoxicity (ADCC), phagocytosis via binding to Fcγ receptor, half-life/clearance rate via neonatal Fc receptor (FcRn) and complement dependent cytotoxicity via the C1q component of the complement cascade. The human IgG2 constant region has been reported to essentially lack the ability to activate complement by the classical pathway or to mediate antibody-dependent cellular cytotoxicity. The IgG4 constant region has been reported to lack the ability to activate complement by the classical pathway and mediates antibody-dependent cellular cytotoxicity only weakly. Antibodies essentially lacking these effector functions may be termed 'non-lytic' antibodies.

1.1.1 Human Antibodies

The antigen binding proteins of the present invention may be human antibodies. Human antibodies may be produced by a number of methods known to those of skill in the art. Human antibodies can be made by the hybridoma method using human myeloma or mouse-human heteromyeloma cell lines see Kozbor J. Immunol 133, 3001, (1984) and Brodeur, Monoclonal Antibody Production Techniques and Applications, pp 51-63 (Marcel Dekker Inc, 1987). Alternative methods include the use of phage libraries or transgenic mice both of which utilize human V region repertoires (see Winter G, (1994), Annu. Rev. Immunol 12, 433-455, Green L L (1999), J. Immunol. methods 231, 11-23).

Several strains of transgenic mice are now available wherein their mouse immunoglobulin loci has been replaced with human immunoglobulin gene segments (see Tomizuka K, (2000) PNAS 97, 722-727; Fishwild D. M (1996) Nature Biotechnol. 14, 845-851, Mendez M J, 1997, Nature Genetics, 15, 146-156). Upon antigen challenge such mice are capable of producing a repertoire of human antibodies from which antibodies of interest can be selected.

Of particular note is the Trimera™ system (see Eren R et al, (1998) Immunology 93:154-161) where human lymphocytes are transplanted into irradiated mice, the Selected Lymphocyte Antibody System (SLAM, see Babcook et al, PNAS (1996) 93:7843-7848) where human (or other species) lymphocytes are effectively put through a massive pooled in vitro antibody generation procedure followed by deconvulated, limiting dilution and selection procedure and the Xenomouse II™ (Abgenix Inc). An alternative approach is available from Morphotek Inc using the Morphodoma™ technology.

Phage display technology can be used to produce human antibodies (and fragments thereof), see McCafferty; Nature, 348, 552-553 (1990) and Griffiths A D et al (1994) EMBO 13:3245-3260. According to this technique antibody V domain genes are cloned in frame into either a major or minor coat of protein gene of a filamentous bacteriophage such as M13 or fd and displayed (usually with the aid of a helper phage) as functional antibody fragments on the surface of the phage particle. Selections based on the functional properties of the antibody result in selection of the gene encoding the antibody exhibiting those properties. The phage display technique can be used to select antigen specific antibodies from libraries made from human B cells taken from individuals afflicted with a disease or disorder described above or alternatively from unimmunized human donors (see Marks; J. Mol. Biol. 222,581-597, 1991). Where an intact human antibody is desired comprising an Fc domain it is necessary to reclone the phage displayed derived fragment into a mammalian expression vector comprising the desired constant regions and establishing stable expressing cell lines.

The technique of affinity maturation may be used to improve binding affinity. This may for example be achieved by sequentially replacing the H and L chain V regions with naturally occurring variants and selecting on the basis of improved binding affinities (Marks; Bio/technol 10, 779-783 (1992). Variants of this technique such as "epitope imprinting" are now also available (WO 93/06213, Waterhouse; Nucl. Acids Res 21, 2265-2266 (1993)). More recently affinity matured antibodies have been obtained by random mutagenesis of the V regions or CDRs for example by using error prone RNA replicases and subsequent selection from these libraries by ribosome display selection techniques (Kopsidas G BMC Biotechnology. 7:18, 2007).

1.1.2 Chimeric and Humanised Antibodies

The antigen binding proteins of the present invention may be "chimeric" or "humanised" antibodies. The use of intact non-human antibodies in the treatment of human diseases or disorders carries with it the now well established problems of potential immunogenicity especially upon repeated administration of the antibody: that is the immune system of the patient may recognise the non-human intact antibody as nonself and mount a neutralising response. In addition to developing fully human antibodies (see above) various techniques have been developed over the years to overcome these problems and generally involve reducing the composition of nonhuman amino acid sequences in the intact therapeutic antibody whilst retaining the relative ease in obtaining nonhuman antibodies from an immunised animal e.g. mouse, rat or rabbit. Broadly two approaches have been used to achieve this. The first are chimeric antibodies, which generally comprise a non-human (e.g. rodent such as mouse) variable domain fused to a human constant region. Because the antigen-binding site of an antibody is localised within the variable regions the chimeric antibody retains its binding affinity for the antigen but acquires the effector functions of the human constant region and is therefore able to perform effector functions such as described supra. Chimeric antibodies are typically produced using recombinant DNA methods. DNA encoding the antibodies (e.g. cDNA) is isolated and sequenced using conventional procedures (e.g. by using oligonucleotide probes that are capable of binding specifically to genes encoding the H and L chain variable regions of the antibody of the invention, e.g. DNA of SEQ ID No:19 and 21 described supra). Hybridoma cells serve as a typical source of such DNA. Once isolated, the DNA is placed into expression vectors which are then transfected into host cells such as *E. Coli*, COS cells, CHO cells, PerC6 cells or myeloma cells that do not otherwise produce immunoglobulin protein to obtain synthesis of the antibody. The DNA may be modified by substituting the coding sequence for human L and H chains for the corresponding non-human (e.g. murine) H and L constant regions see e.g. Morrison; PNAS 81, 6851 (1984). Thus in another embodiment of the invention there is provided a chimeric antibody comprising a $V_H$ domain having the sequence: SEQ ID No:19 and a $V_L$ domain having the sequence: SEQ ID No:21 fused to a human constant region (which maybe of a IgG isotype e.g. IgG1).

The second approach involves the generation of humanised antibodies wherein the non-human content of the antibody is reduced by humanizing the variable regions. Two techniques for humanisation have gained popularity. The first is humanisation by CDR grafting. CDRs build loops close to the antibody's N-terminus where they form a surface mounted in a scaffold provided by the framework regions. Antigen-binding specificity of the antibody is mainly defined by the topography and by the chemical characteristics of its CDR surface. These features are in turn determined by the conformation of the individual CDRs, by the relative disposition of the CDRs, and by the nature and disposition of the side chains of the residues comprising the CDRs. A large decrease in immunogenicity can be achieved by grafting only the CDRs of a non-human (e.g. murine) antibody ("donor" antibody) onto a suitable human framework ("acceptor framework") and constant regions (see Jones et al (1986) Nature 321, 522-525 and Verhoeyen M et al (1988) Science 239, 1534-1536). However, CDR grafting per se may not result in the complete retention of antigen-binding properties and it is frequently found that some framework residues of the donor antibody need to be preserved (sometimes referred to as "backmutations") in the humanised molecule if significant antigen-binding affinity is to be recovered (see Queen C et al (1989) PNAS 86, 10,029-10,033, Co, M et al (1991) Nature 351, 501-502). In this case, human V regions showing the greatest sequence homology (typically 60% or greater) to the non-human donor antibody maybe chosen from a database in order to provide the human framework (FR). The selection of human FRs can be made either from human consensus or individual human antibodies. Where necessary key residues from the donor antibody are substituted into the human acceptor framework to preserve CDR conformations. Computer modelling of the antibody maybe used to help identify such structurally important residues, see WO99/48523.

Alternatively, humanisation maybe achieved by a process of "veneering". A statistical analysis of unique human and murine immunoglobulin heavy and light chain variable regions revealed that the precise patterns of exposed residues are different in human and murine antibodies, and most individual surface positions have a strong preference for a small number of different residues (see Padlan E. A. et al; (1991) Mol. Immunol. 28, 489-498 and Pedersen J. T. et al (1994) J. Mol. Biol. 235; 959-973). Therefore it is possible to reduce the immunogenicity of a non-human Fv by replacing exposed residues in its framework regions that differ from those usually found in human antibodies. Because protein antigenicity can be correlated with surface accessibility, replacement of the surface residues may be sufficient to render the mouse variable region "invisible" to the human immune system (see also Mark G. E. et al (1994) in *Handbook of Experimental Pharmacology vol. 113: The pharmacology of monoclonal Antibodies*, Springer-Verlag, pp 105-134). This procedure of humanisation is referred to as "veneering" because only the surface of the antibody is altered, the supporting residues remain undisturbed. Further alternative approaches include that set out in WO04/006955 and the procedure of Humaneering™ (Kalobios) which makes use of bacterial expression systems and produces antibodies that are close to human germine in sequence (Alfenito-M Advancing Protein Therapeutics January 2007, San Diego, Calif.).

It will be apparent to those skilled in the art that the term "derived" is intended to define not only the source in the sense of it being the physical origin for the material but also to define material which is structurally identical to the material but which does not originate from the reference source. Thus "residues found in the donor antibody" need not necessarily have been purified from the donor antibody.

It is well recognised in the art that certain amino acid substitutions are regarded as being "conservative". Amino acids are divided into groups based on common side-chain properties and substitutions within groups that maintain all or substantially all of the binding affinity of the therapeutic antibody of the invention are regarded as conservative substitutions, see the following Table 1:

TABLE 1

| Side chain | Members |
| --- | --- |
| Hydrophobia | met, ala, val, leu, ile |
| neutral hydrophilic | cys, ser, thr |
| Acidic | asp, glu |
| Basic | asn, gln, his, lys, arg |
| residues that influence chain orientation | gly, pro |
| aromatic | trp, tyr, phe |

1.1.3 Multi- and Bispecific Antibodies

The antigen binding proteins of the present invention may be multi-specific i.e. they may bind more than one antigen. In a particular embodiment, the antigen binding protein is a bispecific antibody. A bispecific antibody is an antibody derivative having binding specificities for at least two different epitopes and also forms part of the invention. Methods of making such antibodies are known in the art. Traditionally, the recombinant production of bispecific antibodies is based on the coexpression of two immunoglobulin H chain-L chain pairs, where the two H chains have different binding specificities see Millstein et al, Nature 305 537-539 (1983), WO93/08829 and Traunecker et al EMBO, 10, 1991, 3655-3659. Because of the random assortment of H and L chains, a potential mixture of ten different antibody structures are produced of which only one has the desired binding specificity. An alternative approach involves fusing the variable domains with the desired binding specificities to heavy chain constant region comprising at least part of the hinge region, CH2 and CH3 regions. It is preferred to have the CH1 region containing the site necessary for light chain binding present in at least one of the fusions. DNA encoding these fusions, and if desired the L chain are inserted into separate expression vectors and are then cotransfected into a suitable host organism. It is possible though to insert the coding sequences for two or all three chains into one expression vector. In one preferred approach, the bispecific antibody is composed of a H chain with a first binding specificity in one arm and a H-L chain pair, providing a second binding specificity in the other arm, see WO94/04690. See also Suresh et al Methods in Enzymology 121, 210, 1986.

Delivery of therapeutic proteins to the brain has been hampered by the presence of the blood brain barrier (BBB) and there is a similar blood retinal barrier between the eye and the bloodstream. Where it is desired to deliver an antigen binding protein of the invention, such as an antibody of the invention or antibody fragment of the invention, across a biological barrier such as the BBB various strategies have been proposed to enhance such delivery where needed and similar strategies may be applicable to allow crossing of the blood retinal barrier.

In order to obtain required nutrients and factors from the blood, the BBB possesses some specific receptors, which transport compounds from the circulating blood to the brain. Studies have indicated that some compounds like insulin (see Duffy K R et al (1989) Brain Res. 420:32-38), transferrin (see Fishman J B et al (1987) J. Neurosci 18:299-304) and insulin like growth factors 1 and 2 (see Pardridge W M (1986) Endocrine Rev. 7:314-330 and Duffy K R et al (1986) Metabolism 37:136-140) traverse the BBB via receptor-mediated transcytosis. Receptors for these molecules thus provide a potential means for therapeutic antibodies of the invention to access the brain using so-called "vectored" antibodies (see Pardridge W M (1999) Advanced Drug Delivery Review 36:299-321). For example, an antibody to transferrin receptor has been shown to be dynamically transported into the brain parenchyma (see Friden P M et al (1991) PNAS 88:4771-4775 and Friden P M et al (1993) Science 259:373-377). Thus one potential approach is to produce a bispecific antibody or bispecific fragment such as described supra wherein a first specificity is towards an epitope of β-amyloid peptide that contains residues 28-35 of β-amyloid as described above and a second specificity towards a transport receptor located at the BBB e.g. a second specificity towards the transferrin transport receptor.

Other bispecific antibodies envisaged by the present invention include a bispecific antibody or bispecific fragment thereof having a first specificity towards β-amyloid and a second specificity towards an activator of the complement pathway with the aim to inhibit its activity, for example, but not excluding others: a complement factor, such as complement factor D.

Multi-specific antigen binding proteins of the invention include proteins having a first specificity towards β-amyloid, such as an epitope of β-amyloid peptide that contains residues 28-35 of β-amyloid as described above, a second specificity towards a transport receptor located at the BBB or the blood-retinal barrier, and a third specificity towards an activator of the complement pathway.

1.2 Antibody Fragments and Other Protein Constructs, Such as Domains

In certain embodiments of the invention there is provided a therapeutic antibody which is an antigen binding fragment. Such fragments may be functional antigen binding fragments of intact and/or humanised and/or chimeric antibodies such as Fab, Fd, Fab', F(ab')$_2$, Fv, ScFv fragments of the antibodies described supra. Fragments lacking the constant region lack the ability to activate complement by the classical pathway or to mediate antibody-dependent cellular cytotoxicity. Traditionally such fragments are produced by the proteolytic digestion of intact antibodies by e.g. papain digestion (see for example, WO 94/29348) but may be produced directly from recombinantly transformed host cells. For the production of ScFv, see Bird et al; (1988) Science, 242, 423-426. In addition, antibody fragments may be produced using a variety of engineering techniques as described below.

Fv fragments appear to have lower interaction energy of their two chains than Fab fragments. To stabilise the association of the $V_H$ and $V_L$ domains, they have been linked with peptides (Bird et al, (1988) Science 242, 423-426, Huston et al, PNAS, 85, 5879-5883), disulphide bridges (Glockshuber et al, (1990) Biochemistry, 29, 1362-1367) and "knob in hole" mutations (Zhu et al (1997), Protein Sci., 6, 781-788). ScFv fragments can be produced by methods well known to those skilled in the art see Whitlow et al (1991) Methods companion Methods Enzymol, 2, 97-105 and Huston et al (1993) Int. Rev. Immunol 10, 195-217. ScFv may be produced in bacterial cells such as *E. Coli* but are more typically produced in eukaryotic cells. One disadvantage of ScFv is the monovalency of the product, which precludes an increased avidity due to polyvalent binding, and their short half-life. Attempts to overcome these problems include bivalent (ScFv')$_2$ produced from ScFV containing an additional C terminal cysteine by chemical coupling (Adams et al (1993) Can. Res 53, 4026-4034 and McCartney et al (1995) Protein Eng. 8, 301-314) or by spontaneous site-specific dimerization of ScFv containing an unpaired C terminal cysteine residue (see Kipriyanov et al (1995) Cell. Biophys 26, 187-204). Alternatively, ScFv can be forced to form multimers by shortening the peptide linker to between 3 to 12 residues to form "diabodies", see Holliger et al PNAS (1993), 90, 6444-6448. Reducing the linker still further can result in ScFV trimers ("triabodies", see Kortt et al (1997) Protein Eng, 10, 423-433) and tetramers ("tetrabodies", see Le Gall et al (1999) FEBS Lett, 453, 164-168). Construction of bivalent ScFV molecules can also be achieved by genetic fusion with protein dimerizing motifs to form "miniantibodies" (see Pack et al (1992) Biochemistry 31, 1579-1584) and "minibodies" (see Hu et al (1996), Cancer Res. 56, 3055-3061). ScFv-Sc-Fv tandems ((ScFV)$_2$) may also be produced by linking two ScFv units by a third peptide linker, see Kurucz et al (1995) J. Immol. 154, 4576-4582. Bispecific diabodies can be produced through the noncovalent association of two single chain fusion products consisting of $V_H$ domain from one antibody connected by a short linker to the $V_L$ domain of another antibody, see Kipriyanov et al (1998), Int. J. Can 77, 763-772. The stability of such bispecific diabodies can be enhanced by the introduction of disulphide bridges or "knob in hole" mutations as described supra or by the formation of single chain diabodies (ScDb) wherein two hybrid ScFv fragments are connected through a peptide linker see Kontermann et al (1999) J. Immunol. Methods 226 179-188. Tetravalent bispecific molecules are available by e.g. fusing a ScFv fragment to the CH3 domain of an IgG molecule or to a Fab fragment through the hinge region see Coloma et al (1997) Nature Biotechnol. 15, 159-163. Alternatively, tetravalent bispecific molecules have been created by the fusion of bispecific single chain diabodies (see Alt et al, (1999) FEBS Lett 454, 90-94. Smaller tetravalent bispecific molecules can also be formed by the dimerization of either ScFv-ScFv tandems with a linker containing a helix-loop-helix motif (DiBi miniantibodies, see Muller et al (1998) FEBS Lett 432, 45-49) or a single chain molecule comprising four antibody variable domains ($V_H$ and $V_L$) in an orientation preventing intramolecular pairing (tandem diabody, see Kipriyanov et al, (1999) J. Mol. Biol. 293, 41-56). Bispecific F(ab')2 fragments can be created by chemical coupling of Fab' fragments or by heterodimerization through leucine zippers (see Shalaby et al, (1992) J. Exp. Med. 175, 217-225 and Kostelny et al (1992), J. Immunol. 148, 1547-1553). Also available are isolated $V_H$ and $V_L$ domains, see U.S. Pat. No. 6,248,516; U.S. Pat. No. 6,291,158; U.S. Pat. No. 6,172,197.

The phrase "immunoglobulin single variable domain" refers to an antibody variable domain ($V_H$, $V_{HH}$, $V_L$) that specifically binds an antigen or epitope independently of a different V region or domain. An immunoglobulin single variable domain can be present in a format (e.g., homo- or hetero-multimer) with other, different variable regions or variable domains where the other regions or domains are not required for antigen binding by the single immunoglobulin variable domain (i.e., where the immunoglobulin single variable domain binds antigen independently of the additional variable domains). A "domain antibody" or "dAb" is the same as an "immunoglobulin single variable domain" which is capable of binding to an antigen as the term is used herein. An immunoglobulin single variable domain may be a human antibody variable domain, but also includes single antibody variable domains from other species such as rodent (for example, as disclosed in WO 00/29004, nurse shark and Camelid $V_{HH}$ dAbs. Camelid $V_{HH}$ are immunoglobulin single variable domain polypeptides that are derived from species including camel, llama, alpaca, dromedary, and guanaco, which produce heavy chain antibodies naturally devoid of light chains. Such $V_{HH}$ domains may be humanised according to standard techniques available in the art, and such domains are still considered to be "domain antibodies" according to the invention. As used herein "$V_H$ includes camelid $V_{HH}$ domains.

An antigen binding fragment may also be provided by means of arrangement of one or more CDRs on non-antibody protein scaffolds such as a domain. A domain can specifically bind an antigen or epitope independently of a different variable region or domain. This may be a domain antibody, as described above, or may be a domain which is a derivative of a scaffold selected from the group consisting of CTLA-4, lipocalin, SpA, an Antibody, an avimer, GroEI, transferrin, GroES and fibronectin/adnectin, which has been subjected to protein engineering in order to obtain binding to an antigen other than the natural ligand.

In this context the term "domain" refers to a folded protein structure which has tertiary structure independent of the rest of the protein. Generally, domains are responsible for discrete functional properties of proteins, and in many cases may be added, removed or transferred to other proteins without loss of function of the remainder of the protein and/or of the domain. A "single variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain.

1.3 Heteroconjugate Antibodies

Heteroconjugate antibodies are derivatives which also form an embodiment of the present invention. Heteroconjugate antibodies are composed of two covalently joined antibodies formed using any convenient cross-linking methods. See U.S. Pat. No. 4,676,980.

1.4 Other Modifications.

The interaction between the Fc region of an antibody and various Fc receptors (FcγR) is believed to mediate the effector functions of the antibody which include antibody-dependent cellular cytotoxicity (ADCC), fixation of complement, phagocytosis and half-life/clearance of the antibody. Various modifications to the Fc region of antibodies of the invention may be carried out depending on the desired effector property. In particular, human constant regions which essentially lack the functions of a) activation of complement by the classical pathway; and b) mediating antibody-dependent cellular cytotoxicity include the IgG4 constant region, the IgG2 constant region and IgG1 constant regions containing specific mutations as for example mutations at positions 234, 235, 236, 237, 297, 318, 320 and/or 322 disclosed in EP0307434

(WO8807089), EP 0629 240 (WO9317105) and WO 2004/014953. Mutations at residues 235 or 237 within the CH2 domain of the heavy chain constant region (Kabat numbering; EU Index system) have separately been described to reduce binding to FcγRI, FcγRII and FcγRIII binding and therefore reduce antibody-dependent cellular cytotoxicity (ADCC) (Duncan et al. Nature 1988, 332; 563-564; Lund et al. J. Immunol. 1991, 147; 2657-2662; Chappel et al. PNAS 1991, 88; 9036-9040; Burton and Woof, Adv. Immunol. 1992, 51; 1-84; Morgan et al., Immunology 1995, 86; 319-324; Hezareh et al., J. Virol. 2001, 75 (24); 12161-12168). Further, some reports have also described involvement of some of these residues in recruiting or mediating complement dependent cytotoxicity (CDC) (Morgan et al., 1995; Xu et al., Cell. Immunol. 2000; 200:16-26; Hezareh et al., J. Virol. 2001, 75 (24); 12161-12168). Residues 235 and 237 have therefore both been mutated to alanine residues (Brett et al. Immunology 1997, 91; 346-353; Bartholomew et al. Immunology 1995, 85; 41-48; and WO9958679) to reduce both complement mediated and FcγR-mediated effects. Antibodies comprising these constant regions may be termed 'non-lytic' antibodies.

One may incorporate a salvage receptor binding epitope into the antibody to increase serum half life see U.S. Pat. No. 5,739,277.

There are five currently recognised human Fcγ receptors, FcγR (I), FcγRIIa, FcγRIIb, FcγRIIIa and neonatal FcRn. Shields et al, (2001) J. Biol. Chem. 276, 6591-6604 demonstrated that a common set of IgG1 residues is involved in binding all FcγRs, while FcγRII and FcγRIII utilize distinct sites outside of this common set. One group of IgG1 residues reduced binding to all FcγRs when altered to alanine: Pro-238, Asp-265, Asp-270, Asn-297 and Pro-239. All are in the IgG CH2 domain and clustered near the hinge joining CH1 and CH2. While FcγRI utilizes only the common set of IgG1 residues for binding, FcγRII and FcγRIII interact with distinct residues in addition to the common set. Alteration of some residues reduced binding only to FcγRII (e.g. Arg-292) or FcγRIII (e.g. Glu-293). Some variants showed improved binding to FcγRII or FcγRIII but did not affect binding to the other receptor (e.g. Ser-267Ala improved binding to FcγRII but binding to FcγRIII was unaffected). Other variants exhibited improved binding to FcγRII or FcγRIII with reduction in binding to the other receptor (e.g. Ser-298Ala improved binding to FcγRIII and reduced binding to FcγRII). For FcγRIIIa, the best binding IgG1 variants had combined alanine substitutions at Ser-298, Glu-333 and Lys-334. The neonatal FcRn receptor is believed to be involved in protecting IgG molecules from degradation and thus enhancing serum half life and the transcytosis across tissues (see Junghans R. P (1997) Immunol. Res 16. 29-57 and Ghetie et al (2000) Annu. Rev. Immunol. 18, 739-766). Human IgG1 residues determined to interact directly with human FcRn include Ile253, Ser254, Lys288, Thr307, Gln311, Asn434 and His435.

The therapeutic antibody of the invention may incorporate any of the above constant region modifications.

In a particular embodiment, the therapeutic antibody essentially lacks the functions of a) activation of complement by the classical pathway; and b) mediating antibody-dependent cellular cytotoxicity. In a more particular embodiment the present invention provides therapeutic antibodies of the invention having any one (or more) of the residue changes detailed above to modify half-life/clearance and/or effector functions such as ADCC and/or complement dependent cytotoxicity and/or complement lysis.

In a further aspect of the present invention the therapeutic antibody has a constant region of isotype human IgG1 with alanine (or other disrupting) substitutions at positions 235 (e.g. L235A) and 237 (e.g. G237A) (numbering according to the EU scheme outlined in Kabat).

Other derivatives of the invention include glycosylation variants of the antibodies of the invention. Glycosylation of antibodies at conserved positions in their constant regions is known to have a profound effect on antibody function, particularly effector functioning such as those described above, see for example, Boyd et al (1996), Mol. Immunol. 32, 1311-1318. Glycosylation variants of the therapeutic antibodies of the present invention wherein one or more carbohydrate moiety is added, substituted, deleted or modified are contemplated. Introduction of an asparagine-X-serine or asparagine-X-threonine motif creates a potential site for enzymatic attachment of carbohydrate moieties and may therefore be used to manipulate the glycosylation of an antibody. In Raju et al (2001) Biochemistry 40, 8868-8876 the terminal sialyation of a TNFR-IgG immunoadhesin was increased through a process of regalactosylation and/or resialylation using beta-1,4-galactosyltransferase and/or alpha, 2,3 sialyltransferase. Increasing the terminal sialyation is believed to increase the half-life of the immunoglobulin. Antibodies, in common with most glycoproteins, are typically produced in nature as a mixture of glycoforms. This mixture is particularly apparent when antibodies are produced in eukaryotic, particularly mammalian cells. A variety of methods have been developed to manufacture defined glycoforms, see Zhang et al Science (2004), 303, 371, Sears et al, Science, (2001) 291, 2344, Wacker et al (2002) Science, 298 1790, Davis et al (2002) Chem. Rev. 102, 579, Hang et al (2001) Acc. Chem. Res 34, 727. Thus the invention concerns a plurality of therapeutic antibodies (which maybe of the IgG isotype, e.g. IgG1) as described herein comprising a defined number (e.g. 7 or less, for example 5 or less such as two or a single) glycoform(s) of said antibodies.

Derivatives according to the invention also include therapeutic antibodies of the invention coupled to a non-proteinaceous polymer such as polyethylene glycol (PEG), polypropylene glycol or polyoxyalkylene. Conjugation of proteins to PEG is an established technique for increasing half-life of proteins, as well as reducing antigenicity and immunogenicity of proteins. The use of PEGylation with different molecular weights and styles (linear or branched) has been investigated with intact antibodies as well as Fab' fragments, see Koumenis I. L. et al (2000) Int. J. Pharmaceut. 198:83-95. A particular embodiment comprises an antigen-binding fragment of the invention without the effector functions of a) activation of complement by the classical pathway; and b) mediating antibody-dependent cellular cytotoxicity; (such as a Fab fragment or a scFv) coupled to PEG.

2. Production Methods

Antibodies of the present invention may be produced in transgenic organisms such as goats (see Pollock et al (1999), J. Immunol. Methods 231:147-157), chickens (see Morrow K J J (2000) Genet. Eng. News 20:1-55), mice (see Pollock et al ibid) or plants (see Doran P M, (2000) Curr. Opinion Biotechnol. 11, 199-204, Ma J K-C (1998), Nat. Med. 4; 601-606, Baez J et al, BioPharm (2000) 13: 50-54, Stoger E et al; (2000) Plant Mol. Biol. 42:583-590). Antibodies may also be produced by chemical synthesis. However, antibodies of the invention are typically produced using recombinant cell culturing technology well known to those skilled in the art. A polynucleotide encoding the antibody is isolated and inserted into a replicable vector such as a plasmid for further propagation or expression in a host cell. One useful expression system is a glutamate synthetase system (such as sold by Lonza Biologics), particularly where the host cell is CHO or NS0 (see below). Polynucleotide encoding the antibody is readily isolated and sequenced using conventional procedures (e.g. oligonucleotide probes). Vectors that may be used include plasmid, virus, phage, transposons, minichromsomes of which plasmids are a typical embodiment. Generally such vectors further include a signal sequence, origin of replication, one or more marker genes, an enhancer element, a promoter and transcription termination sequences operably linked to the light and/or heavy chain polynucleotide so as to facilitate expression. Polynucleotide encoding the light and heavy chains may be inserted into separate vectors and introduced (e.g. by transformation, transfection, electroporation or transduction) into the same host cell concurrently or sequentially or, if desired both the heavy chain and light chain can be inserted into the same vector prior to such introduction.

It will be immediately apparent to those skilled in the art that due to the redundancy of the genetic code, alternative polynucleotides to those disclosed herein are also available that will encode the polypeptides of the invention.

2.1 Signal Sequences

Antigen binding proteins, e.g. antibodies, of the present invention maybe produced as a fusion protein with a heterologous signal sequence having a specific cleavage site at the N terminus of the mature protein. The signal sequence should be recognised and processed by the host cell. For prokaryotic host cells, the signal sequence may be an alkaline phosphatase, penicillinase, or heat stable enterotoxin II leaders. For yeast secretion the signal sequences may be a yeast invertase leader, α factor leader or acid phosphatase leaders see e.g. WO90/13646. In mammalian cell systems, viral secretory leaders such as herpes simplex gD signal and native immunoglobulin signal sequences (such as human Ig heavy chain) are available. Typically the signal sequence is ligated in reading frame to polynucleotide encoding the antibody of the invention.

2.2 Origin of Replication

Origin of replications are well known in the art with pBR322 suitable for most gram-negative bacteria, 2μ plasmid for most yeast and various viral origins such as SV40, polyoma, adenovirus, VSV or BPV for most mammalian cells. Generally the SV40 origin of replication component is not needed for integrated mammalian expression vectors. However the SV40 ori may be included since it contains the early promoter.

2.3 Selection Marker

Typical selection genes encode proteins that (a) confer resistance to antibiotics or other toxins e.g. ampicillin, neomycin, methotrexate or tetracycline or (b) complement auxotrophic deficiencies or supply nutrients not available in the complex media or (c) combinations of both. The selection scheme may involve arresting growth of the host cells that contain no vector or vectors. Cells, which have been successfully transformed with the genes encoding the therapeutic antibody of the present invention, survive due to e.g. drug resistance conferred by the co-delivered selection marker. One example is the DHFR-selection system wherein transformants are generated in DHFR negative host strains (eg see Page and Sydenham 1991 Biotechnology 9: 64-68). In this system the DHFR gene is co-delivered with antigen binding protein, e.g. antibody, polynucleotide sequences of the invention and DHFR positive cells then selected by nucleoside withdrawal. If required, the DHFR inhibitor methotrexate is also employed to select for transformants with DHFR gene amplification. By operably linking DHFR gene to the antigen binding protein, e.g. antibody, coding sequences of the invention or functional derivatives thereof, DHFR gene amplification results in concomitant amplification of the desired antigen binding protein, e.g. antibody, sequences of interest. CHO cells are a particularly useful cell line for this DHFR/methotrexate selection and methods of amplifying and selecting host cells using the DHFR system are well established in the art see Kaufman R. J. et al J. Mol. Biol. (1982) 159, 601-621, for review, see Werner R G, Noe W, Kopp K, Schluter M, "Appropriate mammalian expression systems for biopharmaceuticals", Arzneimittel-Forschung. 48(8):870-80, 1998 Aug. A further example is the glutamate synthetase expression system (Bebbington et al Biotechnology 1992 Vol 10 p 169). A suitable selection gene for use in yeast is the trp1 gene; see Stinchcomb et al Nature 282, 38, 1979.

2.4 Promoters

Suitable promoters for expressing antigen binding proteins, e.g. antibodies, of the invention are operably linked to DNA/polynucleotide encoding the antigen binding protein e.g. antibody. Promoters for prokaryotic hosts include phoA promoter, beta-lactamase and lactose promoter systems, alkaline phosphatase, tryptophan and hybrid promoters such as Tac. Promoters suitable for expression in yeast cells include 3-phosphoglycerate kinase or other glycolytic enzymes e.g. enolase, glyceraldehyde 3 phosphate dehydrogenase, hexokinase, pyruvate decarboxylase, phosphofructokinase, glucose 6 phosphate isomerase, 3-phosphoglycerate mutase and glucokinase. Inducible yeast promoters include alcohol dehydrogenase 2, isocytochrome C, acid phosphatase, metallothionein and enzymes responsible for nitrogen metabolism or maltose/galactose utilization.

Promoters for expression in mammalian cell systems include RNA polymerase II promoters including viral promoters such as polyoma, fowlpox and adenoviruses (e.g. adenovirus 2), bovine papilloma virus, avian sarcoma virus, cytomegalovirus (in particular the immediate early gene promoter), retrovirus, hepatitis B virus, actin, rous sarcoma virus (RSV) promoter and the early or late Simian virus 40 and non-viral promoters such as EF-1 alpha (Mizushima and Nagata Nucleic Acids Res 1990 18(17):5322. The choice of promoter may be based upon suitable compatibility with the host cell used for expression.

2.5 Enhancer Element

Where appropriate, e.g. for expression in higher eukaryotics, additional enhancer elements can be included instead of or as well as those found located in the promoters described above. Suitable mammalian enhancer sequences include enhancer elements from globin, elastase, albumin, fetoprotein, metallothionine and insulin. Alternatively, one may use an enhancer element from a eukaryotic cell virus such as SV40 enhancer, cytomegalovirus early promoter enhancer, polyoma enhancer, baculoviral enhancer or murine IgG2a locus (see WO04/009823). Whilst such enhancers are typically located on the vector at a site upstream to the promoter, they can also be located elsewhere e.g. within the untranslated region or downstream of the polyadenylation signal. The choice and positioning of enhancer may be based upon suitable compatibility with the host cell used for expression 2.6 Polyadenylation/Termination In eukaryotic systems, polyadenylation signals are operably linked to polynucleotide encoding the antigen binding protein, e.g. antibody, of this invention. Such signals are typically placed 3' of the open reading frame. In mammalian systems, non-limiting example signals include those derived from growth hormones, elongation factor-1 alpha and viral (eg SV40) genes or retroviral long terminal repeats. In yeast systems non-limiting examples of polyadenylation/termination signals include those derived from the phosphoglycerate kinase (PGK) and the alcohol dehydrogenase 1 (ADH) genes. In prokaryotic systems polyadenylation signals are typically not required and it is instead usual to employ shorter and more defined terminator sequences. The choice of polyadenylation/termination sequences may be based upon suitable compatibility with the host cell used for expression.

2.7 Other Methods/Elements for Enhanced Yields

In addition to the above, other features that can be employed to enhance yields include chromatin remodelling elements, introns and host-cell specific codon modification. The codon usage of the antigen binding proteins, e.g. antibody, of this invention thereof can be modified to accommodate codon bias of the host cell such to augment transcript and/or product yield (eg Hoekema A et al Mol Cell Biol 1987 7(8):2914-24). The choice of codons may be based upon suitable compatibility with the host cell used for expression.

2.8 Host Cells

Suitable host cells for cloning or expressing vectors encoding antigen binding proteins, e.g. antibodies, of the invention are prokaryotic, yeast or higher eukaryotic cells. Suitable prokaryotic cells include eubacteria e.g. enterobacteriaceae such as *Escherichia* e.g. *E. Coli* (for example ATCC 31,446; 31,537; 27,325), *Enterobacter, Erwinia, Klebsiella Proteus, Salmonella* e.g. *Salmonella typhimurium, Serratia* e.g. *Serratia marcescans* and *Shigella* as well as Bacilli such as *B. subtilis* and *B. licheniformis* (see DD 266 710), *Pseudomonas* such as *P. aeruginosa* and *Streptomyces*. Of the yeast host cells, *Saccharomyces cerevisiae, schizosaccharomyces pombe, Kluyveromyces* (e.g. ATCC 16,045; 12,424; 24178; 56,500), *yarrowia* (EP402, 226), *Pichia Pastoris* (EP183, 070, see also Peng et al J. Biotechnol. 108 (2004) 185-192), *Candida, Trichoderma reesia* (EP244, 234), Penicillin, *Tolypocladium* and *Aspergillus* hosts such as *A. nidulans* and *A. niger* are also contemplated.

Although Prokaryotic and yeast host cells are specifically contemplated by the invention, typically however, host cells of the present invention are vertebrate cells. Suitable vertebrate host cells include mammalian cells such as COS-1 (ATCC No. CRL 1650) COS-7 (ATCC CRL 1651), human embryonic kidney line 293, PerC6 (Crucell), baby hamster kidney cells (BHK) (ATCC CRL. 1632), BHK570 (ATCC NO: CRL 10314), 293 (ATCC NO. CRL 1573), Chinese hamster ovary cells CHO (e.g. CHO-K1, ATCC NO: CCL 61, DHFR minus CHO cell line such as DG44 (Urlaub et al, Somat Cell Mol Genet (1986) Vol 12 pp 555-566), particularly those CHO cell lines adapted for suspension culture, mouse sertoli cells, monkey kidney cells, African green monkey kidney cells (ATCC CRL-1587), HELA cells, canine kidney cells (ATCC CCL 34), human lung cells (ATCC CCL 75), Hep G2 and myeloma or lymphoma cells e.g. NS0 (see U.S. Pat. No. 5,807,715), Sp2/0, Y0.

Thus in one embodiment of the invention there is provided a stably transformed host cell comprising a vector encoding a heavy chain and/or light chain of the therapeutic antibody as described herein. Typically such host cells comprise a first vector encoding the light chain and a second vector encoding said heavy chain.

Such host cells may also be further engineered or adapted to modify quality, function and/or yield of the antigen binding protein, e.g. antibody, of this invention. Non-limiting examples include expression of specific modifying (eg glycosylation) enzymes and protein folding chaperones.

2.9 Cell Culturing Methods.

Host cells transformed with vectors encoding the therapeutic antigen binding proteins, e.g. antibodies, of the invention may be cultured by any method known to those skilled in the art. Host cells may be cultured in spinner flasks, shake flasks, roller bottles, wave reactors (eg System 1000 from wavebiotech.com) or hollow fibre systems but it is preferred for large scale production that stirred tank reactors or bag reactors (eg Wave Biotech, Somerset, N.J. USA) are used particularly for suspension cultures. Typically the stirred tankers are adapted for aeration using e.g. spargers, baffles or low shear impellers. For bubble columns and airlift reactors direct aeration with air or oxygen bubbles maybe used. Where the host cells are cultured in a serum free culture media this can be supplemented with a cell protective agent such as pluronic F-68 to help prevent cell damage as a result of the aeration process. Depending on the host cell characteristics, either microcarriers maybe used as growth substrates for anchorage dependent cell lines or the cells maybe adapted to suspension culture (which is typical). The culturing of host cells, particularly vertebrate host cells may utilise a variety of operational modes such as batch, fed-batch, repeated batch processing (see Drapeau et al (1994) cytotechnology 15: 103-109), extended batch process or perfusion culture. Although recombinantly transformed mammalian host cells may be cultured in serum-containing media such media comprising fetal calf serum (FCS), it is preferred that such host cells are cultured in serum-free media such as disclosed in Keen et al (1995) Cytotechnology 17:153-163, or commercially available media such as ProCHO-CDM or UltraCHO™ (Cambrex N.J., USA), supplemented where necessary with an energy source such as glucose and synthetic growth factors such as recombinant insulin. The serum-free culturing of host cells may require that those cells are adapted to grow in serum free conditions. One adaptation approach is to culture such host cells in serum containing media and repeatedly exchange 80% of the culture medium for the serum-free media so that the host cells learn to adapt in serum free conditions (see e.g. Scharfenberg K et al (1995) in *Animal Cell technology: Developments towards the 21st century* (Beuvery E. C. et al eds), pp 619-623, Kluwer Academic publishers).

Antigen binding proteins, e.g. antibodies, of the invention secreted into the media may be recovered and purified from the media using a variety of techniques to provide a degree of purification suitable for the intended use. For example the use of therapeutic antigen binding proteins, e.g. antibodies, of the invention for the treatment of human patients typically mandates at least 95% purity as determined by reducing SDS-PAGE, more typically 98% or 99% purity, when compared to the culture media comprising the therapeutic antigen binding proteins e.g. antibodies. In the first instance, cell debris from the culture media is typically removed using centrifugation followed by a clarification step of the supernatant using e.g. microfiltration, ultrafiltration and/or depth filtration. Alternatively, the antigen binding protein, e.g. antibody, can be harvested by microfiltration, ultrafiltration or depth filtration without prior centrifugation. A variety of other techniques such as dialysis and gel electrophoresis and chromatographic techniques such as hydroxyapatite (HA), affinity chromatography (optionally involving an affinity tagging system such as polyhistidine) and/or hydrophobic interaction chromatography (HIC, see U.S. Pat. No. 5,429,746) are available. In one embodiment, the antigen binding proteins, e.g. antibodies, of the invention, following various clarification steps, are captured using Protein A or G affinity chromatography followed by further chromatography steps such as ion exchange and/or HA chromatography, anion or cation exchange, size exclusion chromatography and ammonium sulphate precipitation. Typically, various virus removal steps are also employed (e.g. nanofiltration using e.g. a DV-20 filter). Following these various steps, a purified (typically monoclonal) preparation comprising at least 10 mg/ml or greater e.g. 100 mg/ml or greater of the antibody of the invention is provided and therefore forms an embodiment of the invention. Concentration to 100 mg/ml or greater can be generated by ultracentrifugation. Suitably such preparations are substantially free of aggregated forms of antibodies of the invention.

Bacterial systems are particularly suited for the expression of antibody fragments. Such fragments are localised intracellularly or within the periplasma. Insoluble periplasmic proteins can be extracted and refolded to form active proteins according to methods known to those skilled in the art, see Sanchez et al (1999) J. Biotechnol. 72, 13-20 and Cupit P M et al (1999) Lett Appl Microbiol, 29, 273-277.

3. Pharmaceutical Compositions

Purified preparations of antigen binding proteins, e.g. antibodies, of the invention (particularly monoclonal preparations) as described supra, may be incorporated into pharmaceutical compositions for use in the treatment of human diseases and disorders such as those outlined above. Typically such compositions further comprise a pharmaceutically acceptable (i.e. inert) carrier as known and called for by acceptable pharmaceutical practice, see e.g. Remingtons Pharmaceutical Sciences, 16th ed, (1980), Mack Publishing Co. Examples of such carriers include sterilised carrier such as saline, Ringers solution or dextrose solution, buffered with suitable buffers such as sodium acetate trihydrate to a pharmaceutically acceptable pH, such as a pH within a range of 5 to 8. Pharmaceutical compositions for injection (e.g. by intravenous, intraperitoneal, intradermal, subcutaneous, intramuscular, intraportal or by local delivery to the eye by topical or periocular application to the eye or intravitreal injection into the eye) or continuous infusion are suitably free of visible particulate matter and may comprise from 1 mg to 10 g of therapeutic antigen binding protein, e.g. antibody, typically 5 mg to 1 g, more specifically 5 mg to 25 mg or 50 mg of antigen binding protein, e.g. antibody. Methods for the preparation of such pharmaceutical compositions are well known to those skilled in the art. In one embodiment, pharmaceutical compositions comprise from 1 mg to 10 g of therapeutic antigen binding proteins, e.g. antibodies, of the invention in unit dosage form, optionally together with instructions for use. Pharmaceutical compositions of the invention may be lyophilised (freeze dried) for reconstitution prior to administration according to methods well known or apparent to those skilled in the art. Where embodiments of the invention comprise antibodies of the invention with an IgG1 isotype, a chelator of metal ions including copper, such as citrate (e.g. sodium citrate) or EDTA or histidine, may be added to the pharmaceutical composition to reduce the degree of metal-mediated degradation of antibodies of this isotype, see EP0612251. Pharmaceutical compositions may also comprise a solubiliser such as arginine base, a detergent/anti-aggregation agent such as polysorbate 80, and an inert gas such as nitrogen to replace vial headspace oxygen.

Effective doses and treatment regimes for administering the antigen binding protein, e.g. antibody, of the invention are generally determined empirically and are dependent on factors such as the age, weight and health status of the patient and disease or disorder to be treated. Such factors are within the purview of the attending physician. Guidance in selecting appropriate doses may be found in e.g. Smith et al (1977) Antibodies in human diagnosis and therapy, Raven Press, New York but will in general be 1 mg to 10 g. In one embodiment, the dosing regime for treating a human patient is 1 mg to 1 g of therapeutic antibody of the invention administered subcutaneously once per week or every two weeks, or by intravenous infusion every 1 or 2 months. Such a dosage corresponds to 0.014-140 mg/kg, such as 0.014-14 mg/kg. Compositions of the present invention may also be used prophylactically.

Compositions may also be delivered more locally to the eye either by topical application, intravitreal injection or periocular administration, i.e. subsclerally via either retrobulbar, peribulbar, subtenon or subconjunctival injection. Systemic administration may be sufficient to achieve drusen reduction via passive, e.g. intravenous administration of the therapeutic antibody. Other routes of local administration may allow the therapeutic antibody to reach the posterior segment of the eye more readily at lower doses. Topical application has been described to allow penetrance of antibody fragments to the posterior of the eye in the rabbit model, (Williams K A, Bereton H M, Farrall A, Standfield S D, Taylor S D, Kirk L A, Coster D J (2005) Eye 19; 910-913). Intravitreal injection of antibody fragments or full monoclonal antibodies has been described and is well-tolerated for AMD patients for the products ranibizumab and bevacizumab. Therapeutic antibody may also be administered by an intravitreal implant. Retrobulbar and peribulbar injections can be achieved with special 23 to 26 gauge needles and are less invasive than intravitreal injections. Subtenon injection places the composition in contact with the sclera for a longer period which could aid penetration to the posterior eye. Injection of proteins just beneath the conjunctiva has been described in rabbit models and this allows molecules to diffuse more directly across the sclera to reach the posterior segment of the eye. Sustained release drug delivery systems may also be used which allow for release of material over a longer time-frame into or around the eye so that dosing could be less frequent. Such systems include micelles, gels, hydrogels, nanoparticles, microcapsules or implants that can be filled or coated with therapeutic compositions. These may be delivered into the vitreous of the eye by injection or by any of the other previously described less invasive routes, i.e. through the periocular or sub-scleral routes. Examples of such sustained release systems and local delivery routes include thermo-sensitive slow release hydrogels for subscleral administration or intravitreal administration of a nanoparticle based formulation that targets to the posterior retina and RPE layer (Janoira K G, Gunda S, Boddu S H S, Mitra A K, (2007) Expert Opin Drug Deliv 4: 371-388; Birch D G, Liang F Q, (2007) Int J Nanomed 2:65-77). Many other combinations of delivery system and local administration route are possible and could be considered for compositions of therapeutic antibody. An antibody may also be delivered by a physical device such as via iontophoresis (Association for Research in Vision and Opthalmology, 2008, Annual meeting, April $27^{th}$-May $1^{st}$, Posters #98/A125 & #1813/D693 from EyeGate Pharma: Blalock et al., & Ruiz-Perez et al).

4. Clinical Uses

It will be appreciated that diseases characterised by elevated β-amyloid levels or β-amyloid deposits include Alzheimer's disease, mild cognitive impairment, Down's syndrome, hereditary cerebral hemorrhage with β-amyloidosis of the Dutch type, cerebral β-amyloid angiopathy and various types of degenerative dementias, such as those associated with Parkinson's disease, progressive supranuclear palsy, cortical basal degeneration and diffuse Lewis body type of Alzheimer's disease, age-related macular degeneration (AMD), "Glaucoma type" diseases and Aβ dependent cataract formation.

In an embodiment of the invention, the disease characterised by elevated β-amyloid levels or β-amyloid deposits is Alzheimer's disease.

In a further embodiment of the invention, the disease characterised by elevated β-amyloid levels or β-amyloid deposits is age-related macular degeneration (AMD), "Glaucoma type" diseases or Aβ dependent cataract formation.

Although the present invention has been described principally in relation to the treatment of human diseases or disorders, the present invention may also have applications in the treatment of similar diseases or disorders in non-human mammals.

| Examples Methods | |
|---|---|
| ABi8200 | Applied Biosystems 8200 fluorescence macro confocal cellular detection system for FMAT |
| Biacore ™/ Biacore | a device that allows measurement of real time kinetics of molecular interactions using SPR |
| CM5 | Biacore ™ sensor chip with general purpose surface coated with a carboxymethylated dextran matrix |
| cSLO | Confocal Scanning Laser Ophthalmoscope |
| ELISA | enzyme linked immunosorbent assay |
| FMAT | fluorometric microvolume assay technology (Applied Biosystems) |
| FPLC | Fast protein liquid chromatography |
| IHC | Immunohistochemistry |
| Integra CL1000 | Mini-bioreactors sold by IBS Integra Biosciences |
| MSD ® | Meso Scale Discovery |
| ProSepA HiTrap | Protein A columns for FPLC sold by GE Healthcare |
| RU | Resonance Unit (arbitrary unit to quantify binding to sensor chip in Biacore measurements) |
| SDS-PAGE | sodium dodecyl sulfate - polyacrylamide gel electrophoresis |
| SPR | (surface plasmon resonance) - physical phenomenon employed by Biacore ™ instruments for measurement of mass changes on sensor chip |
| SPSS | statistical analysis software package |
| SRU | SRU BIND ™ Biosensor technology allowing to monitor label-free biochemical interactions |
| Materials | |
| BSA | bovine serum albumin |
| C57/BL6 | "C57 black 6" - common inbred strain of laboratory mice |
| DAB | 3,3'diaminobenzidine |
| DAPI | 4',6-diamidino-2-phenylindole |
| DMEM | dulbecco's modified eagle's medium |
| DMSO | dimethylsulphoxide |
| DTT | dithiothreitol |
| EDTA | ethylenediaminetetraacetic acid |
| FA | formic acid |
| FCS | fetal calf serum |
| FITC | fluorescein isothiocyanate |
| Glutamax | stable form of glutamine added to culture medium (dipeptide L-Ananyl-L-Glutamine supplement) |
| HEK | human embryonic kidney 293 cells |
| HBS-EP buffer | General purpose Biacore ™ buffer containing 0.01M HEPES pH 7.4, 0.15M NaCl, 3 mM EDTA, 0.005% Surfactant P20 |
| HEPES | N-(2-hydroxyethyl)piperazine-N'-(2-ethanesulfonic acid) |
| Histoclear | tissue clearing agent |
| HRP | Horse radish peroxidase |
| IMS | industrial methylated spirit |
| Lipofectamine | cationic lipid based cell transfection agent sold by Invitrogen/Gibco |
| NaCl | sodium chloride |
| Opti-MEM | modified eagle's medium based medium by Invitrogen/Gibco |
| PBS | phosphate buffered saline |
| PFA | paraformaldehyde |

-continued

| | |
|---|---|
| PEG | polyethylene glycol |
| PPD | purified protein derivative |
| PRF F12 | phenol red free medium with Nutrient Mixture F-12 |
| RIBI | water-oil emulsion based antigen adjuvant |
| RT-PCR | reverse transcribed - polymerase chain reaction |
| TASTPM | double transgenic mouse strain created by crossing APP695 Swedish mutation mice (TAS10) with a PS-1M146V strain (TPM) |
| TBS | TRIS buffered saline |
| Transfast | liposomal transfection agent sold by Promega |
| Tris HCl | tris-(hydroxymethyl)aminomethane hydrochloride |
| Tween-20 | polyoxyethylenesorbitan monolaurate |
| Versene | metal ion chelating agent (ethylenediaminetetra-acetic acid) |
| Abbreviations | |
| AMD | age-related macular degeneration |
| APP | amyloid precursor protein |
| BM | Bruch's membrane |
| CFH | Complement factor H |
| CFI | Complement factor I |
| CHO | Chinese hamster ovary cells |
| CNV | choroidal neovascularisation |
| CPM | counts per minute |
| CSF | cerebrospinal fluid |
| ICV | intracerebroventricular |
| IgG | immunoglobulin gamma |
| i.p. | intra-peritoneal |
| hAPP | human amyloid precursor protein |
| HIER | heat-induced antigen retrieval |
| HVT | healthy volunteer |
| KD | dissociation constant at equilibrium |
| NDS | Normal Donkey Serum |
| MO | months old |
| MRT | mean residence time |
| OS | Outer segments |
| RPE | retinal pigment epithelial cells |

Generation of Mouse Monoclonal Antibodies Specific for Human Beta Amyloid

One set of mice were initially immunised with peptide CGGGNKGAIIGLMVGG (containing residues 27-38 of β-amyloid) (SEQ ID No:7) N-terminally coupled to PPD. The immune response of these mice was assessed by taking a serum sample and testing this in an ELISA with ovalbumin conjugates of the same peptide to determine the antibody titre for the immunised mice. Only weak responses were observed. In another experiment a set of mice was immunised with 10 μg of N-terminal coupled CGGGEDVGSNKGAI-IGLMVGG peptide (containing residues 22-38 of β-amyloid) (SEQ ID No:73) conjugated to PPD (purified protein derivative; Cambridge Research Biochemicals) in RIBI adjuvant via the intra peritoneal route. The immune response of these mice was again assessed by taking a serum sample 7 days after each boost and testing this in an ELISA to determine the antibody titre for the immunised mice. Once the mice had reached an optimal response (based on a comparison analysis of antibody titre in the last two serum samples) by boosting with 2.5 μg peptide conjugate, the mouse with the best antibody titre was culled and the spleen taken for hybridoma generation. Hybridomas were generated by obtaining the spleen cells and fusing these with myeloma cells using PEG (polyethylene glycol) methodology. The resultant mixed cell population was then plated out into 96 well cell culture plates.

Each of the expressed antibodies contained in culture supernatant was then screened in an FMAT (Fluorescent Microvolume Assay Technology) homogenous immunoassay. 29 positive antibodies were identified from this screening cascade that were negative for ovalbumin protein passively absorbed to polystyrene beads but positive for:

(i) N-terminal coupled CGGGEDVGSNKGAIIGLMVGG (22-38) (SEQ ID No:73) ovalbumin conjugate bound to polystyrene beads,
(ii) N-terminal biotinylated β-amyloid(1-40) peptide bound to streptavidin coated polystyrene beads,
(iii) C-terminal biotinylated β-amyloid(1-40) peptide bound to streptavidin coated polystyrene beads and
(iv) N-terminal biotinylated β-amyloid (24-34) peptide, residues 24-34 of β-amyloid being VGSNKGAIIGL (SEQ ID No:8), bound to streptavidin coated polystyrene beads.

The selected antibody supernatant samples were analysed for binding kinetics to β-amyloid(1-40) peptide as outlined below.

Determination of Binding Interaction Off-Rates (kd) Using Surface Plasmon Resonance Assay A Biacore A100 instrument was used to provide off-rate kinetics for the interaction of the 29 selected antibodies with β-amyloid(1-40). For this, a streptavidin Biacore sensorchip flowcells were derivatised with low levels of N-terminal biotinylated β-amyloid(1-40). Three curves were generated for each antibody sample and fitted to rate equations to obtain the dissociation rates. For 12 clones a ranking based on off-rate was not possible since measurement of the dissociation rate was not possible with the experimental conditions chosen. However, under these conditions, all 12 clones showed an off-rate (kd) of at least $10^{-5}$.

Human β-Amyloid Binding ELISA

The 29 antibodies contained in the hybridoma supernatants identified above were re-tested for binding to human β-amyloid (1-40) by ELISA. In order to allow a valid comparison the concentration of the antibody contained in the culture supernatants was determined using an IgG quantification ELISA. To determine the isotype of the functional antibody a human β-amyloid binding ELISA was carried out using a set of isotype-specific detection antibodies. All 29 antibodies bound to human β-amyloid(1-40) in this ELISA format. Isotypes for each bound antibody clone could be identified by the isotype specific secondary antibody being used to either IgG1, IgG2a or IgG2b. In one case a mixture of functional isotypes was observed.

Epitope Mapping by ELISA Using Overlapping Peptides

The epitopes recognised by the 29 antibodies selected from the primary screen and contained in hybridoma supernatants were mapped by ELISA using a set of 31, 12-mer overlapping peptides which covered the complete sequence of the β-amyloid 1-42 peptide. All peptides contained a 3 amino C-terminal linker (glycine-serine-glycine) and a terminal biotinylated lysine residue.

96 Well immunoassay plates were coated overnight at 4° C. with 100 μl 0.5 μg/well streptavidin (Sigma) in distilled water. Plates were washed three times (PBS/0.01% Tween 20) and wells blocked with 250 μl/well 3% BSA in PBS for 1 hour at room temperature. Plates were washed three times and 100 ul of peptide solutions (0.5 ug/well in 1% BSA 0.1% Tween 20 in PBS) were added to triplicate wells, for 3 hours at room temperature. DMSO only control wells were also prepared. Plates were washed three times and 100 μl of the 29 hybridoma supernatants (diluted 1/20 in 1% BSA/0.1% Tween 20) were added to all of the wells and incubated at 4° C. overnight. Plates were washed three times and anti-mouse IgG antibody-horse radish peroxidase conjugate (Amersham, diluted 1:2000 in 1% BSA, 0.1% Tween 20 in PBS) was added at 100 μl/well. Plates were incubated for one hour at room temperature, washed three times, and the binding of the detection antibody revealed using 100 ul/well of tetramethylbenzidine (Sigma) substrate for approximately 5 mins at room temperature monitoring development of blue colour. The reaction was stopped and the optical density read for each well at 450 nm.

All antibodies bound to a very similar region containing the motif KGAIIGLM (equivalent to residues 28-35 of β-amyloid) (SEQ ID No:9).

Binding Kinetics Determined by Surface Plasmon Resonance Assay

The β-amyloid binding affinities and kinetics for 8 monoclonal antibodies selected from the pool of 29 were assessed in more detail using Biacore 3000 technology. Purified mouse antibody preparations were captured on a polyclonal anti-mouse IgG antibody chip surface. Freshly prepared human β-amyloid 1-40 was diluted down in HBS-EP buffer and passed over the captured antibody surface at concentrations ranging from 4-500 nM for 5 minutes. Dissociation after the injection was observed for a further 20 minutes. Regeneration was achieved via a pulse of 100 mM $H_3PO_4$. Subsequent cycles of antibody capture and β-amyloid binding were shown to be unaffected by regeneration. All runs were double referenced against a blank surface and blank buffer injections. The data obtained is shown in Table 2.

TABLE 2

Biacore affinity and kinetic data for eight selected purified antibodies; KD values shown are from one experiment

| mAb | ka (1/Ms) | kd (1/s) | KD (nM) |
|---|---|---|---|
| 2C1 | 6.63e4 | 1.29e−4 | 1.95 |
| 5C9 | 6.11e4 | 1.64e−4 | 2.69 |
| 4D4 | 7.32e4 | 8.27e−5 | 1.13 |
| 5D1 | 5.7e4 | 1.47e−4 | 2.57 |
| 6F6 | 1.06e5 | 6.57e−5 | 0.62 |
| 14B3 | 7.48e4 | 7.11e−5 | 0.95 |
| 2E11 | 8.45e4 | 1.7e−4 | 2.01 |
| 16D4 | 8.12e4 | 6.18e−4 | 7.62 |

Results showed that affinities of all 8 monoclonal antibodies were comparable although 16D4 showed an at least 12 to 2.5-fold lower affinity compared to the other clones. The differences in KD values between the remaining 7 antibodies in this one experiment were up to 4.4-fold. Two of these clones, 5D1 and 6F6, were selected for further scale-up and retested in triplicate. This data is shown in Table 3.

TABLE 3

Biacore kinetic and affinity data for purified monoclonal antibodies 6F6 and 5D1 (triplicate run)

| mAb | ka (1/Ms) | kd (1/s) | KD (nM) |
|---|---|---|---|
| 5D1 (n = 3) | 6.58e4 ± 0.38e4 | 1.35e−4 ± 0.10e−4 | 2.05 ± 0.15 |
| 6F6 (n = 3) | 9.93e4 ± 0.93e4 | 9.4e−5 ± 3.2e−5 | 1.02 ± 0.41 |

The same Biacore method was also used to investigate binding of 6F6 to human and mouse β-amyloid (1-40) and β-amyloid (1-42). 6F6 bound to all of these peptides with similar values.

Binding to Cell Expressed Amyloid Precursor Protein (APP)

β-Amyloid is composed of peptides formed by proteolytic cleavage of a type I transmembrane precursor protein named amyloid precursor protein (APP). As APP has a large extracellular domain, binding to this protein could potentially initiate an antibody-dependent cellular cytotoxicity reaction (ADCC).

FMAT™ ABI8200 Based Assay

Fluorometric Microvolume Assay Technology (FMAT; Cellular Detection System 8200) was used to perform a cell based binding assay to amyloid precursor protein expressed on HEK 293T cells with the 8 antibodies selected above. HEK293T cells, either mock transfected, or transfected with a plasmid encoding full length human APP were harvested 48 hrs post transfection. Transfected cells were incubated with various dilutions of the hybridoma supernatants or with purified positive control antibodies LN27 (Zymed) mouse IgG to extracellular domain of APP and a negative control antibody which only recognises the free N-terminus of the β-amyloid peptide (in house reagent). Antibody binding was revealed using FMAT blue tagged anti-mouse antibody and detected using the Cellular Detection System 8200. Background signals obtained from the mock transfected cells were subtracted from the APP transfected cells. 7 clones showed no binding to APP expressed on HEK293T cells in comparison to the positive control monoclonal antibody LN27. On studying the results with the mock-transfected HEK293T cells one clone (5C9) showed evidence of non-specific binding to HEK293T cells making interpretation of the APP binding capacity of this particular clone difficult.

Binding to Amyloid Precursor Protein (APP) in Brain Sections of Transgenic Mice

Brain sections of 2 month old TASTPM (Howlett et al 2008) or 12 month old TAS10 mice were investigated by IHC. Sections were treated with 85% formic acid and stained for full length APP binding. At the age chosen the respective mice do not show any amyloid plaques deposits although some staining maybe due to intracellular amyloid being accessible using this technique. 6F6 showed no staining in these sections whereas a control antibody for full length APP (Zymed) did show staining.

Human β-Amyloid Binding ELISA as a Fab Fragment

A Fab fragment of 6F6 was generated by standard protease cleavage using papain immobilised on beads (Pierce #20341). An ELISA was carried for binding to human Aβ peptide (1-40) immobilised on an ELISA plate with purified Fab fragments of 6F6 IgG. Result from a single ELISA experiment showed that a Fab fragment of 6F6 is still able to bind to Aβ peptide (1-40).

Binding of 6F6 to Native Human Amyloid in Plasma Samples from Human Volunteers

Whole blood from healthy volunteers (HVT) was collected into a K2 EDTA tube by venipuncture and the tube placed on ice immediately. The blood sample was processed within 30 minutes by spinning at 2000×g for 15 minutes at 4° C. to obtain plasma. Protease inhibitor (Roche Complete Protease Inhibitor cocktail, Cat No: 11 973 580 001, Roche Applied Science) was then added to the plasma according to the manufacturer's instructions. The aliquots of plasma were then frozen at below −70° C. before analysis.

The assay used 6F6 as a capture antibody in a 96-well ECL immunoassay format (Meso Scale Discovery, MSD). Briefly, 6F6 was spot-coated onto a 96-well MSD plate; samples (assay calibrator, negative control, QC and test samples) were then added. Following incubation, unbound material was washed away and the detection antibody (biotinylated 4G8, (specific for the β-amyloid epitope 17-24)) was then applied to incubate. This was followed by the addition of streptavidin-sulfo-TAG after washing. At the end of this incubation, a wash step was applied. The addition of MSD Read Buffer T to the plate enabled an electrochemiluminescent signal to be read on the MSD Sector Imager 6000. The analyte concentration was back-calculated from MSD signal using an assay standard curve established with known concentrations of Aβ1-42. The lower limit of quantification for the assay was 78.1 pg/mL.

Table 4 summarizes the Aβ concentrations of 10 HVT plasma samples as measured by the 6F6-4G8 antibody assay described above. All samples were tested in duplicate.

TABLE 4

| Aβ concentration in HVT samples as measured by 6F6-4G8 antibodies | | | |
|---|---|---|---|
| Sample | Rep1 | Rep2 | Mean |
| HVT1 | 695.780 | 653.251 | 674.517 |
| HVT2 | 602.650 | 596.211 | 599.431 |
| HVT3 | 685.350 | 684.026 | 684.688 |
| HVT4 | 660.760 | 653.754 | 657.259 |
| HVT5 | 629.980 | 582.975 | 606.478 |
| HVT6 | 524.470 | 517.987 | 521.230 |
| HVT7 | 681.420 | 678.934 | 680.175 |
| HVT8 | 618.910 | 579.181 | 599.045 |
| HVT9 | 616.190 | 605.367 | 610.779 |
| HVT10 | 1029.050 | 947.771 | 988.413 |
| | | Mean | 662.202 |
| | | SD | 125.153 |

Binding to Aβ1-42 Under Native and Denaturing Conditions by Western Blot

Purified 6F6 monoclonal antibody was investigated for binding to various forms of Aβ1-42 and analysed under native or denaturing SDS-PAGE. Aβ1-42 was either used freshly prepared or pre-treated overnight with PRF F12 at 4° C., overnight in PBS at 37° C. or overnight in 10 mM HCl at 37° C. Preparations were separated by SDS-PAGE and analysed by Western blotting using 6F6 antibody or 6E10 (antibody specific for human Aβ 1-16; commercial reagent, Eurogentec) and 5G5 (antibody specific for A1-42; in house reagent). Results showed that on native gels 6E10 recognises higher forms of amyloid whereas 6F6 and 5G5 only showed a relatively weak signal to these oligomeric and fibrillar forms. Under denaturing conditions 6F6 and 5G5 predominantly recognised monomeric forms of beta amyloid whereas the N-terminal specific 6E10 was still able to bind to higher aggregates of beta amyloid that were not resolved by the denaturing conditions used in this experiment FIG. 1). In conclusion this indicates that under these conditions and using the amyloid preparations described above 6F6 is preferentially binding to lower molecular weight forms and monomers of Aβ1-42.

Epitope Mapping by ELISA of Purified Monoclonal Antibody 6F6

Purified 6F6 monoclonal antibody was used to repeat the epitope mapping outlined above by ELISA. The protocol used was the same except that 100 μl of diluted purified antibody solution (0.1 ug/ml in 1% BSA) was added instead of diluted hybridoma culture supernatant.

Purified 6F6 monoclonal antibody bound to motif KGAIIGL (equivalent to residues 28-34 of β-amyloid) but binding was much enhanced if residue 35M was included in the peptide (equivalent to residues 28-35 of β-amyloid; (SEQ ID No:9)). Minor contributions of neighbouring residues cannot be excluded using overlapping epitope mapping techniques.

Epitope Mapping by Surface Plasmon Resonance of Monoclonal Antibody 6F6

Purified 6F6 monoclonal antibody was injected for 3 min at 8-64 nM over C-terminally biotinylated peptides representing 24-35 (SEQ ID No:10: VGSNKGAIIGLMGSG), 28-39 (SEQ ID No:11: KGAIIGLMVGGVGSG) and 31-42 (SEQ ID No:12: IIGLMVGGVVIAGSG) of the β-amyloid sequence captured by a streptavidin coated sensorchip. The experiment was performed using a Biacore 3000 instrument. Results showed that 6F6 was able to bind to peptide 24-35 and 28-39 but not to peptide 31-42 of β-amyloid, confirming the overlapping peptide results above. It may also indicate that residues 31-35 are not sufficient for binding 6F6 and residues above position 35 appear not to be involved in binding this antibody.

Effect of Intravenous Administration of Anti-β-Amyloid Monoclonal Antibodies 6F6 and 5D1 on Amyloid Blood Levels Following Centrally Administered Amyloid The objective of this study was to investigate the levels of radioactivity in blood following the intracerebroventricular (ICV) injection of $^{125}$I (1 μCi) β-amyloid 1-40, in mice that had been pre-injected intravenously with test antibody.

$^{125}$I (1 μCi) β-amyloid 1-40 was administered to ICV cannulated male C57BL6/J mice (n=8-10 per treatment) by ICV infusion. One hour prior to ICV infusion of $^{125}$I β-amyloid 1-40, mice were intravenously injected with either phosphate buffered saline (PBS) or 600 μg of anti-β-amyloid monoclonal antibody 6F6 or 5D1. Animals were returned to home cages post-ICV infusion and at 4 hours post ICV-infusion were culled and blood was sampled and counts per minute (CPM) gamma radiation was detected.

Surgical Preparation.

Mice were anaesthetised by inhalation of isofluorane (3-5%) and placed into a stereotaxic frame. Prior to any surgical procedures mice received 0.05 mls (1:10 dilution from stock) subcutaneous Vetergesic® (Buprenorphine) for analgesia. An incision was made along the midline of the scalp and the dorsal aspect of the skull cleared and dried. A cannula was placed into the lateral ventricle via a bore hole through the skull at the following stereotaxic coordinates relative to bregma (anterioposterior (AP): −0.5, lateral (L): +0.7, dorsal/ventral (DV): −2.5). A further two bore holes were drilled through the skull into which cortical screws were placed. The cannula was anchored in place by cyanoacrylate gel and the incision was sutured around the cyanoacrylate gel headcap. Post-operatively the mice received 0.3 ml saline subcutaneously and were placed in a warm environment to recover from anaesthesia. On recovery of righting relex mice were housed singly and subject to 5 days standard post-op care. No further procedures were carried out for 5 days or until pre-operative body weight was regained.

Cannula Placement

Following recovery the cannula placement was verified by the angiotensin II drinking response. Each mouse received ICV administration of 10 ng angiotensin II. Following administration water intake was observed for 15 minutes.

Results

A significant increase in radioactivity in the blood of animals dosed with both monoclonal antibodies 6F6 and 5D1 was observed in comparison to animals dosed with vehicle presumably due to the ability to bind radiolabeled β-amyloid in circulation and thus extending the half life in blood of the labelled β-amyloid 1-40 peptide. Differences between the monoclonal antibodies were not significant. 6F6 and 5D1 treatment resulted in a statistically significant increase in CPM vs. vehicle injected control—(CPM: Vehicle 1280+/−312; 5D1 8152+/−2001; 6F6 8875+/−2123) Univariate ANOVA, F (3.32)=15.14, p<0.001 (data log transformed), post-hoc LSD test ***p<0.001 all groups vs. vehicle.

Investigation of the Pharmacokinetics of 6F6-Amyloid Complex Formation in Guinea Pigs The objective of this study was to determine the formation of antibody-β-amyloid complexes in vivo in guinea pigs which have a β-amyloid amino acid sequence identical to humans. This was achieved by measuring free antibody concentration and antibody-β-amyloid complexes at various time points over a 19 day period.

Method

Male Dunkin-Hartley guinea-pigs were surgically prepared, under isofluorane anaesthesia with double jugular vein cannulae. Cannulated guinea-pigs received an intravenous infusion of antibody 6F6 (n=6) over 1 h. Purified antibody preparations in PBS solution were administered at 0.700 and 0.625 mL/kg/h, respectively to achieve a target dose of 3 mg/kg. Blood samples (60 μl) were removed from each guinea-pig pre-dose (0 min) and collected using EDTA tubes at the following times (over 20 days) after the start of infusion: 15, 30, 45, 60 (iv infusion off), 90, 120, 180, 360 min, 8, 10, 24, 48, 72, 96, 120, 144, 168, 192, 216, 240, 264, 312, 360, 408 and 456 h.

Large samples (0.5 ml) were taken at 0, 10, 96, 216, 312 and 456 h after the start of the infusion. Following the last blood sample on day 20, animals were anaesthetised and exsanguinated. Plasma samples were stored at −80° C. until analysis by ELISA. Free antibody levels were assessed by antigen binding ELISA using β-amyloid 1-40 coated microtiter plates. Plasma samples from 0, 10 h, 96 h, 196 h, 312 h and 456 h were added to these wells and bound 6F6 monoclonal antibody detected using anti-mouse IgG-HRP conjugate. β-Amyloid-antibody complexes were detected by capture on plates coated with β-amyloid 42 C-terminal-specific polyclonal antibody. Captured complexes were detected through the 6F6 monoclonal antibody by anti-mouse IgG biotin conjugate and streptavidin europium kryptate.

Results

Free antibody levels increased rapidly as expected after IV (intravenous) delivery but also declined rapidly within the first 24 h period. Levels reached a steady state level at around 160 h. Results show blood clearance rate of 1.75 ml/h/kg for 6F6 antibody and a mean residence time (MRT) of 49.4 h.

Complex levels also rose quickly after administration of antibody and mean complex levels remained stable at that level over the remainder of the study. However, individual animals showed considerable variation. In some animals complex levels declined, in some animals complex levels increased but in most cases complex levels appeared stable from about 216 h time point onwards. The experiment showed that complexes with human equivalent amyloid can be formed in vivo and that the level of complexes appears unchanged for a long period of time in plasma after single dose administration.

4 Week Dosing Study with 6F6 in Transgenic TASTPM Mice

Transgenic (tg) mice over-expressing human amyloid precursor protein (hAPP) provide a model of amyloidosis and are suitable to study the influence of drugs on amyloid production, sequestration and deposition. For this study we used TASTPM transgenic mice which over-express human amyloid precursor protein and a mutant form of presenilin 1 (double transgenic mouse strain created by crossing an APP695 Swedish mutation mice (TAS10) with a PS-1M146V strain (TPM) (Howlett et al 2008). The study was carried out in approximately 10 week old male and female mice.

Animals were in Three Treatment Groups:
Treatment Groups:
(A) Tg animals terminated on day 1 receiving no compound to determine amyloid levels at start of study (n=16; 9 male, 7 female)
(B) Tg animals receiving vehicle (PBS) by intraperitoneal injection twice weekly for 4 weeks (n=19; 9 male, 10 female)

(C) Tg animals receiving 6F6 300 µg per mouse by intraperitoneal injection twice weekly for 4 weeks (n=19; 9 male, 10 female)

Animals were divided into 3 treatment cohorts starting the dosing regime one week apart.

Blood samples were taken before $2^{nd}$, $4^{th}$, $6^{th}$ and $8^{th}$ dose from 3 male and 3 female animals per treatment group by tail vein bleeds. Terminal EDTA plasma samples were prepared from all groups on day 1 (Group A) or 4 weeks after first dose (groups B and C). Left and right brain hemispheres were taken, snap frozen and stored at −80° C. until subsequent analysis for biochemical amyloid levels. Tail tips were also taken and used for confirmation of genotype.

Determination of Biochemical Amyloid Load in Brain Homogenates

The level of Aβ1-40 and Aβ1-42 in extracted brain samples was determined using ORIGEN technology (Igen International Inc). Briefly, brain hemispheres were weighed and extracted in 5M guanidine HCl (Calbiochem) containing Complete TM protease inhibitor (Roche Diagnostic) at 150 mg/ml w/v using a hand held pestle. Extracts were diluted in Igen buffer and 1:10 and 1:40 dilutions cleared by centrifugation at 20000 g used in the assay.

The ORIGEN assay used streptavidin coated Dynabeads (Dynal) with immobilised biotinylated 6E10 antibody (specific for human Aβ 1-16; Signet Labs) to capture Aβ from the samples and detection of bound Aβ with ori-tag labelled G210 (antibody specific for A1-40; in house reagent) or 5G5 (antibody specific for A1-42; in house reagent).

Analysis of the Aβ1-40 and Aβ1-42 burden post-mortem from each group showed no 6F6 treatment related reduction of brain amyloid burden in this study and by the analytical method employed here. Definitive conclusions on the potential reduction of brain amyloid could not be reached because the pattern of Aβ increase in the brain of vehicle treated animals over the course of the study was small and not uniform across all animals.

Determination of Plasma Levels of 6F6 Antibody

Longitudinal and terminal EDTA plasma samples were assessed for antibody levels by ELISA. Briefly, samples were diluted 1:50, 1:500 and 1:5000 and added to ELISA plates with 0.5 µg/ml immobilised Aβ1-40 peptide diluted in PBS. Samples were incubated overnight at 4° C., washed and bound 6F6 antibody detected using anti-mouse horse radish peroxidase conjugate. Concentrations in samples were determined by use of a standard curve produced using 8 known concentrations of 6F6 ranging from 0 to 30 µg/ml.

Results showed that all mice were successfully dosed with 6F6 antibody and that terminal plasma concentrations had a mean value of approximately 250 µg/ml. Longitudinal plasma samples showed an increase in plasma levels between the $2^{nd}$ and $4^{th}$ dose due to repeat administration but maintaining a level of at least 150 µg/ml until the end of the study in all animals sampled.

Determination of Amyloid-Antibody Complexes in Plasma by Immunoprecipitation and Western Blot In order to examine whether antibody-Aβ complexes had been formed in this in vivo study the plasma samples were investigated for formation of complexes using immunoprecipitation and subsequent western Blot analysis. Briefly, 15 µl plasma samples were incubated and shaken for 3 h at 4° C. with 10 µl of protein A sepharose bead slurry. Beads were washed 5 times in 1 ml ice cold PBS containing protease inhibitor. Each time samples were centrifuged for 2 min at 2000 rpm at 4° C. After washing beads were resuspended in 20 µl electrophoresis sample buffer containing 0.1M DTT. Samples were boiled for 5 min and centrifuged as above.

After re-boiling the supernatant, samples were loaded on 10% Bis/tris minigels and separated by electrophoresis. Gels were blotted onto nitrocellulose membrane, blocked and probed with 6E10 antibody (specific for human Aβ 1-16; Signet Labs). Detection of bound 6E10 was with IR dye800 conjugated goat anti-mouse IgG (H+L) antibody (Rockland). Blots were visualised using an Odysee infrared imaging system.

Results showed that low molecular weight Aβ could be detected on the blots that co-purified using the immunoprecipitation method. This would conclude that complexes of 6F6 with Aβ were formed in vivo and present in the plasma samples. The band intensity was weaker in the female animals tested. Overall, this confirmed that 6F6 is able to bind to human Aβ in vivo and form stable complexes that can be detected by Western Blotting.

16 Week Dosing Study with 6F6 in Transgenic hAPP Mice

Transgenic mice over-expressing hAPP(751) under the control of the murine Thy-1 promoter were used that express human APP with London (717) and Swedish (670/671) mutations in high levels, resulting in an age dependent increase of Amyloid beta 1-40 and Amyloid beta 1-42 (Aβ1-40 and Aβ1-42). These mice develop plaques consisting of amyloid depositions in early age, starting at approximately 4 months. Severity of the brain pathology correlates with increasing age and behavioral deficits This study was carried out blinded to the investigator not revealing the identity of the compound being administered. Female transgenic mice with an age of 4 months were allocated to 3 groups (n=15 per group) as well as a group of non-transgenic littermates and treated weekly via intraperitoneal route over a time period of 4 months. The littermates group and one Tg group receiving control IgG served as controls. At the end of the treatment behavioural testing was carried out (Morris Water Maze, New Object Recognition Task) and animals were sacrificed. Brain, CSF and blood plasma was collected. One hemisphere of each brain was processed for histological evaluation the second was immediately frozen for determination of Aβ1-38, Aβ1-40 and Aβ1-42 in the TBS, Triton X-100, SDS and formic acid (FA) brain homogenate fractions as well as CSF. Brain plaque load in fixed samples was determined using immunostaining with anti-beta amyloid antibody 6E10 and plaque surface area and number of plaques were determined and counted with a computerized image analysis software (Image Pro Plus, version 4.5.1.29). The synapse density was investigated using synaptophysin specific antibody staining (Neomarkers®) antibody marked by a biotinylated secondary antibody with VIP detection system (Vector®).

Treatment groups: 3 groups of Tg animals (15/group) and one group of non-transgenic C57BL6 animals (n=15):
(A) Tg animals receiving compound 6F6 at 17 mg/kg bw weekly (n=15)
(B) Tg animals receiving compound mIgG2a 17 mg/kg bw (n=15)
(D) Tg animals receiving compound 6F6 33 mg/kg bw (n=15)
(E) non-transgenic littermates; receiving mIgG2a 17 mg/kg bw (n=15)

Determination of Biochemical Amyloid Load in Sequentially Extracted Brain Homogenates and CSF CSF was collected from animals of treatment groups A, B and D and immediately frozen until ready for further analysis with ELISA technique. For the brain homogenates, frozen hemispheres from animals of groups A, B and D were homogenized in 5 ml TRIS buffered saline (TBS) containing protease inhibitor cocktail. Approximately half of the brain homogenates were immediately frozen in aliquots. The other half was centrifuged at 74.500 g for 1 hour and resulting supernatants (=TBS fraction), aliquoted and kept at −20° C.

until determination. The pellets were suspended in Triton X-100 (2.5 ml), centrifuged and the supernatants aliquoted and kept at −20° C. These steps were repeated with SDS (2.5 ml). The pellets of the SDS fraction were suspended in 70% formic acid (0.5 ml) prior to subsequent centrifugation. The obtained supernatants were neutralized with 1M TRIS (9.5 ml) aliquoted and kept at −20° C. CSF as well as samples of the four brain fractions were used for Aβ38, Aβ40 and Aβ42 determination using a commercially available kit (Mesoscale Discovery Abeta 3-plex kit #K15148E using Sector Imager MS2400), following the instructions of the manufacturer. Brain values were calculated as ng Aβ per g wet brain, CSF values were calculated as pg Aβ per ml.

In the TBS fraction, Aβ levels were lowest for animals of group B for all three amyloid species. For Aβ42 this increase of 6F6 treatment groups A and D was significant over control group B (p<0.05 vs. group A and p<0.001 vs. group D) but was non-significant for Aβ38 and Aβ40. In the Triton X-100 fractions mean Aβ42 levels were also significantly increased in 6F6 treatment groups A (p<0.05) and D (p<0.01) over control group B. Aβ40 levels of groups B and D did not differ significantly, whereas those of group A were still significantly increased compared to control group B (p<0.05). Although lacking significance, an increase of Aβ38 of 6F6 treatment group A over control group B was observed but 6F6 treatment group D was slightly reduced over control group B. Bound and water insoluble Aβ, as measured in SDS and FA fraction was significantly higher in brains of 6F6 treatment group A animals compared to groups B (Aβ38 and Aβ42) or D (Aβ 38 and Aβ 40). Control Group B and 6F6 treatment group D did not differ significantly.

In CSF samples no significant group differences for Aβ38, Aβ40 levels were observed. Aβ38, Aβ40 and Aβ42 levels were slightly lower in control group B animals compared to 6F6 treatment group A. CSF Aβ42 levels of 6F6 treatment group D animals were significantly increased compared to control group B (p<0.05) possibly indicating mobilisation of soluble Aβ42 through sequestration into the CSF or indirectly through the blood flow.

Determination of Synapse Density

Per animal three slices are stained with an anti-Synaptophysin antibody (1:200; Neo Markers; Cat# RM9111-SO) and biotinylated secondary antibody (1:200; Vector Laboratories; Cat# PK-6101) followed by a VIP development (substrate kit for peroxidase; Cat# SK4600). To determine an individual mean synapse density three images per region (granular layer from hippocampal CA1, CA3 and dentate gyrus medial blade (DGmb)) and slice are evaluated in a macro based measurement procedure. During the macro run, images are equally contrasted and synapses are counted above a constant threshold. Single and successional synapses are counted separately under the use of size restrictions. The total area of successional synapses is divided by the mean size of single synapses. The ultimate synapse count is calculated with following formula:

$$\sum \text{Synapses} = \text{number\_of\_discrete\_synapses} + \frac{\text{area\_of\_successional\_synpses}}{\text{mean\_area\_discrete\_synapses}}$$

Furthermore the image area is background corrected in terms of a reduction of the area of blood vessels, and the sum of synapses is considered relative to the total image area reduced by the area of blood vessels.

Measuring the synaptic counts in CA1, CA3 and GDmb region of the hippocampus brain sections taken from treatment groups A, B and D the synapse density remained unchanged among the treatment groups.

Determination of Longitudinal Plasma Levels of Total and Unbound (Free) Beta Amyloid In vivo blood samples were taken before start of treatment (day 0) and again in weeks 3, 6, 9 and 12 by mandibular sampling from the facial vein/artery. Blood samples were collected into EDTA and uncoated vials to obtain plasma. All plasma samples were frozen and stored until analysed.

Levels of unbound (free) amyloid and levels of total amyloid (unbound Aβ and complexed with antibody) were determined using Gyrolab™ workstation. Biotinylated 6F6 murine mAb was used as the capture reagent for the free β-amyloid assay and a biotinylated N-terminal specific anti-β-amyloid antibody (in house reagent) was used as the capture reagent for the total β-amyloid assay. Both capture reagents were captured on the Gyros Bioaffinity CD capture column containing a streptavidin coated matrix. Capture antibodies were added at a concentration of 700 nM. For both assays Alexa 647 labelled 4G8 (specific for the β-amyloid epitope 17-24) was used at a concentration of 12.5 nM for detection. To quantify the amount of β-amyloid in the samples an Aβ1-42 standard curve was prepared (Innogenetics Aβ1-42) to give a dynamic range of 31.25 pg/ml to 20000 pg/ml. Dilution of the Aβ1-42 standard curve and the plasma samples was carried out in β-amyloid-depleted human plasma. Data was analysed using the software inherent to the machine and then plotted in Excel.

Total β-amyloid levels increased over 2000-fold by week 3 (the first time point) in both the 17 mg/kg and 33 mg/kg 6F6 treatment groups. The 33 mg/kg treatment group had a slightly greater level of total β-amyloid level observed for the duration of the study but not correlated with the increased dose level possible indicating that the effect was reaching saturation. Free β-amyloid levels for both the 6F6 treatment groups was observed to be at background level shown by the non-transgenic mice by the first post treatment time point (3 weeks), presumably because most if not all of the β-amyloid detected with this assay was engaged in antibody-β-amyloid complexes. Without treatment intervention, base line levels for beta amyloid for the transgenic mice were approximately 6× higher than that of non-transgenic control mice.

Determination of Plaque Load Using 6E10 Staining

From brain halves of 18 Tg mice (6 of Tg group A; B and D) a sufficient number of slices per brain was prepared for quantification of amyloid deposition. 6E10 immunoreactivity was quantitatively evaluated in hippocampus and cortex. 15 sections per layer (altogether 5 layers corresponding to the FIGS. 104 to 105, 107 to 108, 111 to 112, 115 to 116 and 118 to 119 according to the morphology atlas "The Mouse Brain" from Paxinos and Franklin, 2nd Edition), each 5 μm thick (Leica SM 2000R) were cut sagittally. Tissues of all transgenic animals investigated were handled in exactly the same way to avoid bias due to variation of this procedure.

Figure 2:
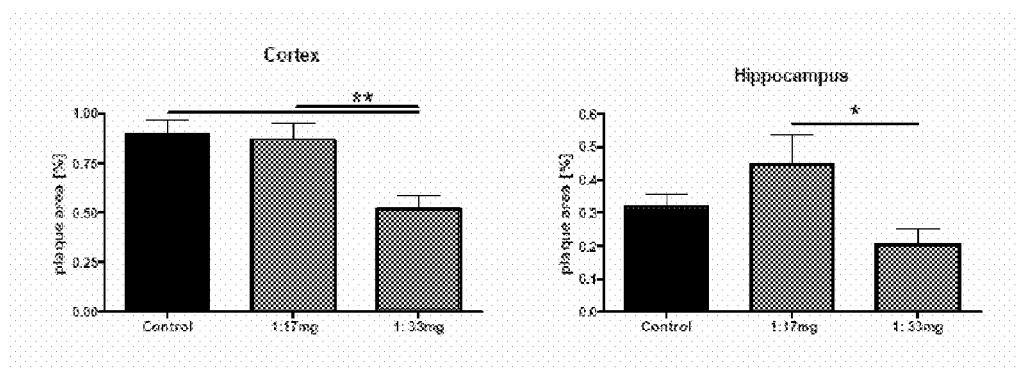
FIG. 2 shows bar charts showing the plaque load in transgenic hAPP mice brain sections of cortex and hippocampus after treatment with 17 mg/kg or 33 mg/kg 6F6 expressed in ortical plaque area % expressed as mean±standard error of mean.
Figure 3:
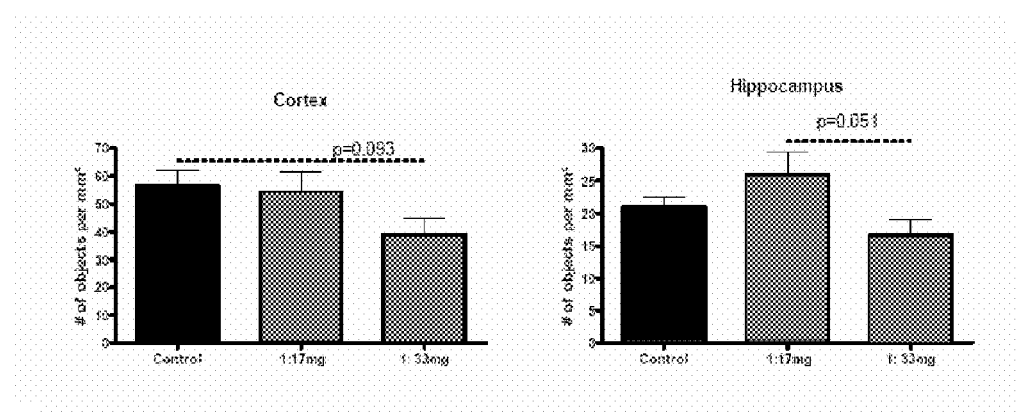
FIG. 3 shows bar charts showing the plaque load in transgenic hAPP mice brain sections of cortex and hippocampus after treatment with 17 mg/kg or 33 mg/kg 6F6 expressed in number of plaques per mm² expressed as mean±standard error of mean

Amyloid depositions and plaque load were determined using the monoclonal 6E10 antibody (Signet®) directed against position 1-17 of the human amyloid peptide. Measured region areas of the hippocampus and the cortex were constant throughout all investigated brains which excludes negative effects on tissue in immunohistochemical staining steps (e.g. shrinkage, different cutting circumstances etc) and indicates no treatment induced atrophy. Plaque load data were related to the individual region size in the slice to be able to cope with artifacts, folding or missing pieces. Treatment with high dose of 6F6 (group D), led to a significant decrease of the plaque area percentage in the hippocampus and cortex compared to the low dose 6F6 treatment (group A; ANOVA: cortex and hippocampus: p<0.01) and control group B (FIG. 2). The same tendency was given in the number of plaques per mm² which was again smaller in the 6F6 treatment group D compared to the control group B (t-test: cortex: p=0.093) and low dose 6F6 treatment group A (t-test: hippocampus: p=0.051; FIG. 3). The mean plaque size remained unchanged among all treatment groups.

Demonstration of Amyloidosis in the Eyes of Complement Factor H Deficient Mice: a Model of 'dry' AMD.

Animals

Ten-week-old, 3 month, 6 month, 9 month and one-year-old cfh$^{-/-}$ mice (n=6) (backcrossed onto the C57BL/6 genetic background for more than 10 generations) and age-matched normal C57BL/6 mice (n=6) were housed in a temperature-controlled environment with a 12-h day (160 lux)-night cycle and maintained on a normal lab diet, (fed lab chow ad libitum). Mice were anaesthetized (0.75 ml Ketamine, 0.5 ml Domitor, 0.75 ml sterile water at 0.2 ml/100 g, i.p. supplemented as necessary) and their pupils dilated with topical 1% tropicamide and 2.5% Phenylephrine hydrochloride 10-15 min before cSLO imaging. Before each image sequence, drops of Hydroxypropyl methylcellulose (0.3%) were placed on the eye to prevent drying. All experimental procedures complied with and were carried out under the United Kingdom Animals (Scientific Procedures) Act 1986.

Retinal Imaging

Imaging was performed on 3 month, 6 month and 12 month cfh$^{-/-}$ (n=12) and age-matched control (n=6) mice as described in detail below. High-resolution and high contrast retinal images were acquired with a confocal scanning laser opthalmoscope as described below. Briefly, reflectance imaging was performed by using 488- and 820-nm laser lines. Autofluorescence and fluorescein angiography images of the mouse retina were recorded by using 488-nm. Excitation and the built-in standard emission cut-off filter with the edge of the barrier (value of 50% transmission) at 498 nm.

Mice were anaesthetized (0.75 ml Ketamine, 0.5 ml Domitor, 0.75 ml sterile water at 0.2 ml/100 g, i.p. supplemented as necessary) and their pupils dilated with topical 1% tropicamide and 2.5% phenylephrine hydrochloride 10-15 min before imaging. Before each image sequence, a drop of hydroxypropyl methylcellulose (0.3%) was placed on the eye to prevent drying. High resolution and high contrast retinal images were acquired in vivo with a confocal scanning laser opthalmoscope (Heidelberg Retina Angiograph, Heidelberg Engineering, Heidelberg, Germany) using a modification of methods described (Guo L, Salt T E, Maass A, Luong V, Moss S E, Fitzke F W, Cordeiro M F (2006) *Invest Opthalmol V is Sci* 47:626-633). Briefly, the pinhole diameter had been reduced to 100 µm to improve axial resolution and laser power increased to improve signal-to-noise ratio. Power at the mouse pupil was measured to be 1400 W at 488 nm. The mouse was fitted with a specially designed plano-concave contact lens and optical power was provided using a 50× microscopic lens with an extra-long working distance, which improved optical resolving power and allowed detection of micro-capillary structures as small as 3 µm in diameter. Tomographic image stacks were recorded where the axial plane was sequentially moved at 15-µm intervals, vitreal-to-scleral and central-to-peripheral to visualize retinal vasculature from the primary plexus through to the outer plexus. All image sequences were captured at 8.9 Hz, 100 field-of-view, and were digitized as 8-bit, 768 768-pixel image files, resulting in a lateral image resolution of 1.2 µm/pixel. Axial resolution in the mouse eye was measured to be 5-8 µm.

Differences between the cfh$^{-/-}$ and age-matched control animals in the number of subretinal autofluorescent deposits at the level of the RPE were analyzed by applying the Student unpaired t test on the image data using SPSS (Chicago, Ill.).

Histology and Immunohistochemistry

Briefly, animals were deeply anesthetized with ketamin and dormitor and then ten-week-old cfh$^{-/-}$ mice (n=6), 3 month (n=3), 6 month (n=3) 9 month (n=3) and 1-year-old cfh$^{-/-}$ mice (n=6) were perfused with 0.1 M PBS, followed by 4% paraformaldehyde (in 0.1 M PBS, pH 7.2). Eyes were removed and placed in 4% paraformaldehyde before cryoprotection in 30% sucrose solution (in 0.1 M PBS buffer) and left for 24 h at 4° C. The lens was removed through a corneal incision, and the eyes were rapidly frozen in OCT compound and sectioned at a thickness of 10 µm for immunohistochemical analysis, see details below. The neural retina and choroid of selected animals were separated and flat-mounted independently.

Ocular sections from cfh$^{-/-}$ mice (n=20) and age-matched control (n=20) mice were incubated with primary antibodies, (Table 5) followed by the appropriate fluorescently conjugated secondary antibodies and DAPI to stain the nuclei, see below for detail.

Immunohistochemistry was performed at room temperature and was undertaken on 10 µm thick cryostat sections from eyes fixed in 4% paraformaldehyde. Retinal sections were blocked for 1 hr in 5% normal donkey serum in 0.1M phosphate buffer saline (PBS), pH 7.4 with 0.3% Triton X-100, and incubated overnight with primary antibodies, diluted with 1% normal donkey serum in 0.1M PBS with 0.3% Triton X-100. Dilutions of each primary antibody were as described below. Primary antibody exposure was followed by washing, and where required, fluorescently conjugated appropriate secondary antibodies (Santa Cruz, Biotechnology, Inc., donkey anti mouse sc-2099 made up in PBS with 0.3% Triton and 2% normal serum (1:100 dilution, same diluent as the primary) and the sections were exposed for 2 hours, (FITC Santa Cruz, Biotechnology, Inc., donkey anti mouse sc-2099). Negative controls consisted of both an unrelated isotype matched antibody or omission of the primary antibody. Nuclei were subsequently stained with 0.5 ml 4',6-diamidino-2-phenylindole (1 µl of DAPI stock solution to 5 ml of 0.1M PBS; Sigma-Aldrich) for 1 min. Slides were then washed several times with 0.1 M PBS followed by four washes in Tris buffer saline (pH 7.4) and finally glass coverslips were mounted in VECTASHIELD (Vector Laboratories).

Sections were viewed and images captured on either a laser scanning confocal microscope (Leica SP2; Leitz) at 8 bit/channel and 1024×1024 px, or an Epi-fluorescence brightfield microscope (Olympus BX50F4, Olympus, Japan), where data was captured as 24 bit colour images at 3840× 3072 px resolution using Nikon DXM1200 (Nikon, Tokyo, Japan) digital camera.

Commercially Available Primary Antibodies

C3 (FITC-conjugated goat anti-mouse 1:100 dilution; ICN Biomedicals) was used for staining retinal sections at the dilutions indicated.

Anti-Amyloid Beta Antibodies Used in this Work:
(1) Covance SIG-39153 Rabbit polyclonal Ab specific for rodent amyloid beta, recommended for use in IHC paraffin embedded sections @ 1/250 dilution,
(2) Calbiochem NE1002 (4G8) Mouse monoclonal Ab, (IgG2b), recognising both human and mouse amyloid beta, recommended for use in IHC paraffin embedded sections @ 1/100-1/1000 dilution, (formic acid pretreatment required), (3) Abcam ab2539 Rabbit polyclonal Ab recognising both human and mouse amyloid beta, recommended for use in IHC paraffin embedded sections @ 1/100 dilution, (requires heat mediated antigen retrieval before IHC staining procedure), Commercially Available Secondary Antibodies

TABLE 5

Commercially available secondary Abs used in this work

| Donkey anti-mouse FITC IgG | Santa Cruz Biotech inc. | sc-2099 | 1:300 |
| Donkey anti rabbit FITC IgG | Santa Cruz Biotech inc. | sc-2090 | 1:300 |
| Alexa Fluor 488 fragment of goat anti-mouse IgG | Invitrogen | A11017 | 1:2000 |

Detection of Drusenoid-Like Deposits in cfh$^{-/-}$ Mice.

Autofluorescing deposits can be detected in the retinae of aged cfh$^{-/-}$ mice. The fluorescent lipid, drusenoid-like deposits can first be detected at around 14 weeks of age in cfh$^{-/-}$ mice and their presence increase with age and are located in the subretinal space (apical side of RPE). These deposits are also present in wild-type mice, but to a significantly lesser degree. For example, a cSLO image of the retina of a 6-month-old cfh$^{-/-}$ mouse identifies some autofluorescent white spots on a grey background and these can be seen in an in vitro retinal spread for IHC at 10× and at 40× magnification, as easily identifiable autofluorescing deposits in the green (FITC) channel. There are large variations of fluorescence emission spectra among the autofluorescing deposits, (data not shown).

When sections of the retina of cfh−/− mice are examined by IHC autofluorescing, drusenoid-like deposits can be seen associated with sites of complement C3 deposition in the subretinal space on the apical side of the RPE cells. This can be seen in 12-month-old cfh$^{-/-}$ mice, (data not shown).

Analysis of CFH−/− Mouse Eyes with Commercially Available Anti-Amyloid Beta Abs.

Commercially available sections of fixed Human Alzheimer's brains confirmed positive for Aβ staining (Abcam ab4582), were used to check the cross-reactivity of three commercially available anti-amyloid beta Abs shown in Table 6.

The procedure used for this was:
For Brain Paraffin Sections:
1. Xylene—10 mins
2. 100% Ethanol—8 mins
3. 95% Ethanol—5 mins
4. Distilled water—5 mins
5. Antigen Retrieval;
    Ab2539 HIER with Citrate Buffer
    NE1002(4G8)—70% Formic Acid
    SIG-39153
For Both Paraffin and Frozen Sections;
6. Wash with PBS, 3 times for 5 mins each
7. Block with 5% Normal Donkey Serum for 1 hour
8. Wash briefly with PBS
9. Apply primary antibody at;
    Ab 2539—1:100
    NE1002 (4G8)—1:200
    SIG-39153—1:250
Incubate Overnight
10. Wash with PBS, 3 times at 5 mins each
11. Apply secondary antibody at
    For ab2539—Ab sc-2090 1/100
    For NE1002—Ab sc-2099 1/100
    For SIG-39153—Ab sc-2090 1/100
Incubate for 1 Hour
12. Wash with PBS, 3 times for 5 mins each
13. DAPI for 1 min
12. Wash with PBS, 3 times
13. Wash with TBS, 4 times at 5 mins each
14. Mount, coverslip and seal.

As expected only the primary antibodies able to cross-react with human beta amyloid (NE1002 [4G8], and ab2539), gave positive detection of human amyloid beta plaques in human Alzheimer's brain tissue, (data not shown).

Detection of Amyloid Beta in the Eyes of Aged (>1 Year Old) and 10 Week Old Mice CFH−/− Using Commercially Available Abs.

TABLE 6

Primary amyloid beta antibodies used in this study

| Rabbit Polyclonal to Beta Amyloid | AbCam Ltd. | ab2539 | 1:100 |
| Anti-β-Amyloid Mouse mAb | Calbiochem Inc. | NE1002 | 1:100 |
| Purified Polyclonal Antibody against Rodent Aβ | Covance Inc. | SIG-39153 | 1:100 |

Figure 4:
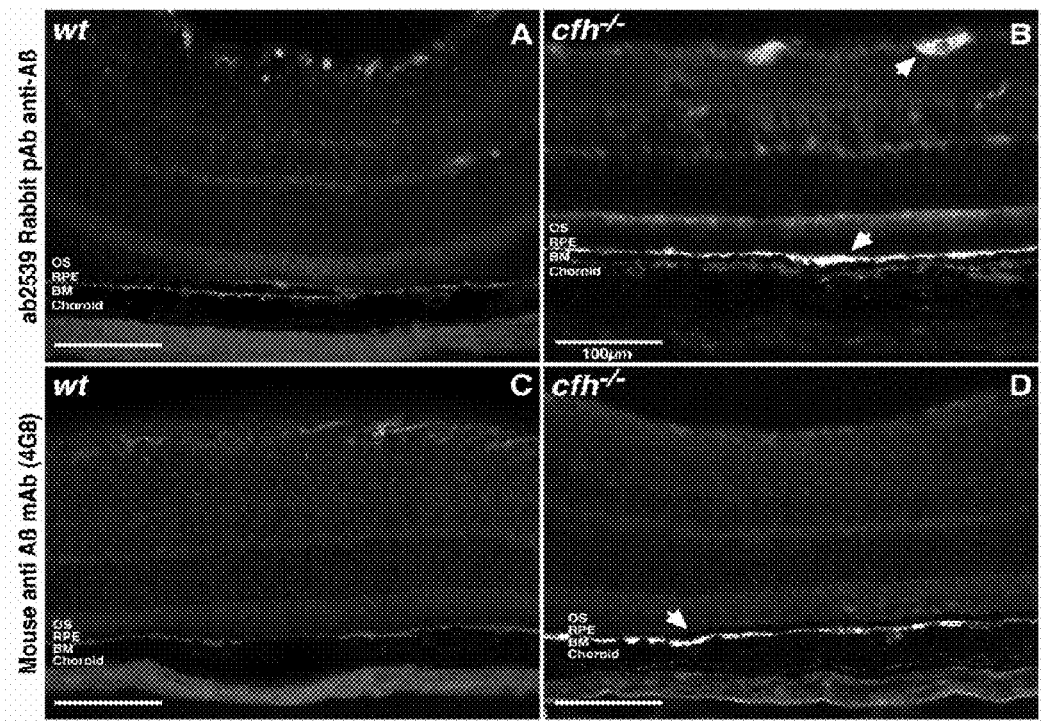
FIG. 4 shows the detection of amyloid beta in the retina of aged CFH −/− mice

The following procedure was followed:
1. Air dry the slides for several hours
2. Wash 3 times
3. Block with 5% NDS for 1 hour
4. Prepare Primary antibodies from Table 6 as follows;
    a. SIG39153-1:250
    b. NE1002 (4G8)-1:200
    c. Ab2539 1:500
5. Wash briefly and incubate with the primary antibodies overnight
6. Wash 3 times
7. Prepare the secondary antibodies as follows;
    a. anti-rabbit FITC
    b. anti-mouse FITC
incubate for 1 hour
8. Wash 3 times
9. Apply DAPI for 1 min
10. wash 3 times with PBS
11. Wash 4 times with TBS
12. Mount, coverslip and seal Initially fixed retinal eye tissue from age-matched cfh$^{-/-}$ mice and wild type litter mate controls, (C57Bl/6) of 12-13 months of age were examined using the three commercially available anti-amyloid beta primary antibodies, (Ab), described above. Each primary Ab was detected using the relevant secondary fluorescent labelled secondary Ab. For the Ab SIG39153, no signal could be detected in either tissue despite following the manufacturer's recommended protocol, (as in the brain samples described above), (data not shown). However, amyloid beta could be specifically detected in the retina of aged cfh$^{-/-}$ mice, (but not wild type litter mates), using both of the other commercially available anti-amyloid beta primary antibodies. An example of this data is shown in FIG. 4, where panel (A) shows retinal tissue from an aged wild-type mouse and panel (B) shows tissue from an aged cfh$^{-/-}$ mouse both probed with ab2539 as the primary Ab; and panel (C) shows retinal tissue from an aged wild-type mouse and panel (D) shows tissue from an aged cfh$^{-/-}$ both probed with NE1002 (4G8) as the primary Ab. The data demonstrates that amyloid-beta is deposited around Bruch's membrane specifically in aged cfh$^{-/-}$ mice. The positive signal of cross-reactivity of the antibodies to deposited amyloid beta at the RPE/Bruch's membrane interface can be seen as an intense white stripe highlighted by the white arrows in FIGS. 4 (B) and (D). Some amyloid deposition can also be seen in the area of the nerve fibre layer and ganglion cells of the eye of cfh-/- mice for example, the white signal highlighted with a white arrow at the top of FIG. 4 (B)

Subsequently, fixed retinal eye tissue from 10 week-old, age-matched cfh$^{-/-}$ mice and wild type litter mate controls, (C57Bl/6) were examined using both NE1002 (4G8) and ab2539 anti-amyloid beta primary antibodies. Again, amyloid beta could be specifically detected in the retina of the cfh$^{-/-}$ mice, but not wild type litter mates, (data not shown). The data demonstrated that amyloid beta deposition occurs in 10% of the retina in 10 week-old cfh$^{-/-}$ mice (n=3), (data not shown). Deposition is largely on the basal side of the retinal pigment epithelial layer, (RPE) and appears associated with basal laminar deposits, (data not shown). Note that the amyloid beta deposition at 10 weeks of age is similar to the time at which the 'drusenoid' auto-fluorescent deposits, and the complement C3 deposits, first appear in the cfh -/- mouse.

Cross-Reactivity of 6F6 with Amyloid Beta in the Retina of Cfh$^{-/-}$ Mouse Eyes Primary Antibodies Used in this Study.
    (i) 6F6 mouse monoclonal Ab, IgG2a,
    (ii) Mouse IgG2a isotype control monoclonal Ab, (in house reagent specific for cytosine deaminase antigen,
    (iii) Mouse IgG2a, kappa [MOPC-173] isotype control monoclonal Ab, (ab18413, Abcam), Balb/c myeloma derived clone of unknown specificity The following procedure was followed:
1. Air dry the slides for several hours
2. Wash with 1×PBS, 3 times at 5 mins each
3. Block with 5% Normal Donkey Serum in 0.3% Triton X-100 in PBS, incubate for 1 hours at Room temperature
4. Prepare primary antibody, diluting with 1% Normal Donkey Serum in 0.3% Triton X-100 in PBS
    a. Mouse monoclonal Amyloid Beta 6F6 i)—1:1000, 1:2000 and 1:4000
    b. Mouse IgG2a control ii) 1:1000, 1:2000 and 1:4000
Wash Briefly
5. Apply the primary antibody and incubate overnight at room temperature
Next Day;
1. Wash with 1×PBS, 3 times at 5 mins each
2. Prepare the secondary antibodies by diluting in 1% Normal Donkey Serum in 0.3% Triton X-100 in PBS
    a. Goat anti-mouse Alexa Fluor 488 (1:2000)
Apply the Secondary antibody and incubate for 1 hour at RT
3. Wash with 1×PBS, 3 times at 5 mins each
4. Apply DAPI, 1:5000 in PBS and incubate for 1 min in the dark
5. Wash with 1×PBS, 3 times for 5 mins each
6. Wash with 1×TBS, 4 times at 5 mins each
7. Mount with Vectashield, coverslip and seal.

Initially fixed retinal eye tissue from age-matched cfh$^{-/-}$ mice and wild type litter mate controls, (C57Bl/6) of 12-13 months of age were examined as outlined above. Although there was cross-reactivity of 6F6 to a similar area of the retina to that detected by commercial anti-amyloid beta Abs, there was similar cross-reactivity with the control antibody though some of this may be due to background cross-reactivity of the secondary Ab alone. Some background staining could also be seen in wild-type samples.

In order to resolve the background staining described above, the experiment was repeated, but the secondary antibody was switched from an Alexa Fluor 488 labelled anti-mouse IgG Ab, to a FITC labelled molecule. Also the primary control antibody was switched to a commercially available isotype control (iii).

The procedure used for this experiment was:
Air dry the slides for several hours
Wash with 1×PBS, 1 time at 5 mins
Block with 5% Normal Donkey Serum in 0.3% Triton X-100 in PBS, incubate for 1 hours at Room temperature
Prepare primary antibody, diluting with 1% Normal Donkey Serum in 0.3% Triton X-100 in PBS
    a) Mouse IgG2a, Kappa ab18413 1:100
Wash briefly
Apply the primary antibody and incubate overnight at room temperature
Next Day;
Wash with 1×PBS, 3 times at 5 mins each
Prepare the secondary antibodies by diluting in 1% Normal Donkey Serum in 0.3% Triton X-100 in PBS
    b) Donkey anti mouse FITC (1:300)
Apply the Secondary antibody and incubate for 1 hour at RT
Wash with 1×PBS, 3 times at 5 mins each
Apply DAPI, 1:5000 in PBS and incubate for 1 min in the dark
Wash with 1×PBS, 3 times for 5 mins each
Wash with 1×TBS, 4 times at 5 mins each
Mount with Vectashield, coverslip and seal.

Figure 5:
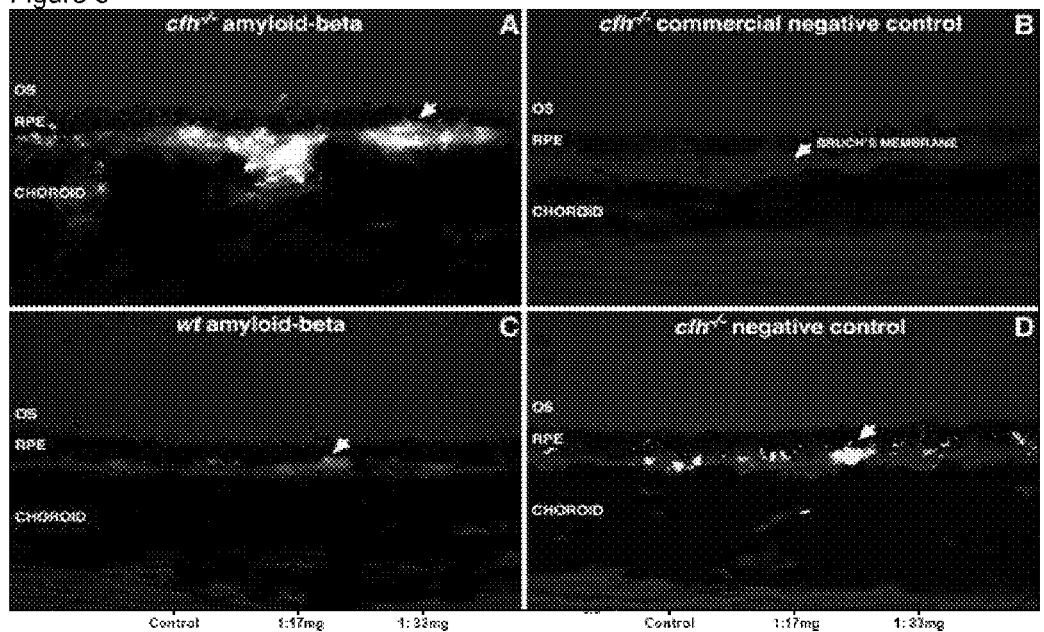
FIG. 5 shows cross-reactivity of 6F6 to amyloid beta in the retina of aged CFH−/− mice

An example of the data obtained with the above staining procedure is shown in FIG. 5. Panel (A) shows data obtained using 6F6 as a primary at 1 in 4000 dilution to stain a section of the retina of an aged cfh$^{-/-}$ mouse and panel (B) shows data obtained using isotype control (iii) as a primary, (at a similar w/v dilution as 6F6), to stain a section of the retina of an aged cfh$^{-/-}$ mouse (labelled cfh-/- commercial negative control), and panel (C) shows data obtained using 6F6 as a primary at 1 in 4000 dilution to stain a section of the retina of an age-matched wild type control mouse and panel (D) shows data obtained using isotype control (ii) (labelled cfh-/- negative control) as a primary at 1 in 4000 dilution to stain a section of the retina of an aged cfh$^{-/-}$ mouse.

The data confirms that 6F6 is able to specifically detect amyloid beta deposited in the retina of cfh$^{-/-}$ mice, (FIG. 5A), not present in age-matched wild-type mice, (FIG. 5 C). The specificity of 6F6 was confirmed by the complete absence of staining using a commercially available isotype control as a primary, at a similar w/v dilution as 6F6, (FIG. 5 B). The data obtained using another in house isotype control antibody (ii)) at 1 in 4000 dilution (FIG. 5 D), suggested specific retinal staining in cfh$^{-/-}$ mice. However, this maybe explained by the specificity of this isotype matched antibody since cytosine deaminase is a marker for cellular breakdown which could well be occurring in the retina of aged cfh$^{-/-}$ mice. In retrospect this was not an appropriate choice for an isotype specific Ab control in this experiment.

Time Course of Cross-Reactivity of Amyloid in the Retina of cfh-/- Mouse Eyes to 6F6 and 4G8.

Age-matched C57Bl/6, (wild-type) and cfh-/- mice were similarly analysed by immunohistochemistry at intermediate time points between those of 10 weeks and 12 months: 3 months old (n=3) 6 months old (n=3) and 9 months old (n=3). Analysis was performed using either 6F6 or Calbiochem NE1002 (4G8) as the primary detection antibody. At three months of age, little difference could be seen between wild-type and cfh−/− mice at a gross level. However, by six months of age; amyloid deposition could clearly be detected around the border of Bruch's membrane and the retinal pigment epithelial (RPE) cells in cfh −/− mice but not in age-matched wild type control mice, (data not shown). At the six month time point, the staining using 4G8 seemed to cover the whole border between RPE and BM, whereas the similar staining using 6F6 as the primary antibody was more punctuate, (data not shown). The six month of age time-point showed a clear distinction by IHC of the level of amyloid deposition in the retina in cfh−/− mice compared to age-matched wild type controls.

In summary cfh$^{-/-}$ mice represent a rapid model of amyloidosis in the eye, especially the retina and this could be closely linked to the model's 'dry' AMD phenotype. The mice would represent a good model for analysis of the effect of therapeutic anti-amyloid beta Abs such as 6F6 on amyloid beta in the retina.

Demonstration of Ability of 6F6 to Interfere with Amyloid Beta Binding to Complement Factor 1.

The recently published data showing the direct interaction between amyloid beta and complement factor 1, (CFI), the 'partner' and co-factor for complement factor H, (CFH), (Wang, J. et al., 2008), could help to explain the rapid amyloid beta deposition in the retina of cfh$^{-/-}$ mice. In the absence of CFH, amyloid beta would be free to bind to any 'un-partnered' CFI in the mouse retina, (Wang, J. et al., 2008, unpublished data). To demonstrate that the therapeutic anti-amyloid beta antibody, 6F6, or a humanised equivalent, could interfere with the interaction between amyloid beta and CFI by binding to amyloid beta; a series of experiments could be performed similar to those described by Wang, J. et al., 2008. The effect of pre-incubation of 6F6 with commercially available preparations of amyloid beta protein, (eg. from Peptide Institute), on its ability to bind commercially available CFI protein, (Quidel Corporation), in the presence and absence of commercially available CFH protein, (Quidel Corporation) could be determined as described, (Wang, J. et al., 2008, p 716-717), and analysed either by standard co-immunoprecipitation studies and/or by BiaCore analysis. Similarly, the ability of 6F6 antibody to disrupt a pre-formed amyloid beta: CFI complex in the presence and absence of CFH could be ascertained by co-immunoprecipitation studies and/or by BiaCore analysis. Similarly the effect of pre-incubation of 6F6 with commercially available preparations of amyloid beta protein, (eg. from Peptide Institute), on its ability to affect the function of commercially available CFI protein, (Quidel Corporation), in the presence of commercially available CFH protein, (Quidel Corporation) could be measured using a complement C3b, (Quidel Corporation) cleavage assay as described, (Wang, J. et al., 2008, p 717), and analysed by standard SDS PAGE. Similarly, the ability of 6F6 antibody to disrupt a pre-formed amyloid beta: CFI complex in the presence of CFH and thereby restore C3b cleavage function to the CFI/CFH complex could be ascertained as described, (Wang, J. et al., 2008, p 717), and analysed by standard SDS PAGE.

The results from the recently published in vitro study were suggested to support a hypothesis where amyloid beta activates the complement system within drusen by blocking the function of complement factor I leading to a low-grade, chronic inflammation in sub-retinal tissues; thus linking four of the factors associated with the development of AMD: inflammation, complement activation, amyloid beta deposition and drusen, (Wang, J. et al., 2008). Such direct evidence for the effect of amyloid beta in activating the alternative complement pathway by potentially competing with complement factor H for binding to complement factor I has not previously been documented, (Wang, J. et al., 2008). Interference with the negative effect of amyloid beta on the clearance of activated complement C3 components by therapeutic administration of an antibody such as 6F6 could constitute a novel mechanism of action in halting or reversing AMD.

Detection of Amyloid Beta Deposition in Aged Human Eyes Using Thioflavin T Staining and 6F6 Crossreactivity Samples of human donor eye tissue were obtained from Moorfields Eye Bank, Moorfields Eye Hospital, London, UK. The first sample obtained was that of a 65 year old Caucasian man, (Moorfields Eye Bank, Moorfields Eye Hospital, London, UK). The eyes were fixed and processed as described previously and sections were subject to staining with thioflavin T, (Sigma T3516), using a previously published protocol, (Anderson et al., Exp Eye Res (2004), 78; 243-256; Levine, H, Methods in Enzymology (1999), 309; 274-284. The thioflavin T staining data generated with the eye tissue showed a fluorescent signal from Thioflavin T bound amyloid beta which could be seen as a wispy white stain around the basal laminar deposits and Drusen around the RPE Bruch's membrane interface in the human outer retina of the eye tissue.

Further samples of human donor eye tissue were obtained from Moorfields Eye Bank, Moorfields Eye Hospital, London, UK, including those from a 41 year old and a 90 year old man. These eyes were again fixed and processed as described previously, but this time sections were subject to staining with 6F6 as the primary antibody and visualised by using a FITC conjugated anti-mouse IgG secondary antibody, as described previously. Although the 90 year old eye sample had lost most of the retina during processing, amyloid cross-reactivity to 6F6, could be detected in the outer segments of the remaining tissue. This staining was not present in either the outer segments or the retina of the eye from the 41 year old male. The human donors of the eye tissue had not been formally diagnosed with AMD but the presence of heavy basal laminar deposits and also their association with amyloid beta strongly suggest the etiology of early dry AMD in the thioflavin T stained eye tissue from the 65 year old male. Although in the sample of a 90 year old eye the tissue processing had lost most of the retina, the fact that amyloid cross-reactivity to 6F6 could be detected in the remaining tissue but not in either the outer segments nor the retina of the eye from a 41 year old male, (envisaged to be too young to have the symptoms of AMD), bodes well for the use of 6F6-like antibodies in binding the amyloid found in aged human eyes.

Cloning of Hybridoma Variable Regions
Variable Region Sequences

Total RNA was extracted from all hybridoma cell lines and heavy and light variable domain cDNA sequences were then generated by reverse transcription and polymerase chain reaction (RT-PCR). The forward primer for RT-PCR was a mixture of degenerate primers specific for murine immunoglobulin gene leader-sequences and the reverse primer was specific for the antibody constant regions, so for example for 6F6 murine isotype IgG2a for the heavy chain and murine kappa for the light chain. Primers were designed according to the strategy described by Jones and Bendig (Bio/Technology 9:88, 1991). RT-PCR was carried out in duplicate for both V-region sequences to enable subsequent verification of the correct V-region sequences. The V-region products generated by RT-PCR were cloned (Invitrogen TA Cloning Kit) and sequence data obtained.

6F6 V_H Amino Acid Sequence (SEQ ID No: 19)
EVQLQQSGAELVEPGASVKLSCTGSGFNIK<u>VYYVH</u>WLKQLTEQGLEWIG<u>R</u>
<u>IDPENGETIYTPKFQD</u>KATLTVDTSSNTAYLQLSSLTSEDAAVYYCVS<u>SG</u>
<u>YWGQGTTLTVSS</u>

6F6 V_H DNA Sequence (SEQ ID No: 20)
GAGGTTCAGCTGCAGCAGTCTGGGGCAGAGCTTGTGGAGCCAGGGGCCTC

AGTCAAGTTGTCCTGCACAGGTTCTGGCTTCAACATTAAGGTCTACTATG

TGCACTGGCTGAAGCAGTTGACTGAGCAGGGCCTGGAATGGATTGGAAGG

ATTGATCCTGAAAATGGTGAAACTATATATACCCCGAAATTCCAGGACAA

GGCCACTTTGACAGTAGACACATCATCCAACACAGCCTACCTGCAGCTCA

GCAGCCTGACATCTGAGGACGCTGCCGTGTACTATTGTGTTAGTTCGGGC

TACTGGGGCCAAGGCACCACTCTCACAGTCTCCTCA

6F6 V_L Amino Acid Sequence (SEQ ID No: 21)
DIVMTQSAFSNPVTLGTSASISC<u>RSSKSLLHRNGITYLY</u>WYLQKPGQPPQ
LLIY<u>QMSNLAS</u>GVPDRFTSSGSGTDFTLKISRVEAEDVGVYYC<u>AQNLELW</u>
<u>TFGGGTKLEIK</u>

6F6 V_L DNA Sequence (SEQ ID No: 22)
GATATTGTGATGACGCAGTCTGCATTCTCCAATCCAGTCACTCTTGGAAC

ATCAGCTTCCATCTCCTGCAGGTCTAGCAAGAGTCTCCTACATAGGAATG

GCATCACCTATTTGTATTGGTATCTGCAGAAGCCAGGCCAGCCTCCTCAA

CTCCTGATTTATCAGATGTCCAACCTTGCCTCAGGAGTCCCAGACAGGTT

CACTAGCAGTGGGTCAGGAACTGATTTCACTCTGAAAATCAGCAGAGTGG

AGGCTGAGGATGTGGGTGTTTATTACTGTGCTCAAAATCTAGAACTTTGG

ACGTTCGGTGGAGGCACCAAGCTGGAAATCAAA

2C1 V_H Amino Acid Sequence (SEQ ID No: 31)
EVQLQQSGAELVKPGASVKLSCTGSGFNIK<u>VYYVH</u>WLKQLTEQGLEWIG<u>R</u>
<u>IDPENGETIYAPKFQD</u>KATLTVDTSSNTAYLQLSSLTSEDTAVYYCVS<u>SG</u>
<u>YWGQGTTLTVSS</u>

2C1 V_H DNA Sequence (SEQ ID No: 32)
GAGGTTCAGCTACAGCAGTCTGGGGCAGAGCTTGTGAAGCCAGGGGCCTC

AGTCAAGTTGTCCTGCACAGGTTCTGGCTTCAACATTAAGGTCTACTATG

TGCACTGGCTGAAGCAGTTGACTGAGCAGGGCCTGGAATGGATTGGAAGG

ATTGATCCTGAAAATGGTGAAACTATATATGCCCCGAAATTCCAGGACAA

GGCCACTTTGACAGTAGACACATCATCCAACACAGCCTACCTGCAGCTCA

GCAGCCTGACATCTGAGGACACTGCCGTCTATTATTGTGTTAGTTCGGGC

TACTGGGGCCAAGGCACCACTCTCACAGTCTCCTCA

2C1 V_L Amino Acid Sequence (SEQ ID No: 33)
DIVMTQSAFSNPVTLGTSASISC<u>RSSKSLLHRNGITYLY</u>WYLQKPGQSPQ
LLIY<u>QMSNLAS</u>GVPDRFTSSGSGTDFTLKISRVEAEDVGVYYC<u>AQNLELW</u>
<u>TFGGGTKLEIK</u>

2C1 V_L DNA Sequence (SEQ ID No: 34)
GATATTGTGATGACGCAGTCTGCATTCTCCAATCCAGTCACTCTTGGAAC

ATCAGCTTCCATCTCCTGCAGGTCTAGCAAGAGTCTCCTACATAGGAATG

GCATCACCTATTTGTATTGGTATCTGCAGAAGCCAGGCCAGTCTCCTCAG

CTCCTGATTTATCAGATGTCCAACCTTGCCTCAGGAGTCCCAGACAGGTT

CACTAGCAGTGGGTCAGGAACTGATTTCACTCTGAAAATCAGCAGAGTGG

AGGCTGAGGATGTGGGTGTTTATTACTGTGCTCAAAATCTAGAACTTTGG

ACGTTCGGTGGAGGCACCAAGCTGGAAATCAAA

2E11 V_H Amino Acid Sequence (SEQ ID No: 35)
EVQLQQSGAEVVKPGASVKLSCTASGFNIK<u>VYYIH</u>WLKQLTEQGLEWIG<u>R</u>
<u>IDPENGETKYVPKFQG</u>KATLTVDTSSNTAYLHLSSLTSEDTGVYYCVT<u>SG</u>
<u>YWGQGTTLTVSS</u>

2E11 V_H DNA Sequence (SEQ ID No: 36)
GAGGTTCAGCTGCAGCAGTCTGGGGCAGAGGTTGTGAAGCCAGGGGCCTC

AGTCAAGTTGTCCTGCACAGCTTCTGGCTTCAACATTAAAGTCTACTATA

TCCACTGGTTGAAGCAGTTGACTGAGCAGGGCCTAGAATGGATTGGAAGG

ATTGATCCTGAAAATGGTGAAACTAAGTATGTCCCGAAATTCCAGGGCAA

GGCCACTTTAACAGTAGACACATCCTCCAACACAGCCTACCTGCACCTCA

GCAGCCTGACATCTGAGGACACTGGCGTCTATTACTGTGTTACCTCGGGC

TACTGGGGCCAAGGCACCACTCTCACAGTCTCCTCA

2E11 V_L Amino Acid Sequence (SEQ ID No: 37)
DIVMTQAAFSNPVALGTSASISC<u>RSSKSLLHSNGITYLY</u>WYLQKPGQSPQ
LLIY<u>QMSNLAS</u>GVPDRFSSSGSGTDFTLRISRVEAEDVGVYYC<u>AQNLELW</u>
<u>TFGGGTKLEIK</u>

2E11 V_L DNA Sequence (SEQ ID No: 38)
GATATTGTGATGACGCAGGCTGCATTCTCCAATCCAGTCGCTCTTGGAAC

ATCAGCTTCCATCTCCTGCAGGTCTAGTAAGAGTCTCCTACATAGTAATG

GCATCACTTATTTGTATTGGTATCTGCAGAAGCCAGGCCAGTCTCCTCAG

CTCCTGATTTATCAGATGTCCAACCTTGCCTCAGGAGTCCCAGACAGGTT

CAGTAGCAGTGGGTCAGGAACTGATTTCACACTGAGAATCAGCAGAGTGG

AGGCTGAGGATGTGGGTGTTTATTACTGTGCTCAAAATCTAGAACTTTGG

ACGTTCGGTGGAGGCACCAAGCTGGAAATCAAA

4D4 V_H Amino Acid Sequence (SEQ ID No: 39)
EVQLQQSGAELVEPGASVKLSCTGSGFNIK<u>VYYVH</u>WLKQLTEQGLEWIG<u>R</u>
<u>IDPENGETLYTPKFQG</u>KATLTVDTSSNTAYLQLNSLTSEDTAVYYCVS<u>SG</u>
<u>YWGQGTSLTVSS</u>

4D4 V_H DNA Sequence (SEQ ID No: 40)
GAGGTTCAGCTGCAGCAGTCTGGGGCAGAGCTTGTGGAGCCAGGGGCCTC

AGTCAAGTTGTCCTGCACAGGTTCTGGCTTCAACATTAAGGTCTACTATG

TTCACTGGCTGAAGCAGTTGACTGAGCAGGGCCTGGAATGGATTGGAAGG

ATTGATCCTGAGAATGGTGAAACTCTATACACCCCGAAATTCCAGGGCAA

GGCCACTTTGACAGTAGACACATCATCCAACACAGCCTACCTGCAGCTCA

ACAGCCTGACATCTGAGGACACTGCCGTCTATTATTGTGTTAGTTCGGGC

TACTGGGGCCAAGGCACCTCTCTCACAGTCTCCTCA

4D4 V_L Amino Acid Sequence (SEQ ID No: 41)
DIVMTQSAFSNPVTLGTSASISC<u>RSSKSLLHRNGITYLY</u>WYLQKPGQSPQ
LLIY<u>QMSNLAS</u>GVPDRFTSSGSGTDFTLKISRVEAEDVGVYYC<u>AQNLELW</u>
<u>TFGGGTKLEIK</u>

4D4 V_L DNA Sequence (SEQ ID No: 42)
GATATTGTGATGACGCAGTCTGCATTCTCCAATCCAGTCACTCTTGGAAC

ATCAGCTTCCATCTCCTGCAGGTCTAGCAAGAGTCTCCTACATAGGAATG

GCATCACCTATTTGTATTGGTATCTGCAGAAGCCAGGCCAGTCTCCTCAG

CTCCTGATTTATCAGATGTCCAACCTTGCCTCAGGAGTCCCAGACAGGTT

CACTAGCAGTGGGTCAGGAACTGATTTCACTCTGAAAATCAGCAGAGTGG

AGGCTGAGGATGTGGGTGTTTATTACTGTGCTCAAAATCTAGAACTTTGG

ACGTTCGGTGGAGGCACCAAGCTGGAAATCAAA

5C9 V_H Amino Acid Sequence (SEQ ID No: 43)
EVQLQQSGAEFVRPGASVKLSCTASGFNIK<u>TYYIH</u>WLKQRTDQGLEWIG<u>R</u>

<u>IDPEDGETKFGPKFRG</u>KATLTADTSSNTASLQLSSLTSEDTGVYYCVT<u>SG</u>

<u>YWGQGTTLSVSS</u>

5C9 V_H DNA Sequence (SEQ ID No: 44)
GAGGTTCAGCTGCAGCAGTCTGGGGCAGAGTTTGTGAGGCCAGGGGCCTC

AGTCAAGTTATCCTGCACAGCTTCTGGCTTCAACATTAAAACCTACTATA

TACACTGGCTGAAACAGAGGACTGACCAGGGCCTGGAGTGGATTGGAAGG

ATTGATCCGAGGATGGTGAAACTAAATTTGGCCCGAAATTCCGGGCAA

GGCCACTTTAACAGCAGACACATCCTCCAACACAGCCTCCCTACAACTCA

GCAGTCTGACATCTGAGGACACTGGCGTCTATTACTGTGTTACCTCGGGC

TACTGGGGCCAAGGCACCACTCTCTCAGTCTCCTCA

5C9 V_L Amino Acid Sequence (SEQ ID No: 45)
DIVMTQAAFSNPVTLGTSASISC<u>RSSKSLLHSNGITYLY</u>WYLQKPGQSPQ LLIY<u>QMSNLAS</u>GVPDRFSSSGSGTDFTLRISRVEAEDVGVYYC<u>AQNLELW</u>

<u>TFGGGTKLEIK</u>

5C9 V_L DNA Sequence (SEQ ID No: 46)
GATATTGTGATGACGCAGGCTGCATTCTCCAATCCAGTCACTCTTGGAAC

ATCAGCCTCCATCTCCTGCAGGTCTAGTAAGAGTCTCCTACATAGTAATG

GCATCACTTATTTGTATTGGTATCTGCAGAAGCCAGGCCAGTCTCCTCAG

CTCTTGATTTATCAGATGTCCAACCTTGCCTCAGGAGTCCCAGACAGGTT

CAGTAGCAGTGGGTCAGGAACTGATTTCACACTGAGAATCAGCAGAGTGG

AGGCTGAGGATGTGGGTGTTTATTACTGTGCTCAAAATCTAGAACTTTGG

ACGTTCGGTGGAGGCACCAAGCTGGAAATCAAA

5D1 V_H Amino Acid Sequence (SEQ ID No: 47)
EVQLQQSGAELVKPGASVKLSCTGSGFNIK<u>VYYVH</u>WLKQLTEQGLEWIG<u>R</u>

<u>IDPENGETKYAPKFQD</u>KATLTVDTSSNTAYLHLSSLTSEDTAVYYCVS<u>SG</u>

<u>YWGQGTTLTVSS</u>

5D1 V_H DNA Sequence (SEQ ID No: 48)
GAGGTTCAGCTGCAGCAGTCTGGGGCAGAGCTTGTGAAGCCAGGGGCCTC

AGTCAAGTTGTCCTGCACAGGTTCTGGCTTCAACATTAAGGTCTACTATG

TGCACTGGCTGAAGCAGTTGACTGAGCAGGGCCTGGAATGGATTGGAAGG

ATTGATCCTGAAAATGGTGAAACTAAATATGCCCCGAAATTCCAGGACAA

GGCCACTTTGACAGTAGACACATCCTCCAATACAGCCTACCTTCACCTCA

GCAGCCTGACATCTGAGGACACTGCCGTCTATTATTGTGTTAGTTCGGGC

TACTGGGGCCAAGGCACCACTCTCACAGTCTCCTCA

5D1 V_L Amino Acid Sequence (SEQ ID No: 49)
DIVMTQSAFSNPVTLGTSASISC<u>RSSKSLLHRNGITYLY</u>WYLQKPGQSPQ LLIY<u>QMSNLAS</u>GVPDRFTSSGSGTDFTLKISRVEAEDVGVYYC<u>AQNLELW</u>

<u>TFGGGTKLEIK</u>

5D1 V_L DNA Sequence (SEQ ID No: 50)
GACATTGTGATGACGCAGTCTGCATTCTCCAATCCAGTCACTCTTGGAAC

ATCAGCTTCCATCTCCTGCAGGTCTAGTAAGAGTCTCCTACATAGGAATG

GCATCACCTATTTGTATTGGTATCTGCAGAAGCCAGGCCAGTCTCCTCAG

CTCCTGATTTATCAGATGTCCAACCTTGCCTCAGGAGTCCCAGACAGGTT

CACTAGCAGTGGGTCAGGAACTGATTTCACTCTGAAAATCAGCAGAGTGG

AGGCTGAGGATGTGGGTGTTTATTATTGTGCTCAAAATCTAGAACTTTGG

ACGTTCGGTGGAGGCACCAAGCTGGAAATCAAA

14B3 V_H Amino Acid Sequence (SEQ ID No: 51)
EVQLQQSGAELVEPGASVKLSCTGSGFNIK<u>VYYVH</u>WLKQLTEQGLEWIG<u>R</u>

<u>IDPENGETLYTPKFQG</u>KATFTVDTSSNTAYLQLSSLTSEDTAVYYCVS<u>SG</u>

<u>YWGQGTTLTVSS</u>

14B3 V_H DNA Sequence (SEQ ID No: 52)
GAGGTTCAGCTGCAGCAGTCTGGGGCAGAGCTTGTGGAGCCAGGGGCCTC

AGTCAAGTTGTCCTGCACAGGTTCTGGCTTCAACATTAAGGTCTACTATG

TTCACTGGCTGAAGCAGTTGACTGAGCAGGGCCTGGAATGGATTGGAAGG

ATTGATCCTGAGAATGGTGAAACTCTATATACCCCGAAATTCCAGGGCAA

GGCCACTTTTACAGTAGACACATCATCCAACACAGCCTACCTGCAGCTCA

GCAGCCTGACATCTGAGGACACTGCCGTCTATTATTGTGTTAGTTCGGGC

TACTGGGGCCAAGGCACCACTCTCACAGTCTCCTCA

14B3 V_L Amino Acid Sequence (SEQ ID No: 53)
DIVMTQSAFSNPVTLGTSASISC<u>RSSKSLLHRNGITYLY</u>WYLQKPGQSPQ LLIY<u>QMSNLAS</u>GVPDRFTSSGSGTDFTLKISRVEAEDVGVYYC<u>AQNLELW</u>

<u>TFGGGTKLEIK</u>

14B3 V_L DNA Sequence (SEQ ID No: 54)
GATATTGTGATGACGCAGTCTGCATTCTCCAATCCAGTCACTCTTGGAAC

ATCAGCTTCCATCTCCTGCAGGTCTAGCAAGAGTCTCCTACATAGGAATG

GCATCACCTATTTGTATTGGTATCTGCAGAAGCCAGGCCAGTCTCCTCAG

CTCCTGATTTATCAGATGTCCAACCTTGCCTCAGGAGTCCCAGACAGGTT

CACTAGCAGTGGGTCAGGAACTGATTTCACTCTGAAAATCAGCAGAGTGG

AGGCTGAGGATGTGGGTGTTTATTACTGTGCTCAAAATCTAGAACTTTGG

ACGTTCGGTGGAGGCACCAAGCTGGAAATCAAA

16D4 V_H Amino Acid Sequence (SEQ ID No: 55)
EVQLQQSGAELVKPGASVKLSCTASGFNIK<u>DYYMH</u>WLKQLTEQGLEWIG<u>R</u>

<u>IDPENGETQYAPKFQG</u>KASLTADTSSNTAYLHLSSLTSEDTAVYYCVS<u>SG</u>

<u>YWGQGTTLTVSS</u>

16D4 V_H DNA Sequence (SEQ ID No: 56)
GAGGTTCAGCTGCAGCAGTCTGGGGCAGAGCTTGTGAAGCCAGGGGCCTC

AGTCAAGTTGTCCTGCACAGCTTCTGGCTTCAACATTAAAGACTACTATA

TGCACTGGTTGAAGCAGTTGACTGAGCAGGGCCTGGAATGGATTGGAAGG

ATTGATCCTGAAAATGGTGAAACTCAATATGCCCCGAAATTCCAGGGCAA

-continued
GGCCTCTTTAACAGCAGACACATCCTCCAACACAGCCTACCTTCACCTCA

GCAGCCTGACATCTGAGGACACTGCCGTCTATTACTGTGTTAGTTCGGGC

TACTGGGGCCAAGGCACCACTCTCACAGTCTCCTCA

16D4 V_L Amino Acid Sequence (SEQ ID No: 57)
DIVMTQAAFSNPVTLGTSASISCRSSKSLLHSNGITYLYWYLQKPGQSPQ

LLIYQMSNLASGVPDRFSSSGSGTDFTLRISRVEAEDVGVYYCAQNLELW

TFGGGTKLEIK

16D4 V_L DNA Sequence (SEQ ID No: 58)
GATATTGTGATGACGCAGGCTGCATTCTCCAATCCAGTCACTCTTGGAAC

ATCAGCTTCCATCTCCTGCAGGTCTAGTAAGAGTCTCCTACATAGTAATG

GCATCACTTATTTGTATTGGTATCTGCAGAAGCCAGGCCAGTCTCCTCAG

CTCCTGATTTATCAGATGTCCAACCTTGCCTCAGGAGTCCCAGACAGGTT

CAGTAGCAGTGGGTCAGGAACTGATTTCACACTGAGAATCAGCAGAGTGG

AGGCTGAGGATGTGGGTGTTTATTACTGTGCTCAAAATCTAGAACTTTGG

ACGTTCGGTGGAGGCACCAAGCTGGAAATCAAA

Complementarity Determining Regions (CDRs) are underlined in the amino acid sequences.

Cloning and Expression of 6F6 Chimera

A chimeric 6F6 antibody (6F6c) consisting of the parent murine V regions grafted on to human IgG1 for the heavy chain or human C kappa regions for the light chain was generated in order to express recombinant antibody material that could be used to confirm the correct cloning of functional murine V regions. DNA encoding 6F6 murine heavy and light chain V regions and a murine signal sequence (Kabat et al "Sequences of Immunological Interest", NIH, 1991, Fifth edition, p. 30 95VNP'CL) were cloned in frame into the mammalian expression vectors RLD-bshe (for the heavy chain) and RLN-bshe (for the light chain) already containing human constant regions (IgG1 Fc disabled or human C kappa, respectively). Through the introduction of a suitable cloning site the amino acid sequence in FR4 (Framework Region 4 (V-region sequence following CDR3 and preceding first constant domain)) of the V_H amino acid sequence was changed from TTLTVSS as shown in Seq ID19 to TLVTVSS.

Elements of RLD-bshe Expression Vector for Heavy Chain Expression:

| Base Pairs | Description of DNA segment |
| --- | --- |
| 0-1014 | Promoter (SV40/RSV) |
| 1015-2442 | Antibody heavy chain |
| 2443-2765 | Poly A |
| 2766-3142 | BG Promoter |
| 3239-3802 | DHFR |
| 3803-4162 | Poly A |
| 4163-6322 | Total backbone |
| 5077-5937 (complementary strand) | Beta lactamase |

(position of elements and overall size of vector given above are for illustration purposes only and will depend upon the size of the antibody chain insert)

Elements of RLN-bshe Expression Vector for Light Chain Expression:

| Base Pairs | Description of DNA segment |
| --- | --- |
| 0-1014 | Promoter (SV40/RSV) |
| 1015-1731 | Antibody light chain |
| 1732-2051 | Poly A |
| 2388-2764 | BG Promoter |
| 2774-3568 | Neomycin |
| 3569-3876 | Poly A |
| 3877-6063 | Total backbone |
| 5077-5937 (complementary strand) | Beta lactamase |

(position of elements and overall size of vector given above are for illustration purposes only and will depend upon the size of the antibody chain insert)

Clones with correctly cloned $V_H$ and $V_L$ sequences were identified and plasmids prepared for expression in CHO cells. Expressed 6F6c antibody was purified from cell culture supernatant by protein A chromatography on a FPLC system, and then tested for binding to Aβ by ELISA and SPR using Biacore™ technology. The results indicated that the correct 6F6 mouse V regions were cloned and expressed, resulting in a functional antibody with similar characteristics to the parent murine antibody 6F6.

Heavy Chain Humanisation Strategy

For the 6F6 mouse variable heavy chain sequence a human germ line acceptor framework was selected (IGHV1-24, SEQ. I.D. NO:13) which had 58% identity (including CDRs) with the mouse 6F6 variable heavy chain sequence (SEQ ID No:19) together with the JH4 minigene (Kabat: YFDY-WGQGTLVTVSS (SEQ ID No:15)). The first four residues of the JH4 minigene residues fall within the CDR3 region which is replaced by the incoming CDR from the donor antibody.

A panel of 34 humanised variable heavy chain variants were generated on the basis of sequence comparison and possible impact on antibody function. The 6F6 murine heavy chain CDRs (using the Kabat definition) (SEQ ID Nos: 1, 2 and 3) were grafted into the human acceptor framework selected above. A number of humanised variable heavy chain variants were designed comprising substitutions at two to fifteen positions chosen from positions 1, 5, 13, 24, 27, 28, 29, 30, 37, 40, 41, 48, 66, 67, 69, 71, 75, 76, 93 and 94 (Kabat numbering) (Table 7). Positions 93 and 94 immediately adjacent to the Kabat definition of CDRH3 were included in all variants studied.

TABLE 7

List of $V_H$ backmutations investigated

| Kabat Numbering of residue | Human Framework Residue (donor IGHV1-24) | Corresponding residue in murine 6F6 |
| --- | --- | --- |
| 1 | Q | E |
| 5 | V | Q |
| 13 | K | E |
| 24 | V | G |
| 27 | Y | F |
| 28 | T | N |
| 29 | L | I |
| 30 | T | K |
| 37 | V | L |
| 40 | A | L |
| 41 | P | T |
| 48 | M | I |
| 66 | R | K |
| 67 | V | A |
| 69 | M | L |
| 71 | E | V |
| 75 | T | S |
| 76 | D | N |
| 93 | A | V |
| 94 | T | S |

Light Chain Humanisation Strategy

For the 6F6 mouse variable light chain sequence a human germ line acceptor framework was selected (IGKV2-28) which had 79% identity (including CDRs) with the mouse 6F6 variable light chain sequence (SEQ ID No:21) together with the J-region kappa 1 (Kabat: WTFGQGTKVEIK) based on sequence similarity. The first two residues of the JK-1 minigene residues fall within the CDR3 region and are identical to the last two residues in the mouse 6F6 light chain CDR3.

The 6F6 murine light chain CDRs (using the Kabat definition) (SEQ ID Nos: 4, 5 and 6) were grafted into the human acceptor framework selected above to give a variable straight graft light chain L0. A panel of 13 humanised variable light chain variants were further generated on the basis of sequence comparison and possible impact on antibody function. Humanised variable light chain variants were designed comprising substitutions at one to four positions chosen from positions; 8, 11, 43, 63, 64, 100 and 104 (Kabat numbering) (Table 8).

TABLE 8

List of $V_L$ backmutations investigated

| Kabat Numbering of residue | Human Framework Residue (donor IGHV1-24) | Corresponding residue in murine 6F6 |
|---|---|---|
| 8 | P | A |
| 11 | L | N |
| 43 | S | P |
| 63 | S | T |
| 64 | G | S |
| 100 | Q (JK-1) | G |
| 104 | V (JK-1) | L |

Construction of Humanised Heavy and Light Chain DNA

Humanised V regions were synthesised de novo by build up of overlapping oligos and PCR amplification or by site directed mutagenesis using existing variants as template. Restriction sites for cloning into mammalian expression vectors RLD-bshe and RLN-bshe and a murine signal sequence (Kabat et al "Sequences of Immunological Interest", NIH, 1991, Fifth edition, p. 30 95VNP'CL) were included. The PCR products encoding the humanised V regions together with signal sequences and restriction sites were then cloned in frame into mammalian expression vectors: Heavy chain variants were cloned into RLD-bshe to generate DNA encoding full length human IgG1 Fc mutated heavy chains; Light chain variants were cloned in frame into RLN-bshe containing the DNA encoding human kappa constant region to generate DNA encoding full length human kappa light chains.

Representative Examples of Expression of Humanised Heavy and Light Chain Antibody Combinations CHOK1 cells were transiently transfected at small scale initially for assessing combinations of humanised light and heavy chain DNA constructs in 6-well plates. CHOK1 cells passaged in DMEM F12, with 5% ultra low IgG foetal bovine serum and 2 mM glutamine were grown to confluency in 6-well plates. The confluent cells were transfected with a total of 7.5 µg DNA: 30 pg transfection lipid (for a suitable lipid see WO2006/053783) in Optimem GLUTAMAX medium (Invitrogen). Transfected cells were incubated at 37° C. with 5% $CO_2$. At 72 hours supernatants were harvested and assayed for antibody concentration and then tested for binding to human Aβ by ELISA.

Humanized antibodies were also expressed in large scale by co-transfection of RLD and RLN plasmids encoding the heavy and light chains into CHO cells by electroporation. A stable polyclonal population of cells expressing the appropriate antibody were selected using a nucleoside-free media. Antibody was recovered and purified from the supernatant by FPLC with PROSEPA HiTrap columns.

Assessment of Humanised $V_H$ Variants in β-Amyloid Binding ELISA 34 humanised $V_H$ variants expressed in small scale 6-well cultures were assessed for binding to human Aβ peptide (1-40). All 34 heavy chains were tested in combination with the L2 light chain (see Table 8 below). Some combinations with L2 did express antibody material but did not bind to β-amyloid 1-40 and therefore no EC50 values could be generated for these combinations. Where EC50 values could be generated they varied between experiments but ranged from an about 30-fold increased EC50 values to identical values when compared to the EC50 value of the chimeric construct using the 6F6 murine V-regions which was contained in each experiment as a reference. Residues 93 and 94 immediately adjacent to the Kabat definition of CDRH3 were maintained in all humanised variants. Positions 27-30 which can be considered, in structural terms, part of CDRH1 (Chothia and Lesk (1987) J. Mol. Biol. 196(4):901-917) gave better binding when backmutated than substitutions at 93 and 94 alone. Back mutation at both residues 24 and 37 together were required to give robust binding, without either one of these residues, humanised variants did not efficiently bind to Aβ peptide (1-40) in this ELISA format and when combined with L2 light chain. Table 9 shows the best humanised $V_H$ variants in terms of amyloid binding properties based on combination with L2 light chain.

TABLE 9

Selected humanised $V_H$ variants

| | Kabat Number | | | | | | | | | | | | | | | | | | | |
|---|---|---|---|---|---|---|---|---|---|---|---|---|---|---|---|---|---|---|---|---|
| | 1 | 5 | 13 | 24 | 27 | 28 | 29 | 30 | 37 | 40 | 41 | 48 | 66 | 67 | 69 | 71 | 75 | 76 | 93 | 94 |
| | | | | | | | | | | 6F6 | | | | | | | | | | |
| VH humanised | E | Q | E | G | F | N | I | K | L | L | T | I | K | A | L | V | S | N | V | S |
| | | | | | | | | | | IGHV1-24 | | | | | | | | | | |
| Variant | Q | V | K | V | Y | T | L | T | V | A | P | M | R | V | M | E | T | D | A | T |
| H11 | — | — | E | G | F | N | I | K | L | L | — | I | K | A | L | V | — | — | V | S |
| H21 | — | — | — | G | F | N | I | K | L | L | — | — | — | — | — | — | — | — | V | S |
| H23 | — | — | — | G | F | N | I | K | L | — | — | I | — | — | — | — | — | — | V | S |
| H24 | — | — | — | G | F | N | I | K | L | — | — | — | — | — | — | — | S | N | V | S |
| H25 | — | — | — | G | F | N | I | K | L | — | — | I | — | — | L | — | — | — | V | S |
| H26 | — | — | — | G | F | N | I | K | L | — | — | I | — | — | L | — | S | — | V | S |
| H27 | — | — | E | G | F | N | I | K | L | — | — | — | K | A | — | V | — | — | V | S |
| H28 | — | — | E | G | F | N | I | K | L | — | — | — | K | A | L | V | — | — | V | S |
| H29 | — | — | — | G | F | N | I | K | L | — | — | — | K | A | L | V | — | — | V | S |

"—" means residue remained unchanged from IGHV1-24 acceptor framework sequence

Assessment of Humanised $V_L$ Variants in β-Amyloid Binding ELISA

Humanised L0 and $V_L$ variants expressed in small scale 6-well cultures were assessed for binding to human Aβ peptide (1-40). All variants were tested in combination with H11. Table 10 summarises all functional $V_L$ variants generated.

TABLE 10

Selected humanised $V_L$ variants

| | Kabat Number | | | | | | |
|---|---|---|---|---|---|---|---|
| | 8 | 11 | 43 | 63 | 64 | 100 | 104 |
| | | | | 6F6 | | | |
| VL humanised | A | N | P | T | S | G | L |
| | | | | IGKV-2-28 | | | |
| Variant | P | L | S | S | G | Q | V |
| L0 | — | — | — | — | — | — | — |
| L2 | — | — | — | — | S | — | — |
| L3 | — | — | P | — | — | — | — |
| L4 | — | — | — | T | — | — | — |
| L5 | — | — | — | — | — | G | L |
| L6 | — | — | P | T | — | G | L |
| L7 | — | — | P | — | S | — | — |
| L8 | — | — | P | T | — | — | — |
| L9 | — | N | — | — | S | — | — |
| L10 | A | — | — | — | S | — | — |
| L11 | — | — | — | — | S | G | — |
| L12 | — | N | P | — | — | — | — |
| L13 | A | — | P | — | — | — | — |
| L14 | — | — | P | — | — | G | — |

The best $V_H$ variant H11 heavy chain combinations with light chains L2 and L9, L10, L12 and L13 were examined more closely. For these experiments purified antibody material generated in suspension CHO cells was used. Results of two independent experiments with two different coating concentrations of Aβ peptide (1-40) are shown below in Table 11.

TABLE 11

EC50 values for humanised variants binding to Aβ peptide (1-40)

| | 0.1 μg/ml Aβ 1-40 Exp 1 | 0.5 μg/ml Aβ 1-40 Exp 1 | 0.1 μg/ml Aβ 1-40 Exp 2 | 0.1 μg/ml Aβ 1-40 Exp 3 |
|---|---|---|---|---|
| 6F6c | 0.085 (pred) ± 0.009 | 0.06 ± 0.003 | 0.043 ± 0.002 | 0.048 ± 0.003 |
| H11L2 | 0.205 ± 0.008 | 0.119 ± 0.005 | 0.102 ± 0.004 | 0.068 ± 0.004 |
| H11L9 | 0.09 ± 0.009 | 0.061 ± 0.002 | 0.051 ± 0.002 | 0.04 ± 0.002 |
| H11L10 | 0.148 ± 0.004 | 0.071 ± 0.002 | 0.054 ± 0.002 | 0.056 ± 0.001 |
| H11L12 | 0.189 ± 0.011 | 0.06 ± 0.003 | 0.055 ± 0.003 | 0.058 ± 0.002 |
| H11L13 | 0.224 ± 0.008 | 0.064 ± 0.002 | 0.056 ± 0.002 | 0.061 ± 0.002 |

Concentrations refer to Aβ-peptide used to coat the microtiter plates; values shown are from duplicate wells and SD for each pair are shown Competition ELISA for Binding to Human β-amyloid 1-40 in Solution 6F6c and humanised antibodies $H_{11}L2$, H11L9, H11L10, H11L12 and H11L13 were assessed for their ability to bind Aβ1-40 peptide in solution and inhibit the interaction of human Aβ1-40 peptide with mouse 6F6 monoclonal antibody in a competition ELISA. A constant concentration of biotinylated β-amyloid 1-40 was pre-incubated with serial diluted amounts of humanised 6F6 antibody variants. The mixture including complexed and free amyloid was then added to wells containing immobilised mouse 6F6 monoclonal antibody and incubated for 15 minutes at room temperature. Plates were washed and the amount of free β-amyloid that was still available for binding the immobilised parental 6F6 monoclonal antibody was then detected using streptavidin-HRP conjugate.

Table 12 shows the IC50 values of this competition for two independent experiments using purified antibody material. All humanised variants were able to effectively compete for binding to 6F6 parental monoclonal antibody with very similar IC50 values.

TABLE 12

IC50 values for competition of humanised variants for binding of human β-amyloid 1-40 with 6F6 monoclonal antibody by ELISA

| Humanised variant | Exp 1 | | Exp 2 | |
|---|---|---|---|---|
| | IC50 μg/ml | Std Error | IC50 μg/ml | Std Error |
| 6F6c | 0.566 | 0.027 | 0.451 | ±0.013 |
| H11L2 | 0.862 | 0.024 | 0.578 | ±0.024 |
| H11L9 | 0.588 | 0.018 | 0.518 | ±0.028 |
| H11L10 | 0.622 | 0.041 | 0.519 | ±0.016 |
| H11L12 | 0.561 | 0.025 | 0.549 | ±0.018 |
| H11L13 | 0.616 | 0.015 | 0.531 | ±0.023 |

Binding Kinetics of Humanised Variants Determined by Surface Plasmon Resonance Assay The affinity of selected heavy and light chain combinations was determined using a Biacore T100 instrument. Three independent experiments were performed using humanised antibody immobilised via protein A surface Biacore chips and injection of β-amyloid 1-40 peptides. The chimeric molecule of 6F6 served as a reference molecule. For this Protein A was immobilised on a CM5 chip by primary amine coupling in accordance with manufactures recommendations. Anti-β-amyloid antibodies were captured on this surface and after a period of stabilisation human β-amyloid 1-40 was passed over at concentrations 256-2 nM in halving dilutions. A buffer injection over the captured antibody surface was used to double reference the data set in accordance with Biacore best practice. Mild acidic regeneration conditions chosen removed captured antibody but did not significantly affect the ability of the Protein A surface to perform another capture event. The work was carried out in HBS-EP at 25° C. Results are summarised in Table 13 as the mean of all three experiments.

TABLE 13

Biacore affinity and kinetic data for selected purified humanised antibody variants

| Antibody construct | Mean KD [nM] | SD |
|---|---|---|
| 6F6c | 3.74 | 1.20 |
| H11L2 | 9.57 | 2.31 |
| H11L9 | 4.91 | 1.25 |
| H11L10 | 5.57 | 1.66 |

TABLE 13-continued

Biacore affinity and kinetic data for selected purified humanised antibody variants

| Antibody construct | Mean KD [nM] | SD |
|---|---|---|
| H11L12 | 6.95 | 2.34 |
| H11L13 | 7.41 | 2.39 |

Data shows mean KD and SD of three independent experiments

Epitope Fine Mapping of Humanised Antibody H11L9

The minimal binding epitope of the humanised monoclonal antibody H11L9 was fine mapped using SRU BIND plate reader (SRU Biosystems). Three peptide sets were generated, based on an 18 amino acid sequence for fine mapping of the epitope: a) an alanine scanning peptide set for which 10 of the residues 27-37 were replaced consecutively with an alanine residue; b) a set of N-terminally truncated peptides where one residue was removed successively from the N-terminus of the 18-mer peptide starting with residue 23 and c) a set of C-terminally truncated peptides where one residue was removed successively from the C-terminus of the 18-mer peptide starting with residue 40.

All peptides were generated in the following format; Biotin-SGSG linker-PEPTIDE-amide, the linker was lengthened where necessary to ensure that all peptides were 22-mers.

A streptavidin coated biosensor plate (SRU Biosystems) was washed with PBS and spun upside down to remove buffer and then washed with PBS, 0.1% tween 20 and 0.4% acetonitrile and spun upside down to remove residual buffer. Wells were resuspended in 100 ul of PBS, 0.1% tween 20 and 0.4% acetonitrile and read on the SRU plate reader to establish a baseline. 50 ul of the buffer was then removed and 50 ul of diluted peptide added and allowed to bind. The plate was then washed with PBS twice and then resuspended in 100 ul of PBS and the baseline re-measured. Once the baseline stabilised 50 ul of buffer was removed and H11L9 and a control antibody were added to final concentration of 30 ug/ml. Binding of the antibodies was monitored. Plates were washed twice with PBS and resuspended in 100 ul of PBS, and the plates were re-measured and referenced back to the addition of antibody to look for weak binders that would be removed by the washing step. The washed plate binding levels were taken and analysed for antibody binding to the various peptide set.

N-terminal deletion of the region showed no effect on binding when residues D23 to N27 were deleted sequentially. Deletion of K28 caused a reduction of binding by over 50% but deletion of residues G29 to A30 did not reduce binding further. Deletion of residue I31 and beyond completely abolished binding. This defined the N-terminal boundary as requiring K28 for full binding. C-terminal deletion of the region showed no effect on binding when residues V40 to L34 were deleted one by one. However, binding was completely abolished by deleting position G33 and beyond. This defined the C-terminal border as requiring at least residue G33 for binding. Therefore, the N- and C-terminal deletion data taken together fine mapped H11L9 to the minimal epitope KGAIIG, residues 28-33, within the beta-amyloid peptide. This confirms the earlier overlapping peptide epitope mapping with monoclonal antibody 6F6 except that elimination of residue M35 appeared to cause a drop of binding signal with 6F6.

Alanine replacement scanning from residues N27 to G37 showed that replacement of amino acids I32 and in particular G33 with alanine had the largest impact on binding. This data also confirmed the C-terminal deletion data above that G33 seemed to be crucial for binding of this antibody. Results are summarised in Table 14 in schematic form.

TABLE 14

Schematic summary of epitope fine mapping for H11L9

| Residue # in beta amyloid | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|
| Amino Acid | D | V | G | S | N | K | G | A | I | I | G | L | M | V | G | G | V | V |
| Alanine Scanning | | | | | | | | | | | | | | | | | | |
| N-terminal truncation > | | | | | | | | | | | | | | | | | | |
| C-terminal truncation < | | | | | | | | | | | | | | | | | | |

- Residue not investigated in peptide set
- No impact on binding (similar to that of full 18-mer)
- Reduced binding
- Removal of residue results in loss of binding
- Assessment not possible De-Immunisation of Humanised Antibody H11L9

In silico assessment of potential Th-cell epitopes was performed and selected residues in the amino acid sequence of the heavy chain variable and the light chain variable domain (SEQ ID No:24 and SEQ ID No:26 respectively) were replaced with alternative residues in order to destroy these epitopes whilst preserving functionality. Positions 23, 30, 31, 38, 42, 61 and 95 for Vh and residues 11, 30, 52 and 53 for VL were replaced with the alternative amino acids shown in Tables 15 and 16 for each position.

TABLE 15

Selected amino acid replacements in humanised Vh H11

| Vh humanised | Kabat Number | | | | | | |
|---|---|---|---|---|---|---|---|
| | 23 | 30 | 31 | 38 | 42 | 61 | 95 |
| | | | | H11 | | | |
| Variant | K | K | V | R | G | P | S |
| H36 | T | — | — | — | — | — | — |
| H37 | — | H | — | — | — | — | — |
| H38 | — | — | T | — | — | — | — |
| H39 | — | — | — | Q | — | — | — |
| H40 | — | — | — | — | E | — | — |
| H41 | — | — | — | — | — | Q | — |
| H42 | — | — | — | — | — | — | R |
| H43 | T | H | T | Q | E | Q | R |

TABLE 15-continued

Selected amino acid replacements in humanised Vh H11

| Vh humanised | Kabat Number | | | | | | |
|---|---|---|---|---|---|---|---|
| | 23 | 30 | 31 | 38 | 42 | 61 | 95 |
| | | | | H11 | | | |
| Variant | K | K | V | R | G | P | S |
| H44 | T | H | T | Q | E | Q | — |
| H45 | — | H | T | — | — | — | — |
| H46 | T | H | — | — | — | — | — |
| H47 | T | — | — | — | E | — | — |
| H48 | — | H | — | — | E | — | — |
| H49 | — | — | T | — | E | — | — |
| H50 | T | H | — | — | E | — | — |
| H51 | — | H | T | — | E | — | — |

TABLE 16

Selected amino acid replacements in humanised $V_L$ L9

| VL humanised | Kabat Number | | | |
|---|---|---|---|---|
| | 11 | 30 | 52 | 53 |
| | | L9 | | |
| Variant | N | I | S | N |
| L15 | — | K | — | — |
| L16 | — | — | D | — |
| L17 | — | — | — | H |
| L18 | L | K | D | H |
| L19 | — | K | D | H |
| L20 | — | — | D | H |
| L21 | — | K | D | — |
| L22 | — | K | — | H |

The V regions were synthesised by de novo build up of overlapping oligos and PCR amplification as described above or by site directed mutagenesis using the H11 and L9 heavy and light chain variants as templates. Restriction sites for cloning into mammalian expression vectors RLD-bshe and RLN-bshe and a murine signal sequence (Kabat et al "Sequences of Immunological Interest", NIH, 1991, Fifth edition, p. 30 95VNP'CL) were included. The products encoding the modified V regions were then cloned into mammalian expression vectors: Heavy chain variants were cloned into RLD-bshe with the pEF promoter to generate DNA encoding full length human IgG1 Fc mutated heavy chains; Light chain variants were cloned in frame into RLN-bshe with the pEF promoter containing the DNA encoding human kappa constant region to generate DNA encoding full length human kappa light chains.

Initially, new Vh variants H36-H44 were expressed and assessed in combination with L9 light chain and new VL variants L15-L18 were expressed and assessed in combination with H11 heavy chain. Expressed antibodies were assayed for binding to synthetic beta amyloid 1-40 using expression culture supernatant and ELISA and Biacore analysis. Following this assessment, the single changes that best retained binding potency were combined generating heavy and light chain constructs H45-H51 and L19-L22. These new chain variants were again expressed in combination with the partner chains H11 and L9 as outlined above. From this second set of variants, the best heavy (H48-H51) or light chains (L19-L21) were combined with each other to generate a third set which was again expressed and investigated by Biacore for binding kinetics to beta amyloid 1-40. Table 17 shows those combinations and the binding kinetics

TABLE 17

Selected set of humanised de-immunised contructs and binding kinetics (Biacore)

| Constructs | ka | kd | KD (nM) |
|---|---|---|---|
| H48L19 | 1.474E+5 | 4.643E-4 | 3.15 |
| H49L19 | 1.549E+5 | 4.780E-4 | 3.09 |
| H50L19 | 1.333E+5 | 3.682E-4 | 2.76 |
| H51L19 | 1.405E+5 | 3.717E-4 | 2.65 |
| H48L20 | 1.024E+5 | 2.065E-4 | 2.02 |
| H49L20 | 9.967E+4 | 2.223E-4 | 2.23 |
| H50L20 | 8.486E+4 | 2.122E-4 | 2.50 |
| H51L20 | 9.646E+4 | 2.149E-4 | 2.23 |
| H48L21 | 1.453E+5 | 2.922E-4 | 2.01 |
| H49L21 | 1.405E+5 | 3.621E-4 | 2.58 |
| H50L21 | 1.232E+5 | 2.671E-4 | 2.17 |
| H51L21 | 1.383E+5 | 2.840E-4 | 2.05 |
| H11L9(sup) | 1.019E+5 | 2.517E-4 | 2.47 |
| H11L9(pur) | 1.013E+5 | 2.490E-4 | 2.46 |
| 6F6 Chimera (pur) | 1.815E+5 | 1.809E-4 | 1.00 |

Biacore Method Used to Determine Binding Kinetics

Anti-human IgG (Biacore BR-1008-39) was coupled to a CM5 biosensor chip by primary amine coupling. The anti-beta amyloid antibodies were captured on this surface. Beta amyloid (1-40) was then passed over at 256, 64, 16, 4 and 1 nM, with a 0 nM (ie buffer alone passed over the captured antibody surface) used for double referencing. Between each amyloid injection the surface was regenerated using 3M $MgCl_2$, this removed the captured antibody but did not significantly affect the ability of the anti-human surface to capture antibodies for subsequent analysis. The data was analysed using the 1:1 model inherent to the T100. The run was carried out at 25° C. and 37° C. using HBS-EP as the running buffer.

From this panel some constructs were also assessed for binding kinetics at physiological temperature. Table 18 shows the binding kinetics of a subset of these constructs at 37° C.

TABLE 18

Selected subset of constructs from Table 17 assessed for binding kinetics at 37° C. (Biacore)

| Construct | ka | kd | KD (nM) |
|---|---|---|---|
| H48L20 | 3.080E+5 | 1.091E-3 | 3.54 |
| H50L20 | 2.704E+5 | 9.466E-4 | 3.50 |
| H51L20 | 2.670E+5 | 1.037E-3 | 3.89 |
| H48L21 | 3.776E+5 | 1.017E-3 | 2.69 |
| H50L21 | 3.503E+5 | 9.463E-4 | 2.70 |
| H51L21 | 3.384E+5 | 9.817E-4 | 2.90 |
| H48L17 | 2.839E+5 | 1.340E-3 | 4.72 |
| H49L17 | 3.439E+5 | 1.448E-3 | 4.21 |
| H11L9 (sup) | 2.970E+5 | 8.592E-4 | 2.89 |
| H11L9 (pu) | 3.261E+5 | 1.015E-3 | 3.11 |

Amino Acid Sequences of V-regions of Acceptor
Frameworks and Humanised Variants
IGVH1-24 heavy chain acceptor framework V region,
amino acid sequence (SEQ ID No: 13)
QVQLVQSGAEVKKPGASVKVSCKVSGYTLTELSMHWVRQAPGKGLEWMGG

FDPEDGETIYAQKFQGRVTMTEDTSTDTAYMELSSLRSEDTAVYYCAT

IGVH1-24 heavy chain acceptor framework V region
DNA (SEQ ID No: 14)
CAGGTCCAGCTGGTACAGTCTGGGGCTGAGGTGAAGAAGCCTGGGGCCTC

AGTGAAGGTCTCCTGCAAGGTTTCCGGATACACCCTCACTGAATTATCCA

TGCACTGGGTGCGACAGGCTCCTGGAAAAGGGCTTGAGTGGATGGGAGGT

-continued
TTTGATCCTGAAGATGGTGAAACAATCTACGCACAGAAGTTCCAGGGCAG

AGTCACCATGACCGAGGACACATCTACAGACACAGCCTACATGGAGCTGA

GCAGCCTGAGATCTGAGGACACGGCCGTGTATTACTGTGCAACA

IGKV2-28 light chain acceptor framework V region
amino acid sequence (SEQ ID No: 16)
DIVMTQSPLSLPVTPGEPASISCRSSQSLLHSNGYNYLDWYLQKPGQSPQ

LLIYLGSNRASGVPDRFSGSGSGTDFTLKISRVEAEDVGVYYCMQALQTP

IGKV2-28 light chain acceptor framework V region
DNA (SEQ ID No: 17)
GATATTGTGATGACTCAGTCTCCACTCTCCCTGCCCGTCACCCCTGGAGA

GCCGGCCTCCATCTCCTGCAGGTCTAGTCAGAGCCTCCTGCATAGTAATG

GATACAACTATTTGGATTGGTACCTGCAGAAGCCAGGGCAGTCTCCACAG

CTCCTGATCTATTTGGGTTCTAATCGGGCCTCCGGGGTCCCTGACAGGTT

CAGTGGCAGTGGATCAGGCACAGATTTTACACTGAAAATCAGCAGAGTGG

AGGCTGAGGATGTTGGGGTTTATTACTGCATGCAAGCTCTACAAACTCCT

Humanised heavy chain V region variant H11 DNA
Sequence (SEQ ID No: 23)
CAGGTCCAGCTGGTACAGTCTGGGGCTGAGGTGAAGGAGCCTGGGGCCTC

AGTGAAGGTCTCCTGCAAGGGTTCCGGATTCAACATTAAGGTCTACTATG

TGCACTGGCTGCGACAGCTTCCTGGAAAAGGGCTTGAGTGGATCGGAAGG

ATTGATCCTGAAAATGGTGAAACTATATATACCCCGAAATTCCAGGACAA

GGCCACCTTGACCGTAGACACATCTACAGACACAGCCTACATGGAGCTGA

GCAGCCTGAGATCTGAGGACACGGCCGTGTATTACTGTGTTAGTTCGGGC

TACTGGGGCCAGGGCACACTAGTGACCGTGTCCAGC

Humanised heavy chain V region variant H11 amino
acid sequence (SEQ ID No: 24)
QVQLVQSGAEVKEPGASVKVSCKGSGFNIKVYYVHWLRQLPGKGLEWIGR

IDPENGETIYTPKFQDKATLTVDTSTDTAYMELSSLRSEDTAVYYCVSSG

YWGQGTLVTVSS

Humanised light chain V region variant L9 DNA
Sequence (SEQ ID No: 25)
GATATTGTGATGACTCAGTCTCCACTCTCCAATCCCGTCACCCCTGGAGA

GCCGGCCTCCATCTCCTGCAGGTCTAGCAAGAGTCTCCTACATAGGAATG

GCATCACCTATTTGTATTGGTACCTGCAGAAGCCAGGGCAGTCTCCACAG

CTCCTGATCTATCAGATGTCCAACCTTGCCTCAGGGGTCCCTGACAGGTT

CAGTAGCAGTGGATCAGGCACAGATTTTACACTGAAAATCAGCAGAGTGG

AGGCTGAGGATGTTGGGGTTTATTACTGCGCTCAAAATCTAGAACTTTGG

ACGTTCGGCCAAGGGACCAAGGTGGAAATCAAA

Humanised light chain V region variant L9 amino
acid sequence (SEQ ID No: 26)
DIVMTQSPLSNPVTPGEPASISCRSSKSLLHRNGITYLYWYLQKPGQSPQ

LLIYQMSNLASGVPDRFSSSGSGTDFTLKISRVEAEDVGVYYCAQNLELW

TFGQGTKVEIK

Mature H11 heavy chain amino acid sequence
(SEQ ID No: 27)
QVQLVQSGAEVKEPGASVKVSCKGSGFNIKVYYVHWLRQLPGKGLEWIGR

IDPENGETIYTPKFQDKATLTVDTSTDTAYMELSSLRSEDTAVYYCVSSG

YWGQGTLVTVSSASTKGPSVFPLAPSSKSTSGGTAALGCLVKDYFPEPVT

VSWNSGALTSGVHTFPAVLQSSGLYSLSSVVTVPSSSLGTQTYICNVNHK

PSNTKVDKKVEPKSCDKTHTCPPCPAPELAGAPSVFLFPPKPKDTLMISR

TPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSR

DELTKNQVSLTCLVKGFYPSDIAVEWESNGQPENNYKTTPPVLDSDGSFF

LYSKLTVDKSRWQQGNVFSCSVMHEALHNHYTQKSLSLSPGK

Mature L9 light chain amino acid sequence
(SEQ ID No: 28)
DIVMTQSPLSNPVTPGEPASISCRSSKSLLHRNGITYLYWYLQKPGQSPQ

LLIYQMSNLASGVPDRFSSSGSGTDFTLKISRVEAEDVGVYYCAQNLELW

TFGQGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC

Optimised H11 heavy chain DNA (SEQ ID No: 29)
CAGGTGCAGCTCGTGCAGAGCGGCGCCGAGGTGAAAGAACCCGGCGCCAG

CGTGAAGGTGAGCTGCAAGGGCAGCGGCTTCAACATCAAAGTGTACTACG

TGCACTGGCTGAGGCAGCTGCCCGGAAAGGGCCTGGAGTGGATTGGCAGG

ATCGACCCCGAGAACGGCGAGACCATCTACACCCCCAAGTTCCAGGACAA

GGCCACCCTGACCGTGGACACCAGCACCGACACCGCCTACATGGAACTGA

GCAGCCTGAGGTCCGAGGATACCGCCGTCTACTACTGCGTGAGCAGCGGG

TATTGGGGCCAGGGCACACTAGTGACCGTGAGCAGCGCCAGCACCAAGGG

CCCCAGCGTGTTCCCCCTGGCCCCCAGCAGCAAGAGCACCAGCGGCGGCA

CAGCCGCCCTGGGCTGCCTGGTGAAGGACTACTTCCCCGAGCCCGTGACC

GTGTCCTGGAACAGCGGAGCCCTGACAAGCGGGGTGCACACCTTCCCCGC

CGTGCTGCAGAGCAGCGGCCTGTACAGCCTGAGCAGCGTGGTGACAGTGC

CCAGCAGCAGCCTGGGCACCCAGACCTACATCTGCAACGTGAACCACAAG

CCCAGCAACACCAAGGTGGACAAGAAGGTGGAGCCCAAGAGCTGCGACAA

GACCCACACCTGCCCCCCCTGCCCTGCCCCTGAACTGGCCGGAGCCCCCT

CCGTGTTCCTGTTCCCCCCCAAGCCCAAGGACACCCTGATGATCAGCCGG

ACCCCCGAGGTGACCTGCGTGGTGGTGGACGTGAGCCACGAGGACCCTGA

GGTGAAGTTCAATTGGTACGTGGACGGCGTGGAGGTGCACAACGCCAAGA

CCAAGCCCCGGGAGGAACAGTACAACAGCACCTACCGGGTGGTGTCCGTG

CTGACCGTGCTGCACCAGGACTGGCTGAACGGCAAAGAATACAAGTGCAA

GGTGTCCAACAAGGCCCTGCCTGCCCCCATCGAGAAAACCATCAGCAAGG

CCAAGGGCCAGCCCAGGGAACCCCAGGTGTACACCCTGCCCCCCTCCCGG

GACGAGCTGACCAAGAACCAGGTGTCCCTGACCTGTCTGGTGAAGGGCTT

CTACCCCAGCGACATCGCCGTGGAGTGGGAGAGCAACGGCCAGCCCGAGA

ACAACTACAAGACCACCCCCCCTGTGCTGGACAGCGACGGCAGCTTCTTC

CTGTACAGCAAGCTGACCGTGGACAAGAGCCGGTGGCAGCAGGGCAACGT

GTTCAGCTGCAGCGTGATGCACGAGGCCCTGCACAACCACTACACCCAGA

AGAGCCTGAGCCTGTCCCCCGGCAAG

Optimised L9 light chain DNA (SEQ ID No: 30)
GACATCGTGATGACCCAGAGCCCACTGAGCAATCCCGTGACTCCCGGCGA

GCCCGCCTCAATCAGCTGCAGGAGCAGCAAGAGCCTGCTGCACAGGAACG

GCATCACCTACCTGTACTGGTATCTGCAGAAGCCCGGCCAGAGCCCCCAG

CTGCTGATCTACCAGATGTCCAACCTGGCCAGCGGCGTGCCCGACCGGTT

CTCTAGCAGCGGAAGCGGCACCGACTTCACCCTGAAGATCAGCAGGGTGG

AAGCCGAGGACGTGGGCGTGTACTACTGCGCCCAGAACCTGGAGCTCTGG

ACCTTCGGCCAGGGCACCAAGGTGGAGATCAAACGTACGGTGGCCGCCCC

CAGCGTGTTCATCTTCCCCCCCAGCGATGAGCAGCTGAAGAGCGGCACCG

CCAGCGTGGTGTGTCTGCTGAACAACTTCTACCCCCGGGAGGCCAAGGTG

CAGTGGAAGGTGGACAATGCCCTGCAGAGCGGCAACAGCCAGGAGAGCGT

GACCGAGCAGGACAGCAAGGACTCCACCTACAGCCTGAGCAGCACCCTGA

CCCTGAGCAAGGCCGACTACGAGAAGCACAAGGTGTACGCCTGTGAGGTG

ACCCACCAGGGCCTGTCCAGCCCCGTGACCAAGAGCTTCAACCGGGGCGA

GTGC

H48 heavy chain V region variant amino acid
sequence (SEQ ID No: 59)
QVQLVQSGAEVKEPGASVKVSCKGSGFNIHVYYVHWLRQLPEKGLEWIGR

IDPENGETIYTPKFQDKATLTVDTSTDTAYMELSSLRSEDTAVYYCVSSG

YWGQGTLVTVSS

H48 heavy chain V region variant DNA sequence
(SEQ ID No: 60)
CAGGTGCAGCTCGTGCAGAGCGGCGCCGAGGTGAAAGAACCCGGCGCCAG

CGTGAAGGTGAGCTGCAAGGGCAGCGGCTTCAACATCCACGTGTACTACG

TGCACTGGCTGAGGCAGCTGCCCGAGAAGGGCCTGGAGTGGATTGGCAGG

ATCGACCCCGAGAACGGCGAGACCATCTACACCCCCAAGTTCCAGGACAA

GGCCACCCTGACCGTGGACACCAGCACCGACACCGCCTACATGGAACTGA

GCAGCCTGAGGTCCGAGGATACCGCCGTCTACTACTGCGTGAGCAGCGGG

TATTGGGGCCAGGGCACACTAGTGACCGTGTCCAGC

H49 heavy chain V region variant amino acid
sequence (SEQ ID No: 61)
QVQLVQSGAEVKEPGASVKVSCKGSGFNIKTYYVHWLRQLPEKGLEWIGR

IDPENGETIYTPKFQDKATLTVDTSTDTAYMELSSLRSEDTAVYYCVSSG

YWGQGTLVTVSS

H49 heavy chain V region variant DNA sequence
(SEQ ID No: 62)
CAGGTGCAGCTCGTGCAGAGCGGCGCCGAGGTGAAAGAACCCGGCGCCAG

CGTGAAGGTGAGCTGCAAGGGCAGCGGCTTCAACATCAAAACCTACTACG

TGCACTGGCTGAGGCAGCTGCCCGAGAAGGGCCTGGAGTGGATTGGCAGG

ATCGACCCCGAGAACGGCGAGACCATCTACACCCCCAAGTTCCAGGACAA

GGCCACCCTGACCGTGGACACCAGCACCGACACCGCCTACATGGAACTGA

GCAGCCTGAGGTCCGAGGATACCGCCGTCTACTACTGCGTGAGCAGCGGG

TATTGGGGCCAGGGCACACTAGTGACCGTGTCCAGC

H50 heavy chain V region variant amino acid
sequence (SEQ ID No: 63)
QVQLVQSGAEVKEPGASVKVSCTGSGFNIHVYYVHWLRQLPEKGLEWIGR

IDPENGETIYTPKFQDKATLTVDTSTDTAYMELSSLRSEDTAVYYCVSSG

YWGQGTLVTVSS

H50 heavy chain V region variant DNA sequence
(SEQ ID No: 64)
CAGGTGCAGCTCGTGCAGAGCGGCGCCGAGGTGAAAGAACCCGGCGCCAG

CGTGAAGGTGAGCTGCACCGGCAGCGGCTTCAACATCCACGTGTACTACG

TGCACTGGCTGAGGCAGCTGCCCGAGAAGGGCCTGGAGTGGATTGGCAGG

ATCGACCCCGAGAACGGCGAGACCATCTACACCCCCAAGTTCCAGGACAA

GGCCACCCTGACCGTGGACACCAGCACCGACACCGCCTACATGGAACTGA

GCAGCCTGAGGTCCGAGGATACCGCCGTCTACTACTGCGTGAGCAGCGGG

TATTGGGGCCAGGGCACACTAGTGACCGTGTCCAGC

H51 heavy chain V region variant amino acid
sequence (SEQ ID No: 65)
QVQLVQSGAEVKEPGASVKVSCKGSGFNIHTYYVHWLRQLPEKGLEWIGR

IDPENGETIYTPKFQDKATLTVDTSTDTAYMELSSLRSEDTAVYYCVSSG

YWGQGTLVTVSS

H51 heavy chain V region variant DNA sequence
(SEQ ID No: 66)
CAGGTGCAGCTCGTGCAGAGCGGCGCCGAGGTGAAAGAACCCGGCGCCAG

CGTGAAGGTGAGCTGCAAGGGCAGCGGCTTCAACATCCACACCTACTACG

TGCACTGGCTGAGGCAGCTGCCCGAGAAGGGCCTGGAGTGGATTGGCAGG

ATCGACCCCGAGAACGGCGAGACCATCTACACCCCCAAGTTCCAGGACAA

GGCCACCCTGACCGTGGACACCAGCACCGACACCGCCTACATGGAACTGA

GCAGCCTGAGGTCCGAGGATACCGCCGTCTACTACTGCGTGAGCAGCGGG

TATTGGGGCCAGGGCACACTAGTGACCGTGTCCAGC

L19 light chain V region variant amino acid
sequence (SEQ ID No: 67)
DIVMTQSPLSNPVTPGEPASISCRSSKSLLHRNGKTYLYWYLQKPGQSPQ

LLIYQMDHLASGVPDRFSSSGSGTDFTLKISRVEAEDVGVYYCAQNLELW

TFGQGTKVEIK

L19 light chain V region variant DNA sequence
(SEQ ID No: 68)
GACATCGTGATGACCCAGAGCCCACTGAGCAATCCCGTGACTCCCGGCGA

GCCCGCCTCAATCAGCTGCAGGAGCAGCAAGAGCCTGCTGCACAGGAACG

GCAAGACCTACCTGTACTGGTATCTGCAGAAGCCCGGCCAGAGCCCCCAG

CTGCTGATCTACCAGATGGACCACCTGGCCAGCGGCGTGCCCGACCGGTT

CTCTAGCAGCGGAAGCGGCACCGACTTCACCCTGAAGATCAGCAGGGTGG

AAGCCGAGGACGTGGGCGTGTACTACTGCGCCCAGAACCTGGAGCTCTGG

ACCTTCGGCCAGGGCACCAAGGTGGAGATCAAA

L20 light chain V region variant amino acid sequence (SEQ ID No: 69)
DIVMTQSPLSNPVTPGEPASISCRSSKSLLHRNGITYLYWYLQKPGQSPQLLIYQMDHLASGVPDRFSSSGSGTDFTLKISRVEAEDVGVYYCAQNLELWTFGQGTKVEIK L20 light chain V region variant DNA sequence (SEQ ID No: 70)
GACATCGTGATGACCCAGAGCCCACTGAGCAATCCCGTGACTCCCGGCGAGCCCGCCTCAATCAGCTGCAGGAGCAGCAAGAGCCTGCTGCACAGGAACGGCATCACCTACCTGTACTGGTATCTGCAGAAGCCCGGCCAGAGCCCCCAGCTGCTGATCTACCAGATGGACCACCTGGCCAGCGGCGTGCCCGACCGGTTCTCTAGCAGCGGAAGCGGCACCGACTTCACCCTGAAGATCAGCAGGGTGGAAGCCGAGGACGTGGGCGTGTACTACTGCGCCCAGAACCTGGAGCTCTGGACCTTCGGCCAGGGCACCAAGGTGGAGATCAAA L21 light chain V region variant amino acid sequence (SEQ ID No: 71)
DIVMTQSPLSNPVTPGEPASISCRSSKSLLHRNGKTYLYWYLQKPGQSPQLLIYQMDNLASGVPDRFSSSGSGTDFTLKISRVEAEDVGVYYCAQNLELWTFGQGTKVEIK L21 light chain V region variant DNA sequence (SEQ ID No: 72)
GACATCGTGATGACCCAGAGCCCACTGAGCAATCCCGTGACTCCCGGCGAGCCCGCCTCAATCAGCTGCAGGAGCAGCAAGAGCCTGCTGCACAGGAACGGCAAGACCTACCTGTACTGGTATCTGCAGAAGCCCGGCCAGAGCCCCCAGCTGCTGATCTACCAGATGGACAACCTGGCCAGCGGCGTGCCCGACCGGTTCTCTAGCAGCGGAAGCGGCACCGACTTCACCCTGAAGATCAGCAGGGTGGAAGCCGAGGACGTGGGCGTGTACTACTGCGCCCAGAACCTGGAGCTCTGGACCTTCGGCCAGGGCACCAAGGTGGAGATCAAA

---

The invention claimed is:

1. A therapeutic humanized antibody which is an antibody or antigen binding fragment thereof which binds an epitope of β-amyloid peptide that is within the region of residues 28-35 of β-amyloid and which comprises the following CDRs:
   CDRH1: VYYVH (SEQ ID No:1)
   CDRH2: RIDPENGETIYTPKFQD (SEQ ID No:2)
   CDRH3: SGY (SEQ ID No:3)
   CDRL1: RSSKSLLHRNGITYLY (SEQ ID No:4)
   CDRL2: QMSNLAS (SEQ ID No:5)
   CDRL3: AQNLELWT (SEQ ID No:6).

2. A therapeutic antibody according to claim 1 in which the human acceptor heavy chain framework is derived from IGHV1-24 and the JH4 minigene and the human acceptor light chain framework is derived from IGKV2-28 and JK-1 minigene optionally containing one or more substitutions of amino acid residues based on the corresponding residues found in the donor $V_H$ domain having the sequence: SEQ ID No:19 and $V_L$ domain having the sequence: SEQ ID No:21 that maintain all or substantially all of the binding affinity of the donor antibody for β-amyloid peptide.

3. A therapeutic antibody according to claim 2 in which the human acceptor heavy chain framework has one or more amino acid residue substitutions selected from the following residues (or conservative substitutions thereof):

| Kabat Numbering of residue | Human Framework Residue (donor IGHV1-24) | Corresponding residue in murine 6F6 |
|---|---|---|
| 1 | Q | E |
| 5 | V | Q |
| 13 | K | E |
| 24 | V | G |
| 27 | Y | F |
| 28 | T | N |
| 29 | L | I |
| 30 | T | K |
| 37 | V | L |
| 40 | A | L |
| 41 | P | T |
| 48 | M | I |
| 66 | R | K |
| 67 | V | A |
| 69 | M | L |
| 71 | E | V |
| 75 | T | S |
| 76 | D | N |
| 93 | A | V |
| 94 | T | S |

4. A therapeutic antibody according to claim 3 in which the human acceptor heavy chain framework comprises the following residues (or a conservative substitute thereof):

| Kabat Numbering of residue | Human Framework Residue (donor IGHV1-24) | Residue substitution |
|---|---|---|
| 13 | K | E |
| 24 | V | G |
| 27 | Y | F |
| 28 | T | N |
| 29 | L | I |
| 30 | T | K |
| 37 | V | L |
| 40 | A | L |
| 48 | M | I |
| 66 | R | K |
| 67 | V | A |
| 69 | M | L |
| 71 | E | V |
| 93 | A | V |
| 94 | T | S |

5. A therapeutic antibody according to any of claims 2 to 4 in which the human acceptor light chain framework has one or more amino acid residue substitutions selected from the following residues (or conservative substitutions thereof):

| Kabat Numbering of residue | Human Framework Residue (donor IGHV1-24) | Residue substitution |
|---|---|---|
| 8 | P | A |
| 11 | L | N |
| 43 | S | P |
| 63 | S | T |
| 64 | G | S |
| 100 | Q (JK-1) | G |
| 104 | V (JK-1) | L |

6. A therapeutic antibody according to claim 5 in which the human acceptor light chain framework comprises the following residues (or a conservative substitute thereof):

| Kabat Numbering of residue | Human Framework Residue (donor IGHV1-24) | Residue substitution |
|---|---|---|
| 11 | L | N |
| 64 | G | S |

7. A therapeutic antibody which binds to β-amyloid peptide comprising a $V_H$ domain having the sequence set forth in SEQ ID No:65 and a $V_L$ domain having the sequence set forth in SEQ ID No:71.

* * * * *

SEQUENCE LISTING

```
<160> NUMBER OF SEQ ID NOS: 73

<210> SEQ ID NO 1
<211> LENGTH: 5
<212> TYPE: PRT
<213> ORGANISM: Artificial Sequence
<220> FEATURE:
<223> OTHER INFORMATION: CDRH1 aa

<400> SEQUENCE: 1

Val Tyr Tyr Val His
 1               5

<210> SEQ ID NO 2
<211> LENGTH: 17
<212> TYPE: PRT
<213> ORGANISM: Artificial Sequence
<220> FEATURE:
<223> OTHER INFORMATION: CDRH2 aa

<400> SEQUENCE: 2

Arg Ile Asp Pro Glu Asn Gly Glu Thr Ile Tyr Thr Pro Lys Phe Gln
 1               5                  10                  15

Asp

<210> SEQ ID NO 3
<211> LENGTH: 3
<212> TYPE: PRT
<213> ORGANISM: Artificial Sequence
<220> FEATURE:
<223> OTHER INFORMATION: CDRH3 aa

<400> SEQUENCE: 3

Ser Gly Tyr
 1

<210> SEQ ID NO 4
<211> LENGTH: 16
<212> TYPE: PRT
<213> ORGANISM: Artificial Sequence
<220> FEATURE:
<223> OTHER INFORMATION: CDRL1 aa
```

```
<400> SEQUENCE: 4

Arg Ser Ser Lys Ser Leu Leu His Arg Asn Gly Ile Thr Tyr Leu Tyr
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: CDRL2 aa

<400> SEQUENCE: 5

Gln Met Ser Asn Leu Ala Ser
1               5

<210> SEQ ID NO 6
<211> LENGTH: 8
<212> TYPE: PRT
<213> ORGANISM: Artificial Sequence
<220> FEATURE:
<223> OTHER INFORMATION: CDRL3 aa

<400> SEQUENCE: 6

Ala Gln Asn Leu Glu Leu Trp Thr
1               5

<210> SEQ ID NO 7
<211> LENGTH: 16
<212> TYPE: PRT
<213> ORGANISM: Artificial Sequence
<220> FEATURE:
<223> OTHER INFORMATION: peptide conjugate containing beta amyloid
      residues 27-38 used for immunisation and screening

<400> SEQUENCE: 7

Cys Gly Gly Gly Asn Lys Gly Ala Ile Ile Gly Leu Met Val Gly Gly
1               5                   10                  15

<210> SEQ ID NO 8
<211> LENGTH: 11
<212> TYPE: PRT
<213> ORGANISM: Artificial Sequence
<220> FEATURE:
<223> OTHER INFORMATION: Assay peptide containing beta amyloid residues
      24-34

<400> SEQUENCE: 8

Val Gly Ser Asn Lys Gly Ala Ile Ile Gly Leu
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Epitope mapping peptide  containing beta
      amyloid residues 28-35

<400> SEQUENCE: 9

Lys Gly Ala Ile Ile Gly Leu Met
1               5

<210> SEQ ID NO 10
<211> LENGTH: 15
<212> TYPE: PRT
<213> ORGANISM: Artificial Sequence
```

```
<220> FEATURE:
<223> OTHER INFORMATION: Epitope mapping peptide containing beta
      amyloid residues 24-35

<400> SEQUENCE: 10

Val Gly Ser Asn Lys Gly Ala Ile Ile Gly Leu Met Gly Ser Gly
 1               5                  10                  15

<210> SEQ ID NO 11
<211> LENGTH: 15
<212> TYPE: PRT
<213> ORGANISM: Artificial Sequence
<220> FEATURE:
<223> OTHER INFORMATION: Epitope mapping peptide containing beta
      amyloid residues 28-39

<400> SEQUENCE: 11

Lys Gly Ala Ile Ile Gly Leu Met Val Gly Gly Val Gly Ser Gly
 1               5                  10                  15

<210> SEQ ID NO 12
<211> LENGTH: 15
<212> TYPE: PRT
<213> ORGANISM: Artificial Sequence
<220> FEATURE:
<223> OTHER INFORMATION: Epitope mapping peptide containing beta
      amyloid residues 31-42

<400> SEQUENCE: 12

Ile Ile Gly Leu Met Val Gly Gly Val Val Ile Ala Gly Ser Gly
 1               5                  10                  15

<210> SEQ ID NO 13
<211> LENGTH: 98
<212> TYPE: PRT
<213> ORGANISM: Homo Sapiens

<400> SEQUENCE: 13

Gln Val Gln Leu Val Gln Ser Gly Ala Glu Val Lys Lys Pro Gly Ala
 1               5                  10                  15

Ser Val Lys Val Ser Cys Lys Val Ser Gly Tyr Thr Leu Thr Glu Leu
                20                  25                  30

Ser Met His Trp Val Arg Gln Ala Pro Gly Lys Gly Leu Glu Trp Met
            35                  40                  45

Gly Gly Phe Asp Pro Glu Asp Gly Glu Thr Ile Tyr Ala Gln Lys Phe
        50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr

<210> SEQ ID NO 14
<211> LENGTH: 294
<212> TYPE: DNA
<213> ORGANISM: Homo sapiens

<400> SEQUENCE: 14
caggtccagc tggtacagtc tggggctgag gtgaagaagc ctggggcctc agtgaaggtc      60
tcctgcaagg tttccggata caccctcact gaattatcca tgcactgggt gcgacaggct    120
cctggaaaag ggcttgagtg gatgggaggt tttgatcctg aagatggtga aacaatctac    180
```

```
gcacagaagt tccagggcag agtcaccatg accgaggaca catctacaga cacagcctac    240
atggagctga gcagcctgag atctgaggac acggccgtgt attactgtgc aaca          294
```

<210> SEQ ID NO 15
<211> LENGTH: 15
<212> TYPE: PRT
<213> ORGANISM: Homo sapiens

<400> SEQUENCE: 15

```
Tyr Phe Asp Tyr Trp Gly Gln Gly Thr Leu Val Thr Val Ser Ser
 1               5                  10                  15
```

<210> SEQ ID NO 16
<211> LENGTH: 100
<212> TYPE: PRT
<213> ORGANISM: Homo sapiens

<400> SEQUENCE: 16

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
 65                 70                  75                  80

Ser Arg Val Glu Ala Glu Asp Val Gly Val Tyr Tyr Cys Met Gln Ala
                85                  90                  95

Leu Gln Thr Pro
            100
```

<210> SEQ ID NO 17
<211> LENGTH: 300
<212> TYPE: DNA
<213> ORGANISM: Homo sapiens

<400> SEQUENCE: 17

```
gatattgtga tgactcagtc tccactctcc ctgcccgtca cccctggaga gccggcctcc    60
atctcctgca ggtctagtca gagcctcctg catagtaatg gatacaacta tttggattgg   120
tacctgcaga agccagggca gtctccacag ctcctgatct atttgggttc taatcgggcc   180
tccggggtcc ctgacaggtt cagtggcagt ggatcaggca cagattttac actgaaaatc   240
agcagagtgg aggctgagga tgttggggtt tattactgca tgcaagctct acaaactcct   300
```

<210> SEQ ID NO 18
<211> LENGTH: 12
<212> TYPE: PRT
<213> ORGANISM: Homo sapiens

<400> SEQUENCE: 18

```
Trp Thr Phe Gly Gln Gly Thr Lys Val Glu Ile Lys
 1               5                  10
```

<210> SEQ ID NO 19
<211> LENGTH: 112
<212> TYPE: PRT
<213> ORGANISM: Mus muscularis -continued

<400> SEQUENCE: 19

| Glu | Val | Gln | Leu | Gln | Gln | Ser | Gly | Ala | Glu | Leu | Val | Glu | Pro | Gly | Ala |
| 1 | | | | 5 | | | | | 10 | | | | | 15 | |

| Ser | Val | Lys | Leu | Ser | Cys | Thr | Gly | Ser | Gly | Phe | Asn | Ile | Lys | Val | Tyr |
| | | | 20 | | | | | 25 | | | | | 30 | | |

| Tyr | Val | His | Trp | Leu | Lys | Gln | Leu | Thr | Glu | Gln | Gly | Leu | Glu | Trp | Ile |
| | | 35 | | | | | 40 | | | | | 45 | | | |

| Gly | Arg | Ile | Asp | Pro | Glu | Asn | Gly | Glu | Thr | Ile | Tyr | Thr | Pro | Lys | Phe |
| | 50 | | | | | 55 | | | | | 60 | | | | |

| Gln | Asp | Lys | Ala | Thr | Leu | Thr | Val | Asp | Thr | Ser | Ser | Asn | Thr | Ala | Tyr |
| 65 | | | | | 70 | | | | | 75 | | | | | 80 |

| Leu | Gln | Leu | Ser | Ser | Leu | Thr | Ser | Glu | Asp | Ala | Ala | Val | Tyr | Tyr | Cys |
| | | | | 85 | | | | | 90 | | | | | 95 | |

| Val | Ser | Ser | Gly | Tyr | Trp | Gly | Gln | Gly | Thr | Thr | Leu | Thr | Val | Ser | Ser |
| | | | 100 | | | | | 105 | | | | | 110 | | |

<210> SEQ ID NO 20
<211> LENGTH: 336
<212> TYPE: DNA
<213> ORGANISM: Mus muscularis

<400> SEQUENCE: 20

```
gaggttcagc tgcagcagtc tggggcagag cttgtggagc caggggcctc agtcaagttg      60
tcctgcacag gttctggctt caacattaag gtctactatg tgcactggct gaagcagttg     120
actgagcagg gcctggaatg gattggaagg attgatcctg aaaatggtga actatatat     180
accccgaaat tccaggacaa ggccactttg acagtagaca catcatccaa cacagcctac     240
ctgcagctca gcagcctgac atctgaggac gctgccgtgt actattgtgt tagttcgggc     300
tactgggggcc aaggcaccac tctcacagtc tcctca                              336
```

<210> SEQ ID NO 21
<211> LENGTH: 111
<212> TYPE: PRT
<213> ORGANISM: Mus muscularis

<400> SEQUENCE: 21

| Asp | Ile | Val | Met | Thr | Gln | Ser | Ala | Phe | Ser | Asn | Pro | Val | Thr | Leu | Gly |
| 1 | | | | 5 | | | | | 10 | | | | | 15 | |

| Thr | Ser | Ala | Ser | Ile | Ser | Cys | Arg | Ser | Ser | Lys | Ser | Leu | Leu | His | Arg |
| | | | 20 | | | | | 25 | | | | | 30 | | |

| Asn | Gly | Ile | Thr | Tyr | Leu | Tyr | Trp | Tyr | Leu | Gln | Lys | Pro | Gly | Gln | Pro |
| | | 35 | | | | | 40 | | | | | 45 | | | |

| Pro | Gln | Leu | Leu | Ile | Tyr | Gln | Met | Ser | Asn | Leu | Ala | Ser | Gly | Val | Pro |
| | 50 | | | | | 55 | | | | | 60 | | | | |

| Asp | Arg | Phe | Thr | Ser | Ser | Gly | Ser | Gly | Thr | Asp | Phe | Thr | Leu | Lys | Ile |
| 65 | | | | | 70 | | | | | 75 | | | | | 80 |

| Ser | Arg | Val | Glu | Ala | Glu | Asp | Val | Gly | Val | Tyr | Tyr | Cys | Ala | Gln | Asn |
| | | | | 85 | | | | | 90 | | | | | 95 | |

| Leu | Glu | Leu | Trp | Thr | Phe | Gly | Gly | Gly | Thr | Lys | Leu | Glu | Ile | Lys | |
| | | | 100 | | | | | 105 | | | | | 110 | | |

<210> SEQ ID NO 22
<211> LENGTH: 333
<212> TYPE: DNA
<213> ORGANISM: Mus muscularis

<400> SEQUENCE: 22

```
gatattgtga tgacgcagtc tgcattctcc aatccagtca ctcttggaac atcagcttcc    60
atctcctgca ggtctagcaa gagtctccta cataggaatg catcaccta tttgtattgg    120 tatctgcaga agccaggcca gcctcctcaa ctcctgattt atcagatgtc aaccttgcc    180 tcaggagtcc cagacaggtt cactagcagt gggtcaggaa ctgatttcac tctgaaaatc    240
agcagagtgg aggctgagga tgtgggtgtt tattactgtg ctcaaaatct agaactttgg    300
acgttcggtg aggcaccaa gctggaaatc aaa                                 333
```

<210> SEQ ID NO 23
<211> LENGTH: 336
<212> TYPE: DNA
<213> ORGANISM: Artificial Sequence
<220> FEATURE:
<223> OTHER INFORMATION: H11 VH DNA

<400> SEQUENCE: 23

```
caggtccagc tggtacagtc tggggctgag gtgaaggagc ctggggcctc agtgaaggtc    60
tcctgcaagg gttccggatt caacattaag gtctactatg tgcactggct gcgacagctt    120
cctggaaaag gcttgagtg gatcggaagg attgatcctg aaaatggtga aactatatat    180
accccgaaat tccaggacaa ggccaccttg accgtagaca tctacagaca cagcctac     240 atggagctga gcagcctgag atctgaggac acggccgtgt attactgtgt tagttcgggc    300
tactggggcc agggcacact agtgaccgtg tccagc                             336
```

<210> SEQ ID NO 24
<211> LENGTH: 112
<212> TYPE: PRT
<213> ORGANISM: Artificial Sequence
<220> FEATURE:
<223> OTHER INFORMATION: H11 VH aa

<400> SEQUENCE: 24

Gln Val Gln Leu Val Gln Ser Gly Ala Glu Val Lys Glu Pro Gly Ala
 1               5                  10                  15

Ser Val Lys Val Ser Cys Lys Gly Ser Gly Phe Asn Ile Lys Val Tyr
            20                  25                  30

Tyr Val His Trp Leu Arg Gln Leu Pro Gly Lys Gly Leu Glu Trp Ile
        35                  40                  45

Gly Arg Ile Asp Pro Glu Asn Gly Glu Thr Ile Tyr Thr Pro Lys Phe
    50                  55                  60

Gln Asp Lys Ala Thr Leu Thr Val Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Val Ser Ser Gly Tyr Trp Gly Gln Gly Thr Leu Val Thr Val Ser Ser
            100                 105                 110

<210> SEQ ID NO 25
<211> LENGTH: 333
<212> TYPE: DNA
<213> ORGANISM: Artificial Sequence
<220> FEATURE:
<223> OTHER INFORMATION: L9 VL DNA

<400> SEQUENCE: 25

```
gatattgtga tgactcagtc tccactctcc aatcccgtca cccctggaga gccggcctcc    60
atctcctgca ggtctagcaa gagtctccta cataggaatg catcaccta tttgtattgg    120
```

```
tacctgcaga agccagggca gtctccacag ctcctgatct atcagatgtc caaccttgcc    180 tcagggtcc ctgacaggtt cagtagcagt ggatcaggca cagattttac actgaaaatc    240
agcagagtgg aggctgagga tgttggggtt tattactgcg ctcaaaatct agaactttgg   300
acgttcggcc aagggaccaa ggtggaaatc aaa                                333
```

<210> SEQ ID NO 26
<211> LENGTH: 111
<212> TYPE: PRT
<213> ORGANISM: Artificial Sequence
<220> FEATURE:
<223> OTHER INFORMATION: L9 VL aa

<400> SEQUENCE: 26

```
Asp Ile Val Met Thr Gln Ser Pro Leu Ser Asn Pro Val Thr Pro Gly
1               5                   10                  15

Glu Pro Ala Ser Ile Ser Cys Arg Ser Ser Lys Ser Leu Leu His Arg
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Trp Thr Phe Gly Gln Gly Thr Lys Val Glu Ile Lys
            100                 105                 110
```

<210> SEQ ID NO 27
<211> LENGTH: 442
<212> TYPE: PRT
<213> ORGANISM: Artificial Sequence
<220> FEATURE:
<223> OTHER INFORMATION: H11 heavy chain aa

<400> SEQUENCE: 27

```
Gln Val Gln Leu Val Gln Ser Gly Ala Glu Val Lys Glu Pro Gly Ala
1               5                   10                  15

Ser Val Lys Val Ser Cys Lys Gly Ser Gly Phe Asn Ile Lys Val Tyr
            20                  25                  30

Tyr Val His Trp Leu Arg Gln Leu Pro Gly Lys Gly Leu Glu Trp Ile
        35                  40                  45

Gly Arg Ile Asp Pro Glu Asn Gly Glu Thr Ile Tyr Thr Pro Lys Phe
    50                  55                  60

Gln Asp Lys Ala Thr Leu Thr Val Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Val Ser Ser Gly Tyr Trp Gly Gln Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160
```

Gly Val His Thr Phe Pro Ala Val Leu Gln Ser Ser Gly Leu Tyr Ser
                165                 170                 175

Leu Ser Ser Val Val Thr Val Pro Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Ala Gly Ala Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 28
<211> LENGTH: 218
<212> TYPE: PRT
<213> ORGANISM: Artificial Sequence
<220> FEATURE:
<223> OTHER INFORMATION: L9 heavy chain aa

<400> SEQUENCE: 28

Asp Ile Val Met Thr Gln Ser Pro Leu Ser Asn Pro Val Thr Pro Gly
1               5                   10                  15

Glu Pro Ala Ser Ile Ser Cys Arg Ser Ser Lys Ser Leu Leu His Arg
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Lys Ile
65                  70                  75                  80

```
Ser Arg Val Glu Ala Glu Asp Val Gly Val Tyr Tyr Cys Ala Gln Asn
                85                  90                  95

Leu Glu Leu Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 29
<211> LENGTH: 1326
<212> TYPE: DNA
<213> ORGANISM: Artificial Sequence
<220> FEATURE:
<223> OTHER INFORMATION: H11 heavy chain DNA (optimised)

<400> SEQUENCE: 29

```
caggtgcagc tcgtgcagag cggcgccgag gtgaaagaac ccggcgccag cgtgaaggtg    60
agctgcaagg gcagcggctt caacatcaaa gtgtactacg tgcactggct gaggcagctg   120
cccggaaagg gcctggagtg gattggcagg atcgaccccg agaacggcga ccatctac     180
accccccaagt tccaggacaa ggccaccctg accgtggaca ccagcaccga caccgcctac   240
atggaactga gcagcctgag gtccgaggat accgccgtct actactgcgt gagcagcggg   300
tattggggcc agggcacact agtgaccgtg agcagcgcca gcaccaaggg ccccagcgtg   360
ttccccctgg cccccagcag caagagcacc agcggcggca gccgcccct gggctgcctg    420
gtgaaggact acttccccga gcccgtgacc gtgtcctgga cagcggagc cctgacaagc    480
ggggtgcaca ccttccccgc cgtgctgcag agcagcggcc tgtacagcct gagcagcgtg   540
gtgacagtgc ccagcagcag cctgggcacc cagacctaca tctgcaacgt gaaccacaag   600
cccagcaaca ccaaggtgga caagaaggtg agcccaaga gctgcgacaa gacccacacc   660
tgcccccct gccctgcccc tgaactggcc ggagccccct ccgtgttcct gttcccccc    720
aagcccaagg acaccctgat gatcagccgg accccccgagg tgacctgcgt ggtggtggac   780
gtgagccacg aggaccctga ggtgaagttc aattggtacg tggacggcgt ggaggtgcac   840
aacgccaaga ccaagccccg ggaggaacag tacaacagca cctaccgggt ggtgtccgtg   900
ctgaccgtgc tgcaccagga ctggctgaac ggcaaagaat acaagtgcaa ggtgtccaac   960
aaggccctgc ctgcccccat cgagaaaacc atcagcaagg ccaagggcca gcccaggaa   1020
ccccaggtgt acaccctgcc ccctcccgg gacgagctga ccaagaacca ggtgtccctg   1080
acctgtctgg tgaagggctt ctaccccagc gacatcgccg tggagtggga gagcaacggc   1140
cagcccgaga caaactacaa gaccaccccc cctgtgctgg acagcgacgg cagcttcttc   1200
ctgtacagca agctgaccgt ggacaagagc cggtggcagc agggcaacgt gttcagctgc   1260
```

```
agcgtgatgc acgaggccct gcacaaccac tacacccaga agagcctgag cctgtccccc    1320
ggcaag                                                               1326

<210> SEQ ID NO 30
<211> LENGTH: 654
<212> TYPE: DNA
<213> ORGANISM: Artificial Sequence
<220> FEATURE:
<223> OTHER INFORMATION: L9 light chain DNA (optimised)

<400> SEQUENCE: 30
gacatcgtga tgacccagag cccactgagc aatcccgtga ctcccggcga gcccgcctca     60
atcagctgca ggagcagcaa gagcctgctg cacaggaacg gcatcaccta cctgtactgg    120
tatctgcaga agcccggcca gagcccccag ctgctgatct accagatgtc caacctggcc    180
agcggcgtgc ccgaccggtt ctctagcagc ggaagcggca ccgacttcac cctgaagatc    240
agcagggtgg aagccgagga cgtgggcgtg tactactgcg cccagaacct ggagctctgg    300
accttcggcc agggcaccaa ggtggagatc aaacgtacgg tggccgcccc cagcgtgttc    360
atcttccccc ccagcgatga gcagctgaag agcggcaccg ccagcgtggt gtgtctgctg    420
aacaacttct accccgggga ggccaaggtg cagtggaagg tggacaatgc cctgcagagc    480
ggcaacagcc aggagagcgt gaccgagcag gacagcaagg actccaccta cagcctgagc    540
agcaccctga ccctgagcaa ggccgactac gagaagcaca aggtgtacgc ctgtgaggtg    600
acccaccagg gcctgtccag ccccgtgacc aagagcttca ccggggcga gtgc           654

<210> SEQ ID NO 31
<211> LENGTH: 112
<212> TYPE: PRT
<213> ORGANISM: Mus muscularis

<400> SEQUENCE: 31

Glu Val Gln Leu Gln Gln Ser Gly Ala Glu Leu Val Lys Pro Gly Ala
 1               5                  10                  15

Ser Val Lys Leu Ser Cys Thr Gly Ser Gly Phe Asn Ile Lys Val Tyr
            20                  25                  30

Tyr Val His Trp Leu Lys Gln Leu Thr Glu Gln Gly Leu Glu Trp Ile
        35                  40                  45

Gly Arg Ile Asp Pro Glu Asn Gly Glu Thr Ile Tyr Ala Pro Lys Phe
    50                  55                  60

Gln Asp Lys Ala Thr Leu Thr Val Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Val Ser Ser Gly Tyr Trp Gly Gln Gly Thr Thr Leu Thr Val Ser Ser
            100                 105                 110

<210> SEQ ID NO 32
<211> LENGTH: 336
<212> TYPE: DNA
<213> ORGANISM: Mus muscularis

<400> SEQUENCE: 32
gaggttcagc tacagcagtc tggggcagag cttgtgaagc caggggcctc agtcaagttg     60
tcctgcacag gttctggctt caacattaag gtctactatg tgcactggct gaagcagttg    120
actgagcagg gcctggaatg gattggaagg attgatcctg aaaatggtga aactatatat    180
```

```
gccccgaaat tccaggacaa ggccactttg acagtagaca catcatccaa cacagcctac    240
ctgcagctca gcagcctgac atctgaggac actgccgtct attattgtgt tagttcgggc    300
tactggggcc aaggcaccac tctcacagtc tcctca                              336
```

<210> SEQ ID NO 33
<211> LENGTH: 111
<212> TYPE: PRT
<213> ORGANISM: Mus muscularis

<400> SEQUENCE: 33

```
Asp Ile Val Met Thr Gln Ser Ala Phe Ser Asn Pro Val Thr Leu Gly
1               5                   10                  15

Thr Ser Ala Ser Ile Ser Cys Arg Ser Ser Lys Ser Leu Leu His Arg
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Thr Ser Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Trp Thr Phe Gly Gly Gly Thr Lys Leu Glu Ile Lys
            100                 105                 110
```

<210> SEQ ID NO 34
<211> LENGTH: 333
<212> TYPE: DNA
<213> ORGANISM: Mus muscularis

<400> SEQUENCE: 34

```
gatattgtga tgacgcagtc tgcattctcc aatccagtca ctcttggaac atcagcttcc     60
atctcctgca ggtctagtaa gagtctccta cataggaatg gcatcaccta tttgtattgg    120
tatctgcaga agccaggcca gtctcctcag ctcctgattt atcagatgtc caaccttgcc    180
tcaggagtcc cagacaggtt cactagcagt gggtcaggaa ctgatttcac tctgaaaatc    240
agcagagtgg aggctgagga tgtgggtgtt tattactgtg ctcaaaatct agaactttgg    300
acgttcggtg gaggcaccaa gctggaaatc aaa                                 333
```

<210> SEQ ID NO 35
<211> LENGTH: 112
<212> TYPE: PRT
<213> ORGANISM: Mus muscularis

<400> SEQUENCE: 35

```
Glu Val Gln Leu Gln Gln Ser Gly Ala Glu Val Val Lys Pro Gly Ala
1               5                   10                  15

Ser Val Lys Leu Ser Cys Thr Ala Ser Gly Phe Asn Ile Lys Val Tyr
            20                  25                  30

Tyr Ile His Trp Leu Lys Gln Leu Thr Glu Gln Gly Leu Glu Trp Ile
        35                  40                  45

Gly Arg Ile Asp Pro Glu Asn Gly Glu Thr Lys Tyr Val Pro Lys Phe
    50                  55                  60

Gln Gly Lys Ala Thr Leu Thr Val Asp Thr Ser Ser Asn Thr Ala Tyr
65                  70                  75                  80
```

Leu His Leu Ser Ser Leu Thr Ser Glu Asp Thr Gly Val Tyr Tyr Cys
            85                  90                  95

Val Thr Ser Gly Tyr Trp Gly Gln Gly Thr Thr Leu Thr Val Ser Ser
            100                 105                 110

<210> SEQ ID NO 36
<211> LENGTH: 336
<212> TYPE: DNA
<213> ORGANISM: Mus muscularis

<400> SEQUENCE: 36
gaggttcagc tgcagcagtc tggggcagag gttgtgaagc caggggcctc agtcaagttg       60
tcctgcacag cttctggctt caacattaaa gtctactata tccactggtt gaagcagttg      120
actgagcagg gcctagaatg gattggaagg attgatcctg aaaatggtga actaagtat       180 gtcccgaaat tccagggcaa ggccacttta acagtagaca catcctccaa cacagcctac      240
ctgcacctca gcagcctgac atctgaggac actggcgtct attactgtgt tacctcgggc      300
tactggggcc aaggcaccac tctcacagtc tcctca                                336

<210> SEQ ID NO 37
<211> LENGTH: 111
<212> TYPE: PRT
<213> ORGANISM: Mus muscularis

<400> SEQUENCE: 37

Asp Ile Val Met Thr Gln Ala Ala Phe Ser Asn Pro Val Ala Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Trp Thr Phe Gly Gly Gly Thr Lys Leu Glu Ile Lys
            100                 105                 110

<210> SEQ ID NO 38
<211> LENGTH: 333
<212> TYPE: DNA
<213> ORGANISM: Mus muscularis

<400> SEQUENCE: 38
gatattgtga tgacgcaggc tgcattctcc aatccagtcg ctcttggaac atcagcttcc       60
atctcctgca ggtctagtaa gagtctccta catagtaatg gcatcactta tttgtattgg      120
tatctgcaga agccaggcca gtctcctcag ctcctgattt atcagatgtc caaccttgcc      180
tcaggagtcc cagacaggtt cagtagcagt gggtcaggaa ctgatttcac actgagaatc      240
agcagagtgg aggctgagga tgtgggtgtt tattactgtg ctcaaaatct agaactttgg      300
acgttcggtg gaggcaccaa gctggaaatc aaa                                   333

<210> SEQ ID NO 39
<211> LENGTH: 112
<212> TYPE: PRT

<213> ORGANISM: Mus muscularis

<400> SEQUENCE: 39

```
Glu Val Gln Leu Gln Gln Ser Gly Ala Glu Leu Val Glu Pro Gly Ala
1               5                   10                  15

Ser Val Lys Leu Ser Cys Thr Gly Ser Gly Phe Asn Ile Lys Val Tyr
            20                  25                  30

Tyr Val His Trp Leu Lys Gln Leu Thr Glu Gln Gly Leu Glu Trp Ile
        35                  40                  45

Gly Arg Ile Asp Pro Glu Asn Gly Glu Thr Leu Tyr Thr Pro Lys Phe
    50                  55                  60

Gln Gly Lys Ala Thr Leu Thr Val Asp Thr Ser Ser Asn Thr Ala Tyr
65                  70                  75                  80

Leu Gln Leu Asn Ser Leu Thr Ser Glu Asp Thr Ala Val Tyr Tyr Cys
                85                  90                  95

Val Ser Ser Gly Tyr Trp Gly Gln Gly Thr Ser Leu Thr Val Ser Ser
            100                 105                 110
```

<210> SEQ ID NO 40
<211> LENGTH: 336
<212> TYPE: DNA
<213> ORGANISM: Mus muscularis

<400> SEQUENCE: 40

```
gaggttcagc tgcagcagtc tggggcagag cttgtggagc caggggcctc agtcaagttg      60
tcctgcacag gttctggctt caacattaag gtctactatg ttcactggct gaagcagttg     120
actgagcagg gcctggaatg gattggaagg attgatcctg agaatggtga aactctatac     180
accccgaaat tccagggcaa ggccactttg acagtagaca catcatccaa cacagcctac     240
ctgcagctca acagcctgac atctgaggac actgccgtct attattgtgt tagttcgggc     300
tactggggcc aaggcacctc tctcacagtc tcctca                               336
```

<210> SEQ ID NO 41
<211> LENGTH: 111
<212> TYPE: PRT
<213> ORGANISM: Mus muscularis

<400> SEQUENCE: 41

```
Asp Ile Val Met Thr Gln Ser Ala Phe Ser Asn Pro Val Thr Leu Gly
1               5                   10                  15

Thr Ser Ala Ser Ile Ser Cys Arg Ser Ser Lys Ser Leu Leu His Arg
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Thr Ser Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Trp Thr Phe Gly Gly Gly Thr Lys Leu Glu Ile Lys
            100                 105                 110
```

<210> SEQ ID NO 42
<211> LENGTH: 333
<212> TYPE: DNA
<213> ORGANISM: Mus muscularis

<400> SEQUENCE: 42

```
gatattgtga tgacgcagtc tgcattctcc aatccagtca ctcttggaac atcagcttcc      60
atctcctgca ggtctagcaa gagtctccta cataggaatg gcatcaccta tttgtattgg     120
tatctgcaga agccaggcca gtctcctcag ctcctgattt atcagatgtc caaccttgcc     180
tcaggagtcc cagacaggtt cactagcagt gggtcaggaa ctgatttcac tctgaaaatc     240
agcagagtgg aggctgagga tgtgggtgtt tattactgtg ctcaaaatct agaactttgg     300
acgttcggtg aggcaccaa gctggaaatc aaa                                   333
```

<210> SEQ ID NO 43
<211> LENGTH: 112
<212> TYPE: PRT
<213> ORGANISM: Mus muscularis

<400> SEQUENCE: 43

Glu Val Gln Leu Gln Gln Ser Gly Ala Glu Phe Val Arg Pro Gly Ala
1               5                   10                  15

Ser Val Lys Leu Ser Cys Thr Ala Ser Gly Phe Asn Ile Lys Thr Tyr
            20                  25                  30

Tyr Ile His Trp Leu Lys Gln Arg Thr Asp Gln Gly Leu Glu Trp Ile
        35                  40                  45

Gly Arg Ile Asp Pro Glu Asp Gly Glu Thr Lys Phe Gly Pro Lys Phe
    50                  55                  60

Arg Gly Lys Ala Thr Leu Thr Ala Asp Thr Ser Ser Asn Thr Ala Ser
65                  70                  75                  80

Leu Gln Leu Ser Ser Leu Thr Ser Glu Asp Thr Gly Val Tyr Tyr Cys
                85                  90                  95

Val Thr Ser Gly Tyr Trp Gly Gln Gly Thr Thr Leu Ser Val Ser Ser
            100                 105                 110

<210> SEQ ID NO 44
<211> LENGTH: 336
<212> TYPE: DNA
<213> ORGANISM: Mus muscularis

<400> SEQUENCE: 44

```
gaggttcagc tgcagcagtc tggggcagag tttgtgaggc caggggcctc agtcaagtta     60
tcctgcacag cttctggctt caacattaaa acctactata tacactggct gaaacagagg    120
actgaccagg gcctggagtg gattggaagg attgatcccg aggatggtga aactaaattt    180
ggcccgaaat tccggggcaa ggccacttta acagcagaca tcctccaa cacagcctcc     240 ctacaactca gcagtctgac atctgaggac actggcgtct attactgtgt tacctcgggc    300
tactggggcc aaggcaccac tctctcagtc tcctca                              336
```

<210> SEQ ID NO 45
<211> LENGTH: 111
<212> TYPE: PRT
<213> ORGANISM: Mus muscularis

<400> SEQUENCE: 45

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser

```
                35                  40                  45
Pro Gln Leu Leu Ile Tyr Gln Met Ser Asn Leu Ala Ser Gly Val Pro
         50                  55                  60
Asp Arg Phe Ser Ser Gly Ser Gly Thr Asp Phe Thr Leu Arg Ile
 65                  70                  75                  80
Ser Arg Val Glu Ala Glu Asp Val Gly Val Tyr Tyr Cys Ala Gln Asn
                 85                  90                  95
Leu Glu Leu Trp Thr Phe Gly Gly Gly Thr Lys Leu Glu Ile Lys
            100                 105                 110
```

<210> SEQ ID NO 46
<211> LENGTH: 333
<212> TYPE: DNA
<213> ORGANISM: Mus muscularis

<400> SEQUENCE: 46

```
gatattgtga tgacgcaggc tgcattctcc aatccagtca ctcttggaac atcagcctcc    60
atctcctgca ggtctagtaa gagtctccta catagtaatg catcactta tttgtattgg   120
tatctgcaga agccaggcca gtctcctcag ctcttgattt atcagatgtc caaccttgcc   180
tcaggagtcc cagacaggtt cagtagcagt gggtcaggaa ctgatttcac actgagaatc   240
agcagagtgg aggctgagga tgtgggtgtt tattactgtg ctcaaaatct agaactttgg   300
acgttcggtg aggcaccaa gctggaaatc aaa                                333
```

<210> SEQ ID NO 47
<211> LENGTH: 112
<212> TYPE: PRT
<213> ORGANISM: Mus muscularis

<400> SEQUENCE: 47

```
Glu Val Gln Leu Gln Gln Ser Gly Ala Glu Leu Val Lys Pro Gly Ala
  1               5                  10                  15
Ser Val Lys Leu Ser Cys Thr Gly Ser Gly Phe Asn Ile Lys Val Tyr
             20                  25                  30
Tyr Val His Trp Leu Lys Gln Leu Thr Glu Gln Gly Leu Glu Trp Ile
         35                  40                  45
Gly Arg Ile Asp Pro Glu Asn Gly Glu Thr Lys Tyr Ala Pro Lys Phe
     50                  55                  60
Gln Asp Lys Ala Thr Leu Thr Val Asp Thr Ser Asn Thr Ala Tyr
 65                  70                  75                  80
Leu His Leu Ser Ser Leu Thr Ser Glu Asp Thr Ala Val Tyr Tyr Cys
                 85                  90                  95
Val Ser Ser Gly Tyr Trp Gly Gln Gly Thr Thr Leu Thr Val Ser Ser
            100                 105                 110
```

<210> SEQ ID NO 48
<211> LENGTH: 336
<212> TYPE: DNA
<213> ORGANISM: Mus muscularis

<400> SEQUENCE: 48

```
gaggttcagc tgcagcagtc tggggcagag cttgtgaagc caggggcctc agtcaagttg    60
tcctgcacag gttctggctt caacattaag gtctactatg tgcactggct gaagcagttg   120
actgagcagg gcctggaatg gattggaagg attgatcctg aaaatggtga aactaaatat   180
gccccgaaat tccaggacaa ggccactttg acagtagaca catcctccaa tacagcctac   240
```

```
cttcacctca gcagcctgac atctgaggac actgccgtct attattgtgt tagttcgggc    300
tactggggcc aaggcaccac tctcacagtc tcctca                              336
```

<210> SEQ ID NO 49
<211> LENGTH: 111
<212> TYPE: PRT
<213> ORGANISM: Mus muscularis

<400> SEQUENCE: 49

```
Asp Ile Val Met Thr Gln Ser Ala Phe Ser Asn Pro Val Thr Leu Gly
 1               5                  10                  15

Thr Ser Ala Ser Ile Ser Cys Arg Ser Ser Lys Ser Leu Leu His Arg
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Thr Ser Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Trp Thr Phe Gly Gly Gly Thr Lys Leu Glu Ile Lys
            100                 105                 110
```

<210> SEQ ID NO 50
<211> LENGTH: 333
<212> TYPE: DNA
<213> ORGANISM: Mus muscularis

<400> SEQUENCE: 50

```
gacattgtga tgacgcagtc tgcattctcc aatccagtca ctcttggaac atcagcttcc     60
atctcctgca ggtctagtaa gagtctccta cataggaatg gcatcaccta tttgtattgg    120
tatctgcaga agccaggcca gtctcctcag ctcctgattt atcagatgtc caaccttgcc    180
tcaggagtcc cagacaggtt cactagcagt gggtcaggaa ctgatttcac tctgaaaatc    240
agcagagtgg aggctgagga tgtgggtgtt tattattgtg ctcaaaatct agaactttgg    300
acgttcggtg gaggcaccaa gctggaaatc aaa                                 333
```

<210> SEQ ID NO 51
<211> LENGTH: 112
<212> TYPE: PRT
<213> ORGANISM: Mus muscularis

<400> SEQUENCE: 51

```
Glu Val Gln Leu Gln Gln Ser Gly Ala Glu Leu Val Glu Pro Gly Ala
 1               5                  10                  15

Ser Val Lys Leu Ser Cys Thr Gly Ser Gly Phe Asn Ile Lys Val Tyr
            20                  25                  30

Tyr Val His Trp Leu Lys Gln Leu Thr Glu Gln Gly Leu Glu Trp Ile
        35                  40                  45

Gly Arg Ile Asp Pro Glu Asn Gly Glu Thr Leu Tyr Thr Pro Lys Phe
    50                  55                  60

Gln Gly Lys Ala Thr Phe Thr Val Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95
```

Val Ser Ser Gly Tyr Trp Gly Gln Gly Thr Thr Leu Thr Val Ser Ser
            100                 105                 110

<210> SEQ ID NO 52
<211> LENGTH: 336
<212> TYPE: DNA
<213> ORGANISM: Mus muscularis

<400> SEQUENCE: 52

```
gaggttcagc tgcagcagtc tggggcagag cttgtggagc caggggcctc agtcaagttg      60
tcctgcacag gttctggctt caacattaag gtctactatg ttcactggct gaagcagttg     120
actgagcagg gcctggaatg gattggaagg attgatcctg agaatggtga aactctatat     180
accccgaaat tccagggcaa ggccactttt acagtagaca tcatccaa cacagcctac       240
ctgcagctca gcagcctgac atctgaggac actgccgtct attattgtgt tagttcgggc     300
tactggggcc aaggcaccac tctcacagtc tcctca                               336
```

<210> SEQ ID NO 53
<211> LENGTH: 111
<212> TYPE: PRT
<213> ORGANISM: Mus muscularis

<400> SEQUENCE: 53

Asp Ile Val Met Thr Gln Ser Ala Phe Ser Asn Pro Val Thr Leu Gly
1               5                   10                  15

Thr Ser Ala Ser Ile Ser Cys Arg Ser Ser Lys Ser Leu Leu His Arg
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Thr Ser Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Trp Thr Phe Gly Gly Gly Thr Lys Leu Glu Ile Lys
            100                 105                 110

<210> SEQ ID NO 54
<211> LENGTH: 333
<212> TYPE: DNA
<213> ORGANISM: Mus muscularis

<400> SEQUENCE: 54

```
gatattgtga tgacgcagtc tgcattctcc aatccagtca ctcttggaac atcagcttcc      60
atctcctgca ggtctagcaa gagtctccta cataggaatg gcatcaccta tttgtattgg     120
tatctgcaga agccaggcca gtctcctcag ctcctgattt atcagatgtc caaccttgcc     180
tcaggagtcc cagacaggtt cactagcagt gggtcaggaa ctgatttcac tctgaaaatc     240
agcagagtgg aggctgagga tgtgggtgtt tattactgtg ctcaaaatct agaactttgg     300
acgttcggtg aggcaccaa gctggaaatc aaa                                   333
```

<210> SEQ ID NO 55
<211> LENGTH: 112
<212> TYPE: PRT
<213> ORGANISM: Mus muscularis

<400> SEQUENCE: 55

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Met His Trp Leu Lys Gln Leu Thr Glu Gln Gly Leu Glu Trp Ile
        35                  40                  45

Gly Arg Ile Asp Pro Glu Asn Gly Glu Thr Gln Tyr Ala Pro Lys Phe
    50                  55                  60

Gln Gly Lys Ala Ser Leu Thr Ala Asp Thr Ser Ser Asn Thr Ala Tyr
65                  70                  75                  80

Leu His Leu Ser Ser Leu Thr Ser Glu Asp Thr Ala Val Tyr Tyr Cys
                85                  90                  95

Val Ser Ser Gly Tyr Trp Gly Gln Gly Thr Thr Leu Thr Val Ser Ser
            100                 105                 110

<210> SEQ ID NO 56
<211> LENGTH: 336
<212> TYPE: DNA
<213> ORGANISM: Mus muscularis

<400> SEQUENCE: 56
gaggttcagc tgcagcagtc tggggcagag cttgtgaagc caggggcctc agtcaagttg      60
tcctgcacag cttctggctt caacattaaa gactactata tgcactggtt gaagcagttg     120
actgagcagg gcctggaatg gattggaagg attgatcctg aaaatggtga aactcaatat     180
gccccgaaat tccagggcaa ggcctcttta acagcagaca catcctccaa cacagcctac     240
cttcacctca gcagcctgac atctgaggac actgccgtct attactgtgt tagttcgggc     300
tactggggcc aaggcaccac tctcacagtc tcctca                               336

<210> SEQ ID NO 57
<211> LENGTH: 111
<212> TYPE: PRT
<213> ORGANISM: Mus muscularis

<400> SEQUENCE: 57

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Trp Thr Phe Gly Gly Gly Thr Lys Leu Glu Ile Lys
            100                 105                 110

<210> SEQ ID NO 58
<211> LENGTH: 333
<212> TYPE: DNA
<213> ORGANISM: Mus muscularis

<400> SEQUENCE: 58

```
gatattgtga tgacgcaggc tgcattctcc aatccagtca ctcttggaac atcagcttcc    60
atctcctgca ggtctagtaa gagtctccta catagtaatg catcactta tttgtattgg    120 tatctgcaga agccaggcca gtctcctcag ctcctgattt atcagatgtc caaccttgcc   180
tcaggagtcc cagacaggtt cagtagcagt gggtcaggaa ctgatttcac actgagaatc   240
agcagagtgg aggctgagga tgtgggtgtt tattactgtg ctcaaaatct agaactttgg   300
acgttcggtg aggcaccaa gctggaaatc aaa                                 333
```

<210> SEQ ID NO 59
<211> LENGTH: 112
<212> TYPE: PRT
<213> ORGANISM: Artificial Sequence
<220> FEATURE:
<223> OTHER INFORMATION: H48 heavy chain aa

<400> SEQUENCE: 59

Gln Val Gln Leu Val Gln Ser Gly Ala Glu Val Lys Glu Pro Gly Ala
1               5                   10                  15

Ser Val Lys Val Ser Cys Lys Gly Ser Gly Phe Asn Ile His Val Tyr
            20                  25                  30

Tyr Val His Trp Leu Arg Gln Leu Pro Glu Lys Gly Leu Glu Trp Ile
        35                  40                  45

Gly Arg Ile Asp Pro Glu Asn Gly Glu Thr Ile Tyr Thr Pro Lys Phe
    50                  55                  60

Gln Asp Lys Ala Thr Leu Thr Val Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Val Ser Ser Gly Tyr Trp Gly Gln Gly Thr Leu Val Thr Val Ser Ser
            100                 105                 110

<210> SEQ ID NO 60
<211> LENGTH: 336
<212> TYPE: DNA
<213> ORGANISM: Artificial Sequence
<220> FEATURE:
<223> OTHER INFORMATION: H48 heavy chain DNA

<400> SEQUENCE: 60

```
caggtgcagc tcgtgcagag cggcgccgag gtgaaagaac ccggcgccag cgtgaaggtg    60
agctgcaagg gcagcggctt caacatccac gtgtactacg tgcactggct gaggcagctg   120
cccgagaagg gcctggagtg gattggcagg atcgaccccg agaacggcga gaccatctac   180 accccccaagt tccaggacaa ggccaccctg accgtggaca ccagcaccga caccgcctac   240
atggaactga gcctgag gtccgaggat accgccgtct actactgcgt gagcagcggg   300
tattggggcc agggcacact agtgaccgtg tccagc                              336
```

<210> SEQ ID NO 61
<211> LENGTH: 112
<212> TYPE: PRT
<213> ORGANISM: Artificial Sequence
<220> FEATURE:
<223> OTHER INFORMATION: H49 heavy chain aa

<400> SEQUENCE: 61

Gln Val Gln Leu Val Gln Ser Gly Ala Glu Val Lys Glu Pro Gly Ala
1               5                   10                  15

Ser Val Lys Val Ser Cys Lys Gly Ser Gly Phe Asn Ile Lys Thr Tyr

```
                20                  25                  30
Tyr Val His Trp Leu Arg Gln Leu Pro Glu Lys Gly Leu Glu Trp Ile
            35                  40                  45

Gly Arg Ile Asp Pro Glu Asn Gly Glu Thr Ile Tyr Thr Pro Lys Phe
 50                  55                  60

Gln Asp Lys Ala Thr Leu Thr Val Asp Thr Ser Thr Asp Thr Ala Tyr
 65                  70                  75                  80

Met Glu Leu Ser Ser Leu Arg Ser Glu Asp Thr Ala Val Tyr Tyr Cys
                85                  90                  95

Val Ser Ser Gly Tyr Trp Gly Gln Gly Thr Leu Val Thr Val Ser Ser
            100                 105                 110

<210> SEQ ID NO 62
<211> LENGTH: 336
<212> TYPE: DNA
<213> ORGANISM: Artificial Sequence
<220> FEATURE:
<223> OTHER INFORMATION: H49 heavy chain DNA

<400> SEQUENCE: 62
caggtgcagc tcgtgcagag cggcgccgag gtgaaagaac ccggcgccag cgtgaaggtg      60
agctgcaagg gcagcggctt caacatcaaa acctactacg tgcactggct gaggcagctg     120
cccgagaagg gcctggagtg gattggcagg atcgaccccg agaacggcga gaccatctac     180
acccccaagt tccaggacaa ggccaccctg accgtggaca ccagcaccga caccgcctac     240
atggaactga gcagcctgag gtccgaggat accgccgtct actactgcgt gagcagcggg     300
tattggggcc agggcacact agtgaccgtg tccagc                               336

<210> SEQ ID NO 63
<211> LENGTH: 112
<212> TYPE: PRT
<213> ORGANISM: Artificial Sequence
<220> FEATURE:
<223> OTHER INFORMATION: H50 heavy chain aa

<400> SEQUENCE: 63

Gln Val Gln Leu Val Gln Ser Gly Ala Glu Val Lys Glu Pro Gly Ala
 1               5                  10                  15

Ser Val Lys Val Ser Cys Thr Gly Ser Gly Phe Asn Ile His Val Tyr
            20                  25                  30

Tyr Val His Trp Leu Arg Gln Leu Pro Glu Lys Gly Leu Glu Trp Ile
            35                  40                  45

Gly Arg Ile Asp Pro Glu Asn Gly Glu Thr Ile Tyr Thr Pro Lys Phe
 50                  55                  60

Gln Asp Lys Ala Thr Leu Thr Val Asp Thr Ser Thr Asp Thr Ala Tyr
 65                  70                  75                  80

Met Glu Leu Ser Ser Leu Arg Ser Glu Asp Thr Ala Val Tyr Tyr Cys
                85                  90                  95

Val Ser Ser Gly Tyr Trp Gly Gln Gly Thr Leu Val Thr Val Ser Ser
            100                 105                 110

<210> SEQ ID NO 64
<211> LENGTH: 336
<212> TYPE: DNA
<213> ORGANISM: Artificial Sequence
<220> FEATURE:
<223> OTHER INFORMATION: H50 heavy chain DNA

<400> SEQUENCE: 64
```

```
caggtgcagc tcgtgcagag cggcgccgag gtgaaagaac ccggcgccag cgtgaaggtg      60
agctgcaccg gcagcggctt caacatccac gtgtactacg tgcactggct gaggcagctg     120
cccgagaagg gcctggagtg gattggcagg atcgaccccg agaacggcga gaccatctac     180 accccccaagt tccaggacaa ggccaccctg accgtggaca ccagcaccga caccgcctac    240
atggaactga gcagcctgag gtccgaggat accgccgtct actactgcgt gagcagcggg    300
tattggggcc agggcacact agtgaccgtg tccagc                              336
```

<210> SEQ ID NO 65
<211> LENGTH: 112
<212> TYPE: PRT
<213> ORGANISM: Artificial Sequence
<220> FEATURE:
<223> OTHER INFORMATION: H51 heavy chain aa

<400> SEQUENCE: 65

```
Gln Val Gln Leu Val Gln Ser Gly Ala Glu Val Lys Glu Pro Gly Ala
  1               5                  10                  15

Ser Val Lys Val Ser Cys Lys Gly Ser Gly Phe Asn Ile His Thr Tyr
                 20                  25                  30

Tyr Val His Trp Leu Arg Gln Leu Pro Glu Lys Gly Leu Glu Trp Ile
             35                  40                  45

Gly Arg Ile Asp Pro Glu Asn Gly Glu Thr Ile Tyr Thr Pro Lys Phe
         50                  55                  60

Gln Asp Lys Ala Thr Leu Thr Val Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Val Ser Ser Gly Tyr Trp Gly Gln Gly Thr Leu Val Thr Val Ser Ser
            100                 105                 110
```

<210> SEQ ID NO 66
<211> LENGTH: 336
<212> TYPE: DNA
<213> ORGANISM: Artificial Sequence
<220> FEATURE:
<223> OTHER INFORMATION: H51 heavy chain DNA

<400> SEQUENCE: 66

```
caggtgcagc tcgtgcagag cggcgccgag gtgaaagaac ccggcgccag cgtgaaggtg      60
agctgcaagg gcagcggctt caacatccac acctactacg tgcactggct gaggcagctg    120
cccgagaagg gcctggagtg gattggcagg atcgaccccg agaacggcga gaccatctac    180 accccccaagt tccaggacaa ggccaccctg accgtggaca ccagcaccga caccgcctac    240
atggaactga gcagcctgag gtccgaggat accgccgtct actactgcgt gagcagcggg    300
tattggggcc agggcacact agtgaccgtg tccagc                              336
```

<210> SEQ ID NO 67
<211> LENGTH: 111
<212> TYPE: PRT
<213> ORGANISM: Artificial Sequence
<220> FEATURE:
<223> OTHER INFORMATION: L19 light chain aa

<400> SEQUENCE: 67

```
Asp Ile Val Met Thr Gln Ser Pro Leu Ser Asn Pro Val Thr Pro Gly
  1               5                  10                  15
```

```
Glu Pro Ala Ser Ile Ser Cys Arg Ser Ser Lys Ser Leu Leu His Arg
            20                  25                  30

Asn Gly Lys Thr Tyr Leu Tyr Trp Tyr Leu Gln Lys Pro Gly Gln Ser
        35                  40                  45

Pro Gln Leu Leu Ile Tyr Gln Met Asp His Leu Ala Ser Gly Val Pro
    50                  55                  60

Asp Arg Phe Ser Ser Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Trp Thr Phe Gly Gln Gly Thr Lys Val Glu Ile Lys
            100                 105                 110
```

<210> SEQ ID NO 68
<211> LENGTH: 333
<212> TYPE: DNA
<213> ORGANISM: Artificial Sequence
<220> FEATURE:
<223> OTHER INFORMATION: L19 light chain DNA

<400> SEQUENCE: 68

```
gacatcgtga tgacccagag cccactgagc aatcccgtga ctcccggcga gcccgcctca      60
atcagctgca ggagcagcaa gagcctgctg cacaggaacg gcaagaccta cctgtactgg     120
tatctgcaga agcccggcca gagccccag ctgctgatct accagatgga ccacctggcc     180
agcggcgtgc ccgaccggtt ctctagcagc ggaagcggca ccgacttcac cctgaagatc     240
agcagggtgg aagccgagga cgtgggcgtg tactactgcg cccagaacct ggagctctgg     300
accttcggcc agggcaccaa ggtggagatc aaa                                 333
```

<210> SEQ ID NO 69
<211> LENGTH: 111
<212> TYPE: PRT
<213> ORGANISM: Artificial Sequence
<220> FEATURE:
<223> OTHER INFORMATION: L20 light chain aa

<400> SEQUENCE: 69

```
Asp Ile Val Met Thr Gln Ser Pro Leu Ser Asn Pro Val Thr Pro Gly
1               5                   10                  15

Glu Pro Ala Ser Ile Ser Cys Arg Ser Ser Lys Ser Leu Leu His Arg
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Asp His Leu Ala Ser Gly Val Pro
    50                  55                  60

Asp Arg Phe Ser Ser Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Trp Thr Phe Gly Gln Gly Thr Lys Val Glu Ile Lys
            100                 105                 110
```

<210> SEQ ID NO 70
<211> LENGTH: 333
<212> TYPE: DNA
<213> ORGANISM: Artificial Sequence
<220> FEATURE:
<223> OTHER INFORMATION: L20 light chain DNA -continued

<400> SEQUENCE: 70

```
gacatcgtga tgacccagag cccactgagc aatcccgtga ctcccggcga gcccgcctca    60
atcagctgca ggagcagcaa gagcctgctg cacaggaacg gcatcaccta cctgtactgg   120
tatctgcaga agcccggcca gagcccccag ctgctgatct accagatgga ccacctggcc   180
agcggcgtgc cgaccggtt ctctagcagc ggaagcggca ccgacttcac cctgaagatc   240
agcagggtgg aagccgagga cgtgggcgtg tactactgcg cccagaacct ggagctctgg   300
accttcggcc agggcaccaa ggtggagatc aaa                               333
```

<210> SEQ ID NO 71
<211> LENGTH: 111
<212> TYPE: PRT
<213> ORGANISM: Artificial Sequence
<220> FEATURE:
<223> OTHER INFORMATION: L21 light chain aa

<400> SEQUENCE: 71

```
Asp Ile Val Met Thr Gln Ser Pro Leu Ser Asn Pro Val Thr Pro Gly
 1               5                  10                  15
Glu Pro Ala Ser Ile Ser Cys Arg Ser Ser Lys Ser Leu Leu His Arg
            20                  25                  30
Asn Gly Lys Thr Tyr Leu Tyr Trp Tyr Leu Gln Lys Pro Gly Gln Ser
        35                  40                  45
Pro Gln Leu Leu Ile Tyr Gln Met Asp Asn Leu Ala Ser Gly Val Pro
    50                  55                  60
Asp Arg Phe Ser Ser Ser Gly Ser Gly Thr Asp Phe Thr Leu Lys Ile
65                  70                  75                  80
Ser Arg Val Glu Ala Glu Asp Val Gly Val Tyr Tyr Cys Ala Gln Asn
                85                  90                  95
Leu Glu Leu Trp Thr Phe Gly Gln Gly Thr Lys Val Glu Ile Lys
            100                 105                 110
```

<210> SEQ ID NO 72
<211> LENGTH: 333
<212> TYPE: DNA
<213> ORGANISM: Artificial Sequence
<220> FEATURE:
<223> OTHER INFORMATION: L21 light chain DNA

<400> SEQUENCE: 72

```
gacatcgtga tgacccagag cccactgagc aatcccgtga ctcccggcga gcccgcctca    60
atcagctgca ggagcagcaa gagcctgctg cacaggaacg gcaagaccta cctgtactgg   120
tatctgcaga agcccggcca gagcccccag ctgctgatct accagatgga caacctggcc   180
agcggcgtgc cgaccggtt ctctagcagc ggaagcggca ccgacttcac cctgaagatc   240
agcagggtgg aagccgagga cgtgggcgtg tactactgcg cccagaacct ggagctctgg   300
accttcggcc agggcaccaa ggtggagatc aaa                               333
```

<210> SEQ ID NO 73
<211> LENGTH: 21
<212> TYPE: PRT
<213> ORGANISM: Artificial Sequence
<220> FEATURE:
<223> OTHER INFORMATION: peptide conjugate containing beta amyloid
      residues 22-38 used for immunisation and screening

```
<400> SEQUENCE: 73

Cys Gly Gly Gly Glu Asp Val Gly Ser Asn Lys Gly Ala Ile Ile Gly
1               5                   10                  15

Leu Met Val Gly Gly
            20
```